US006214581B1

(12) United States Patent
Lynch et al.

(10) Patent No.: US 6,214,581 B1
(45) Date of Patent: Apr. 10, 2001

(54) NUCLEIC ACIDS ENCODING A FUNCTIONAL HUMAN PURINORECEPTOR P2X3 AND P2X6, AND METHODS OF PRODUCTION AND USE THEREOF

(75) Inventors: Kevin J. Lynch, Gurnee; Edward C. Burgard, Libertyville; Tim van Biesen, Chicago, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/191,136

(22) Filed: Nov. 13, 1998

Related U.S. Application Data

(63) Continuation-in-part of application No. 09/008,526, filed on Jan. 16, 1998, now abandoned, and a continuation-in-part of application No. 09/008,185, filed on Jan. 16, 1998, now abandoned.
(60) Provisional application No. 60/071,298, filed on Jan. 16, 1998, and provisional application No. 60/071,669, filed on Jan. 16, 1998.

(51) Int. Cl.$^7$ ........................... C12N 15/12; C07K 14/705
(52) U.S. Cl. .................. 435/69.1; 435/252.3; 435/320.1; 530/350; 536/23.5
(58) Field of Search .............................. 435/69.1, 252.3, 435/320.1; 530/350; 536/23.5

(56) References Cited

U.S. PATENT DOCUMENTS

| | | |
|---|---|---|
| 4,683,195 | 7/1987 | Mullis et al. . |
| 4,683,202 | 7/1987 | Mullis . |
| 4,800,159 | 1/1989 | Mullis et al. . |
| 4,965,188 | 10/1990 | Mullis et al. . |
| 5,607,836 | 3/1997 | Boucher et al. . |

FOREIGN PATENT DOCUMENTS

| | | |
|---|---|---|
| 95/33048 | 12/1995 | (WO) . |
| 9842835 | 1/1998 | (WO) . |

OTHER PUBLICATIONS

Valera, et al., (1994) Nature 371:516–519.
Brake, et al., (1994) Nature 371:519–523.
Lewis, et al., (1995) Nature 377:432–435.
Chen, et al., (1995) Nature 377:428–431.
Buell, et al., (1996 EMBO J. 15:55–62.
Seguela, et al., (1996) J. of Neuroscience 16:448–455.
Bo, et al., (1995) FEBS Lett. 375:129–133.
Soto, et al., (1996) Proc. Natl. Acad. Sci. USA 93:3684–3688.
Wang, et al., (1996) Biochem. Biophys. Res. Commun. 220:196–202.
Collo, et al., ((1996) J. Neurosci. 16:2495–2507.
Garcua–Guzman, et al., (1996) FEBS Lett. 388:123–127.
Soto, et al., (1996) Biochem. Biophys. Res. Commun. 223:456–460.
Surprenant, et al., (1996) Science 272:735–738.
Buell, et al., (1996) Eur. J. Neurosci. 8:2221–2228.
Grunstein, et al., (1975) Proc. Natl. Acad. Sci. USA 72:3961–3965.
Warner (1984) DNA 3:401–411.
Zoller (1982) Nucleic Acids Res. 10:6487–6500.
Clewell, et al., (1972) J. Bacteriol. 110:667–676.
Sanger, et al., (1977) Proc. Natl. Acad. Sci. USA 74:5463–5467.
Messing, et al., (1981) Nucleic Acid Res. 9:309–321.
Maxam, et al., (1980) Meth. Enzymol. 65:499–560.
Barr, et al., (1986) Biotechniques 4:428–432.
Foresta, et al., (1992) J. Biol. Chem. 257:19443–19447.
Goeddel, et al., (1977) Nucleic Acid Res. 8:4057–4074.
Shimatake, et al., (1981) Nature 292:128–132.
De Boer, et al., (1983) Proc. Natl. Acad. Sci. 80:21–25.
Broach, et al., (1983) Methol. Enzymol. 101:307–325.
Hess, et al., (1968) J. Adv. Enzyme Reg. 7:149–167.
Holland, et al., (1978) Biochemistry 17:4900–4908.
Hitzeman (1980) J. Biol. Chem. 255:12073–12080.
Cousins, et al., (1987) Gene 61:265–275.
Gopalakrishnan, et al., (1995) Eur. J. Pharmacol.–Mol. Pharmacol. 290:237–246.
Briggs, et al., (1995) Neuropharmacol 34:583–590.
Stühmer (1992) Meth. Enzymol. 207:319–339.
Summers & Smith, Texas Agricultural Experiment Station Bulletin No. 1555 (1987).
Wisniewski, et al., (1996) Biochem. J. 313:575–580.
Suzuki, et al., (1994) Science 264:1336–1340.
Gravina, et al., (1995) J. Biol. Chem. 270:7013–7016.
Turner, et al., (1996) J. Biol. Chem. 271:8966–8970.
Altschul (1983) J. Mol. Evol. 36:290–300.
Frohman, et al., (1988) Proc. Natl. Acad. Sci. USA 85:8998–9002.
Kozak (1984) Nucleic Acids Res. 12:857–872.
Wang, et al., (1990) Biochem. Biophys. Res. Commun. 166:251–258.
Kennedy and Leff (1995) Nature 477:385–386.
Garcia–Guzman, M., et al., "Characterization of Recombinant Human P2X$_4$ Receptor Reveals Pharmacological Differences to the Rat Homologue", *Molecular Pharmacology*, 51:109–118 (1997).

(List continued on next page.)

*Primary Examiner*—John Ulm
(74) *Attorney, Agent, or Firm*—Cheryl L. Becker; Mimi C. Goller

(57) ABSTRACT

Human P2X$_3$ and P2X$_6$ purinergic receptor polypeptides are provided. Nucleic acid molecules encoding the aforementioned human P2X receptor polypeptide, and vectors and host cells containing such nucleic acid molecules, are also provided. In addition, methods are provided for producing these P2X receptor polypeptide, as are methods of using such polypeptides and host cells that express the same to screen for compounds having activity on P2X$_3$ and P2X$_6$ receptors. Further, therapeutic uses involving aspects of these receptors are contemplated.

14 Claims, 16 Drawing Sheets

OTHER PUBLICATIONS

Garcia–Guzman, M., et al., "Molecular characterization and pharmacological properties of the human P2X$_3$ purinoreceptor", *Molecular Brain Research,* 47:59–66 (1997).

Souslova, V., et al., "Structure and chromosomal mapping of the mouse P2X$_3$ gene", *Gene: An International Journh. On Genes and Genomes* , 195(1): 101–111 (1997).

Hansen, M.A., et al., "Structural Motif and Characteristics of the Extracellular Domain of P2X Receptors", *Biochemical and Biophysical Res. Comm.,* 236:670–675 (1997).

Radford, K.M., et al., "Baculovirus Expression Provides Direct Evidence for Heteromeric Assembly of P2X$_2$ and P2X$_3$ Receptors", *Journ. of Neurosci,* 17(17):6529–6533 (1997).

North, R.A., "P2X purinoceptor plethora", *The Neuroscience,* 8:187–194 (1996).

Vulchanova, L., et al., "Immunohistochemical Study of the P2X$_2$ and P2X$_3$ Receptor Subunites in Rat and Monkey Sensory Neurons and their Central Terminals", *Neuropharmacology,* 36(9):1229–1242 (1997).

Bradbury, E. J., et al., "The Expression of P2X$_3$ Purinoreceptors in Sensory Neurons: Effects of Axotomy and Glial–Derived Neurotrophic Factor", *Molecular and Cellular Neurosecience,* 12:256–268 (1998).

Nicke, A., et al., "P2X$_1$ and P2X$_3$ receptors form stable trimers: a novel structural motif of ligand–gated ion channels", *The EMBO Journ.,* 17(11):3016–3028 (1998).

Longhurst et al. The Human P2X1 Receptor: Molecular Cloning, Tissue Distribution, and Localization to Chromosome 17. Biochimica et Biopgysica Acta. Sep. 11 1996. vol. 1308, No. 3, pp. 185–188.

FIGURE 1

CTACTACTACTAGGCCACGCGTCGACTAGTACGGGGGGGGGGGGGGGACCGGGGACGACCAC
CACCTACCTCCTCAGGCTGCGGCCTCGCGAGGGCCCCGGCGCGAGAGGACCCCCCTCTCCTG
AGGCCACCACTGGGCCCCCTTCTGAGTGTCCCCTGAGCACTCTCTCAGCATGAACTGCATAT
CCGACTTCTTCACCTATGAGACCACCAAGTCGGTGGTTGTGAAAAGCTGGACCATCGGGATC
ATCAACCGAGTAGTTCAGCTTCTGATCATCTCCTACTTTGTAGGGTGGGTTTTCTTGCACGA
GAAGGCTTACCAGGTACGGGACACAGCCATTAAGTCCTCGGTGGTAACCAAGGTGAAGGGCT
CCGGACTCTACACCAACAGAGTCATGGATGTGTCTGATTACGTGACGCCACCTCAGGGCACC
TCGGTCTTTGTCATCATCACCAAGATGATTGTTACTGAAAATCAGATGCAAGGATTCTGCCC
AGAGAGTGAGGAGAAATACCGCTGTGTATCAGACAGCCAGTGCGGGCCTGAGCGCTTGCCAG
GGATCCTCACTGGCCGCTGCGTGAACTACAGCTCTGCGCTCCGGACCTGTGAGATCCAGGGC
TGGTGCCCCACGGAGGTGGACACAGTGGAAACGCCCATCATGATGGAAGCTGAGAACTTCAC
TATTTTCATCAAGAACAGCATCCGTTTCCCCCTCTTCAACTTTGAGAAGGGAAACCTCCTTC
CCAACCTGACAGCCAGGGACATGAAGACCTGCCGCTTCCACCCGGACAAGGACCCTTTCTAC
CCCATCTTGCGGGTAGGGGACGTGGTCAAGTTTGCGGGGCAGGATTTTGCCAAACTGGCGCG
CACGGGGGGAGTTCTGGGCATTAAGATCGGCTGGGTGTGCGACTTGGACAAGGCCTGGGACC
AGTGCATCCCCAAATACTCCTTCACCCGGCTCGACAGCGTTTCTGAGAAAAGCAGCGTGTCC
CCAGGCTACAACTTCAGGTTTGCCAAGTACTACAAAATGGAAAATGGCAGTGAGTACCGCAC
CCTCCTGAAGGCTTTTGGCATCCGCTTCGACGTGCTGGTATACGGGAATGCTGGCAAGTTCA
ACATCATCCCCACCATCATCAGCTCTGTGGCGGCCTTTACTTCTGTGGGAGTGGGAACTGTT
CTCTGTGACATCATCCTGCTCAACTTCCTCAGGGGGGCCGACCAGTACAAAGCCAAGAAGTT
TGAGGAGGTGAATGAGACTACACTGAAAATCG (SEQ ID NO:13)

FIGURE 2

ACCACAGTGGAGAAGCAGTCCACCGATTCGGGGGCCTTCTCCATAGGCCACTAGGGCCTCTT
TCCAGGGCCCCACACTCACAAAGGCTCCAGGCCTCCCCACAGAGGACCCTGCCTGAGCAAGG
GGGCATGGGAGGGAAGAGGGGCTCTCATTTCTGCTGCTCATTCCATGAGCATAGCTGGGACC
CAAGTGTCTGGGCCTCCGACTGCTCCAGCAGACAGGCAGTGCTCCCTGCTGAGACCCCAGTC
TCACCTTCACTCCTTGCCTGGCCCCATCTGCTTCCTAGGACCCCTGGGGCAGGAGCACCTGA
GCCATCCCCTTCCCAAAGAGTAGAGATTATAATGTAGGACAGATGGCCACAAGGGCCTACCA
AGTGCCAGGCACTTTCACACACGTTATCTCATTTAATCCTTAGAATAATCCTATGAGGTAGA
TATTAGTTTCCCTTGTTTTGAAGATAAACCAAGGCTCAGAGAGACTGAGTCATTTGCCCCAG
GCCAGATAGCCAGGATGTGAGAGAGCTGGGATTTGAACGTCCGTCTGACTAACTCCATCGCC
CACACCCCATGAGAGAAGATGAACTCCCAGGGTCCATCAGCCCTGCTGCTTCAGCCGCCTCC
ACCCTGACGGTGATTCGGTTAATAAAGAGTAAGCCCCAAAAAAAAAAAAAAAAAAAAAAAAA
AAAAGTACTAGTCGACGCGTGGCC (SEQ ID NO:14)

FIGURE 3

GAATTCCTGCAGCCCGGGGGGATCCGCCCCACCATGAACTGCATATCCGACTTCTTCACCT
ATGAGACCACCAAGTCGGTGGTTGTGAAGAGCTGGACCATCGGGATCATCAACCGAGTAGT
TCAGCTTCTGATCATCTCCTACTTTGTAGGGTGGGTTTTCTTGCACGAGAAGGCTTACCAG
GTACGGGACACAGCCATTGAGTCCTCGGTGGTAACCAAGGTGAAGGGCTCCGGACTCTACG
CCAACAGAGTCATGGATGTGTCTGATTACGTGACGCCACCTCAGGGCACCTCGGTCTTTGT
CATCATCACCAAGATGATTGTTACTGAAAATCAGATGCAAGGATTCTGCCCAGAGAGTGAG
GAGAAATACCGCTGTGTATCAGACAGCCAGTGCGGGCCTGAGCGCTTGCCAGGTGGGGGA
TCCTCACTGGCCGCTGCGTGAACTACAGCTCTGTGCTCCGGACCTGTGAGATCCAGGGCTG
GTGCCCCACGGAGGTGGACACAGTGGAAACGCCCATCATGATGGAAGCTGAGAACTTCACT
ATTTTCATCAAGAACAGCATCCGTTTCCCCCTCTTCAACTTTGAGAAGGGAAACCTCCTTC
CCAACCTGACAGCCAGGGACATGAAGACCTGCCGCTTCCACCCGGACAAGGACCCTTTCTG
CCCCATCTTGCGGGTAGGGACGTGGTCAAGTTTGCGGGACAGGATTTTGCCAAACTGGCG
CGCACGGGGGAGTTCTGGGCATTAAGATCGGCTGGGTGTGCGACTTGGACAAGGCCTGGG
ACCAGTGCATCCCCAAATACTCCTTCACCCGGCTCGACAGCGTTTCTGAGAAAAGCAGCGT
GTCCCCAGGCTACAACTTCAGGTTTGCCAAGTACTACAAAATGGAAAATGGCAGTGAGTAC
CGCACCCTCCTGAAGGCTTTTGGCATCCGCTTCGACGTGCTGGTATACGGGAATGCTGGCA
AGTTCAACATCATCCCCACCATCATCAGCTCTGTGGCGGCCTTTACTTCTGTGGGAGTGGG
AACTGTTCTCTGTGACATCATCCTGCTCAACTTCCTCAAGGGGCCGACCAGTACAAAGCC
AAGAAGTTTGAGGAGGTGAATGAGACTACGCTGAAAATCGCGGCTTTGACCAACCCAGTGT
ACCCCAGCGACCAGACCACAGCGGAGAAGCAGTCCACCGATTCGGGGGCCTTCTCCATAGG
CCACTAGGGGCTAGAGCGGCCGC (SEQ ID NO:15)

FIGURE 4

| | | | |
|---|---|---|---|
| hP2X3 | 1 | MNCISDFFTYETTKSVVVKSWTIGIINRVVQLL | 33 |
| rP2X3 | 1 | MNCISDFFTYETTKSVVVKSWTIGIINRAVQLL | 33 |
| hP2X3 | 34 | IISYFVGWVFLHEKAYQVRDTAIESSVVTKVKG | 66 |
| rP2X3 | 34 | IISYFVGWVFLHEKAYQVRDTAIESSVVTKVKG | 66 |
| hP2X3 | 67 | SGLYANRVMDVSDYVTPPQGTSVFVIITKMIVT | 99 |
| rP2X3 | 67 | FGRYANRVMDVSDYVTPPQGTSVFVIITKIIVT | 99 |
| hP2X3 | 100 | ENQMGFCPESEEKYRCVSDSQCGPERLPGGGI | 132 |
| rP2X3 | 100 | ENQMGFCPENEEKYRCVSDSQCGPERFPGGGI | 132 |
| hP2X3 | 133 | LTGRCVNYSSVLRTCEIQGWCPTEVDTVETPIM | 165 |
| rP2X3 | 133 | LTGRCVNYSSVLRTCEIQGWCPTEVDTVEMPIM | 165 |
| hP2X3 | 166 | MEAENFTIFIKNSIRFPLFNFEKGNLLPNLTAR | 198 |
| rP2X3 | 166 | MEAENFTIFIKNSIRFPLFNFEKGNLLPNLTDK | 198 |
| hP2X3 | 199 | DMKTCRFHPDKDPFCPILRVGDVVKFAGQDFAK | 231 |
| rP2X3 | 199 | DIKRCRFHPEKAPFCPILRVGDVVKFAGQDFAK | 231 |
| hP2X3 | 232 | LARTGGVLGIKIGWVCDLDKAWDQCIPKYSFTR | 264 |
| rP2X3 | 232 | LARTGGVLGIKIGWVCDLDKAWDQCIPKYSFTR | 264 |
| hP2X3 | 265 | LDSVSEKSSVSPGYNFRFAKYYKMENGSEYRTL | 297 |
| rP2X3 | 265 | LDGVSEKSSVSPGYNFRFAKYYKMENGSEYRTL | 297 |
| hP2X3 | 298 | LKAFGIRFDVLVYGNAGKFNIIPTIISSVAAFT | 330 |
| rP2X3 | 298 | LKAFGIRFDVLVYGNAGKFNIIPTIISSVAAFT | 330 |
| hP2X3 | 331 | SVGVGTVLCDIILLNFLKGADQYKAKKFEEVNE | 363 |
| rP2X3 | 331 | SVGVGTVLCDIILLNFLKGADHYKARKFEEVTE | 363 |
| hP2X3 | 364 | TTLKIAALTNPVYPSDQTTAEKQSTDSGAFSIG | 396 |
| rP2X3 | 364 | TTLKGTASTNPVFASDQATVEKQSTDSGAYSIG | 396 |
| hP2X3 | 397 | H | 397 |
| rP2X3 | 397 | H | 397 |

FIGURE 5

GGCCACGCGTCGACTAGTACGGGGGGGGGGGGGGTGCAGGGCAGCTGGGATTAGGGGTTGAG
GGCTGGGTGTTGGAGGCTGGATCTGGATCCTGCTTTAGTGGAAGTGTCCCTTTAACAGCAAC
TGGCCTGGCCTGGCTCGGGCCCTGCTTTGCCTCCTGTTCAGCTGCGGCTGCAGCTGCCATGC
TGACTCATGTGCCCGCAGCTAGCAGGAGCTGGCAGCATGGGCTCCCCAGGGGCTACAACAGG
CTGGGGGCTTCTGGATTATAAGACGGATAATTATGTGATGACCAGGAACTGGCGGGTGGGCG
CCCTGCAGAGGCTGCTGCAGTTTGGGATCGTGGTCTATGTGGTAGGGTGGGCTCTCCTCGCC
AAAAAAGGCTACCAGGAGCGGG... (SEQ ID NO:27)

FIGURE 6

AATCCGCTTCGACATCCTCGTCACCGGGCAGGCAGGGAAGTTCGGGCTCATCCCCACGGCCG
TCACACTGGGCACCGGGGCAGCTTGGCTGGGCGTGGTCACCTTTTTCTGTGACCTGCTACTG
CTGTATGTGGATAGAGAAGCCCATTTCTACTGGAGGACAAAGTATGAGGAGGCCAAGGCCCC
GAAAGCAACCGCCAACTCTGTGTGGAGGGAGCTGGCCCTTGCATCCCAAGCCCGACTGGCCG
AGTGCCTCAGACGGAGCTCAGCACCTGCACCCACGGCCACTGCTGCTGGGAGTCAGACACAG
ACACCAGGATGGCCCTGTCCAAGTTCTGACACCCACTTGCCAACCCATTCCGGGAGCCTGTA
GCCGTTCCCTGCTGGTTGAGAATT.... (SEQ ID NO:28)

FIGURE 7

.....TCCAGAGCCATGTCCATGGGGAGGTGGGTTTTGAAGGGTGAAGGTGGGAGAGCAGGG
CCCCTGAGGCCTGGGTATCCAAGGAGGGGCACGTGCACCTGATTTTCCTTGGGGCCCAGAGG
AAGCTGATTTCATGGCTGGACAAAGTCACGGAGTAAAGCCAGCAAAGCCACCCTCAAAAAAA
AAAAAAAAAAAAAAAAAAAAAAAAAAAAAAAAAAAAAGTACTAGTCGACGCGTGGCC
(SEQ ID NO:29)

FIGURE 8

GGATCCGCCCCCACCATGTGCCCGCAGCTAGCAGGAGCTGGCAGCATGGGCTCCCCAGGGGC
TACGACAGGCTGGGGGCTTCTGGATTATAAGACGGAGAAGTATGTGATGACCAGGAACTGGC
GGGTGGGCGCCCTGCAGAGGCTGCTGCAGTTTGGGATCGTGGTCTATGTGGTAGGGTGGGCG
CTCCTCGCCAAAAAAGGCTACCAGGAGCGGGACCTGGAACCCCAGTTTTCCATCATCACCAA
ACTCAAAGGGGTTTCCGTCACTCAGATCAAGGAGCTTGGAAACCGGCTGTGGGATGTGGCCG
ACTTCGTGAAGCCACCTCAGGGAGAACGTGTTCTTCTTGGTGACCAACTTCCTTGTGACG
CCAGCCCAAGTTCAGGGCAGATGCCCAGAGCACCCGTCCGTCCCACTGGCTAACTGCTGGGT
CGACGAGGACTGCCCCGAAGGGGAGGGAGGCACACACAGCCACGGTGTAAAAACAGGCCAGT
GTGTGGTGTTCAATGGGACCCACAGGACCTGTGAGATCTGGAGTTGGTGCCCAGTGGAGAGT
GGCGTTGTGCCCTCGAGGCCCCTGCTGGCCCAGGCCCAGAACTTCACACTGTTCATCAAAAA
CACAGTCACCTTCAGCAAGTTCAACTTCTCTAAGTCCAATGCCTTGGAGACCTGGGACCCCA
CCTATTTTAAGCACTGCCGCTATGAACCACAATTCAGCCCCTACTGTCCCGTGTTCCGCATT
GGGGACCTCGTGGCCAAGGCTGGAGGGACCTTCGAGGACCTGGCGTTGCTGGGTGGCTCTGT
AGGCATCAGAGTTCACTGGGATTGTGACCTGGACACCGGGGACTCTGGCTGCTGGCCTCACT
ACTCCTTCCAGCTGCAGGAGAAGAGCTACAACTTCAGGACAGCCACTCACTGGTGGGAGCAA
CCGGGTGTGGAGGCCCGCACCCTGCTCAAGCTCTATGGAATCCGCTTCGACATCCTCGTCAC
CGGGCAGGCAGGGAAGTTCGGGCTCATCCCCACGGCCGTCACACTGGGCACCGGGGCAGCTT
GGCTGGGCGTGGTCACCTTTTTCTGTGACCTGCTACTGCTGTATGTGGATAGAGAAGCCCAT
TTCTACTGGAGGACAAAGTATGAGGAGGCCAAGGCCCCGAAAGCAACCGCCAACTCTGTGTG
GAGGGAGCTGGCCCTTGCATCCCAAGCCCGACTGGCCGAGTGCCTCAGACGGAGCTCAGCAC
CTGCACCCACGGCCACTGCTGCTGGGAGTCAGACACAGACACCAGGATGGCCCTGTCCAAGT
TCTGACACCCACTTGCCAACCCATTCCGGGAGCCTGTAGCCAGGGCTAGAGCGGCCGC
(SEQ ID NO:30)

FIGURE 9

| | | | |
|---|---|---|---|
| hP2X6 | 1 | MCPQLAGAGSMGSPGATTGWGLLDYKTEKYVMT | 33 |
| rP2X6 | 1 | --------MASAVAAALVSWGFLDYKTEKYVMT | 25 |
| hP2X6 | 34 | RNWRVGALQRLLQFGIVVYVVGWALLAKKGYQE | 66 |
| rP2X6 | 26 | RNCWVGISQRLLQLGVVVYVIGWALLAKKGYQE | 58 |
| hP2X6 | 67 | RDLEPQFSIITKLKGVSVTQIKELGNRLWDVAD | 99 |
| rP2X6 | 59 | WDMDPQISVITKLKGVSVTQVKELEKRLWDVAD | 91 |
| hP2X6 | 100 | FVKPPQGENVFFLVTNFLVTPAQVQGRCPEHPS | 132 |
| rP2X6 | 92 | FVRPSQGENVFFLVTNFLVTPAQVQGRCPEHPS | 124 |
| hP2X6 | 133 | VPLANCWVDEDCPEGEGGTHSHGVKTGQCVVFN | 165 |
| rP2X6 | 125 | VPLANCWADEDCPEGEMGTYSHGIKTGQCVAFN | 157 |
| hP2X6 | 166 | GTHRTCEIWSWCPVESGVVPSRPLLAQAQNFTL | 198 |
| rP2X6 | 158 | GTHRTCEIWSWCPVESSAVPRKPLLAQAKNFTL | 190 |
| hP2X6 | 199 | FIKNTVTFSKFNFSKSNALETWDPTYFKHCRYE | 231 |
| rP2X6 | 191 | FIKNTVTFNKFNFSRTNALDTWDNTYFKYCLYD | 223 |
| hP2X6 | 232 | PQFSPYCPVFRIGDLVAKAGGTFEDLALLGGSV | 264 |
| rP2X6 | 224 | SLSSPYCPVFRIGDLVAMTGGDFEDLALLGGAV | 256 |
| hP2X6 | 265 | GIRVHWDCDLDTGDSGCWPHYSFQLQEKSYNFR | 297 |
| rP2X6 | 257 | GINIHWDCNLDTKGSDCSPQYSFQLQERGYNFR | 289 |
| hP2X6 | 298 | TATHWWEQPGVEARTLLKLYGIRFDILVTGQAG | 330 |
| rP2X6 | 290 | TANYWWAASGVESRSLLKLYGIRFDILVTGQAG | 322 |
| hP2X6 | 331 | KFGLIPTAVTLGTGAAWLGVVTFFCDLLLLYVD | 363 |
| rP2X6 | 323 | KFALIPTAITVGTGAAWLGMVTFLCDLLLLYVD | 355 |
| hP2X6 | 364 | REAHFYWRTKYEEAKAPKATANSVWRELALASQ | 396 |
| rP2X6 | 356 | REAGFYWRTKYEEARAPKATTNSA | 379 |
| hP2X6 | 397 | ARLAECLRRSSAPAPTATAAGSQTQTPGWPCPS | 429 |
| hP2X6 | 430 | SDTHLPTHSGSL | 441 |

GAATTCGGCTTTGCGCCACCATGGCGGGCTGCTGCGCCGCGCTGGCGGCCTTC
CTGTTCGAGTACGACACGCCGCGCATCGTGCTCATCCGCAGCCGCAAAGTGGG
GCTCATGAACCGCGCCGTGCAACTGCTCATCCTGGCCTACGTCATCGGGTGGG
TGTTTGTGTGGGAAAAGGGCTACCAGGAAACTGACTCCGTGGTCAGCTCCGTT
ACGACCAAGGTCAAGGGCGTGGCTGTGACCAACACTTCTAAACTTGGATTFCCG
GATCTGGGATGTGGCGGATTATGTGATACCAGCTCAGGAGGAAAACTCCCTCT
TCGTCATGACCAACGTGATCCTCACCATGAACCAGACACAGGGCCTGTGCCCC
GAGATTCCAGATGCGACCACTGTGTGTAAATCAGATGCCAGCTGTACTGCCGG
CTCTGCCGGCACCCACAGCAACGGAGTCTCAACAGGCAGGTGCGTAGCTTTCA
ACGGGTCCGTCAAGACGTGTGAGGTGGCGGCCTGGTGCCCGGTGGAGGATGA
CACACACGTGCCACAACCTGCTTTTTAAAGGCTGCAGAAAACTTCACTCTTTTG
GTTAAGAACAACATCTGGTATCCCAAATTTAATTTCAGCAAGAGGAATATCCTTC
CCAACATCACCACTACTTACCTCAAGTCGTGCATTTATGATGCTAAAACAGATCC
CTTCTGCCCCATATTCCGTCTTGGCAAAATAGTGGAGAACGCAGGACACGGTTT
CCAGGACATGGCCGTGGAGGGAGGCATCATGGGCATCCAGGTCAACTGGGAC
TGCAACCTGGACAGAGCCGCCTCCCTCTGCTTGCCCAGGTACTCCTTCCGCCG
CCTCGATACACGGGACGTTGAGCACAACGTATCTCCTGGCTACAATTTCAGGTT
TGCCAAGTACTACAGAGACCTGGCTGGCAACGAGCAGCGCACGCTCATCAAGG
CCTATGGCATCCGCTTCGACATCATTGTGTTTGGGAAGGCAGGGAAATTTGACA
TCATCCCCACTATGATCAACATCGGCTCTGGCCTGGCACTGCTAGGCATGGCG
ACCGTGCTGTGTGACATCATAGTCCTCTACTGCATGAAGAAAGACTCTACTAT
CGGGAGAAGAAATATAAATATGTGGAAGATTACGAGCAGGGTCTTGCTAGTGA
GCTGGACCAGTGAGGCCTACCAAGCCGAATTC   (SEQ ID NO:1)

*Figure 10*

```
   1 CGGCACGAGG CACCCCGAGA GGAGAAGCGC AGCGCAGTGG CGAGAGGAGC CCCTTGTGGC
  61 AGCAGCACTA CCTGCCCAGA AAAATGCTGG AGGCTGGGCG TGGCCCCAGG CCTGGGGACC
 121 TGTTTTTCCT GTTTCCCGCA GAGTTCCCTG CAGCCCGGTC CAGGTCCAGG CGTGTGCATT
 181 CATGAGTGAG GAACCCGTGC AGGCGCTGAG CATCCTGACC TGGAGAGCAG GGGCTGGTCA
 241 GGGCGATGGC AGCAGACCTG GGCCCCTGGA ATGACACCAT CAATGGCACC TGGGATGGGG
 301 ATGAGCTGGG CTACAGGTGC CGCTTCAACG AGGACTTCAA GTACGTGCTG CTGCCTGTGT
 361 CCTACGGCGT GGTGTGCGTG CTTGGGCTGT GTCTGAACGC CGTGGCGCTC TACATCTTCT
 421 TGTGCCGCCT CAAGACCTGG AATGCGTCCA CCACATATAT GTTCCACCTG GCTGTGTCTG
 481 ATGCACTGTA TGCGGCCTCC CTGCCGCTGC TGGTCTATTA CTACGCCCGC GGCGACCACT
 541 GGCCCTTCAG CACGGTGCTC TGCAAGCTGG TGCGCTTCCT CTTCTACACC AACCTTTACT
 601 GCAGCATCCT CTTCCTCACC TGCATCAGCG TGCACCGGTG TCTGGGCGTC TTACGACCTC
 661 TGCGCTCCCT GCGCTGGGGC CGGGCCCGCT ACGCTCGCCG GGTGGCCGGG GCCGTGTGGG
 721 TGTTGGTGCT GGCCTGCCAG GCCCCGTGC TCTACTTTGT CACCACCAGC GCGCGCGGGG
 781 GCCGCGTAAC CTGCCACGAC ACCTCGGCAC CCGAGCTCTT CAGCCGCTTC GTGGCCTACA
 841 GCTCAGTCAT GCTGGGCCTG CTCTTCGCGG TGCCCTTTGC CGTCATCCTT GTCTGTTACG
 901 TGCTCATGGC TCGGCGACTG CTAAAGCCAG CCTACGGGAC CTCGGGCGGC CTCCCTAGGG
 961 CCAAGCGCAA GTCCGTGCGC ACCATCGCCG TGGTGCTGGC TGTCTTCGCC CTCTGCTTCC
1021 TGCCATTCCA CGTCACCCGC ACCCTCTACT ACTCCTTCCG CTCGCTGGAC CTCAGCTGCC
1081 ACACCCTCAA CGCCATCAAC ATGGCCTACA AGGTTACCCG GCCGCTGGCC AGTGCTAACA
1141 GTTGCCTTGA CCCCGTGCTC TACTTCCTGG CTGGGCAGAG GCTCGTACGC TTTGCCCGAG
1201 ATGCCAAGCC ACCCACTGGC CCCAGCCCTG CCACCCCGGC TCGCCGCAGG CTGGGCCTGC
1261 GCAGATCCGA CAGAACTGAC ATGCAGAGGA TAGGAGATGT GTTGGGCAGC AGTGAGGACT
1321 TCAGGCGGAC AGAGTCCACG CCGGCTGGTA GCGAGAACAC TAAGGACATT CGGCTGTAGG
1381 AGCAGAACAC TTCAGCCTGT GCAGGTTTAT ATTGGGAAGC TGTAGAGGAC CAGGACTTGT
1441 GCAGACGCCA CAGTCTCCCC AGATATGGAC CATCAGTGAC TCATGCTGGA TGACCCCATG
1501 CTCCGTCATT TGACAGGGGC TCAGGATATT CACTCTGTGG TCCAGAGTCA ACTGTTCCCA
1561 TAACCCCTAG TCATCGTTTG TGTGTATAAG TTGGGGGAAT TAAGTTTCAA GAAAGGCAAG
1621 AGCTCAAGGT CAATGACACC CCTGGCCTGA CTCCCATGCA AGTAGCTGGC TGTACTGCCA
1681 AGGTACCTAG GTTGGAGTCC AGCCTAATCA AGTCAAATGG AGAAACAGGC CAGAGAGGA
1741 AGGTGGCTTA CCAAGATCAC ATACCAGAGT CTGGAGCTGA GCTACCTGGG GTGGGGGCCA
1801 AGTCACAGGT TGGCCAGAAA ACCCTGGTAA GTAATGAGGG CTGAGTTTGC ACAGTGGTCT
1861 GGAATGGACT GGGTGCCACG GTGGACTTAG CTCTGAGGAG TACCCCCAGC CAAGAGATG
1921 AACATCTGGG GACTAATATC ATAGACCCAT CTGGAGGCTC CCATGGGCTA GGAGCAGTGT
1981 GAGGCTGTAA CTTATACTAA AGGTTGTGTT GCCTGCTAAA AAAAA   (SEQ ID NO:2)
```

*Figure 11A*

```
                 10         20         30         40         50
       MAADLGPWND TINGTWDGDE LGYRCRFNED FKYVLLPVSY GVVCVLGLCL 60         70         80         90        100
       NAVALYIFLC RLKTWNASTT YMFHLAVSDA LYAASLPLLV YYYARGDHWP 110        120        130        140        150
       FSTVLCKLVR FLFYTNLYCS ILFLTCISVH RCLGVLRPLR SLRWGRARYA 160        170        180        190        200
       RRVAGAVWVL VLACQAPVLY FVTTSARGGR VTCHDTSAPE LFSRFVAYSS 210        220        230        240        250
       VMLGLLFAVP FAVILVCYVL MARRLLKPAY GTSGGLPRAK RKSVRTIAVV 260        270        280        290        300
       LAVFALCFLP FHVTRTLYYS FRSLDLSCHT LNAINMAYKV TRPLASANSC 310        320        330        340        350
       LDPVLYFLAG QRLVRFARDA KPPTGPSPAT PARRRLGLRR SDRTDMQRIG 360        370
       DVLGSSEDFR RTESTPAGSE NTKDIRL    377    (SEQ ID NO:3)
```

*Figure 11B*

GCGCGGTACCCACCATGGCAGCAGACCTGGGCCCCTGGAATGACACCATCAATGGCACCTGG
GATGGGGATGAGCTGGGCTACAGGTGCCGCTTCAACGAGGACTTCAAGTACGTGCTGCTGCCT
GTGTCCTACGGCGTGGTGTGCGTGCTTGGGCTGTGTCTGAACGCCGTGGCGCTCTACATCTTCT
TGTGCCGCCTCAAGACCTGGAATGCGTCCACCACATATATGTTCCACCTGGCTGTGTCTGATGC
ACTGTATGCGGCCTCCCTGCCGCTGCTGGTCTATTACTACGCCCGCGGCGACCACTGGCCCTT
CAGCACGGTGCTCTGCAAGCTGGTGCGCTTCCTCTTCTACACCAACCTTTACTGCAGCATCCTC
TTCCTCACCTGCATCAGCGTGCACCGGTGTCTGGGCGTCTTACGACCTCTGCGCTCCCTGCGCT
GGGGCCGGGCCCGCTACGCTCGCCGGGTGGCCGGGGCCGTGTGGGTGTTGGTGCTGGCCTGCC
AGGCCCCCGTGCTCTACTTTGTCACCACCAGCGCGCGCGGGGGCCGCGTAACCTGCCACGACA
CCTCGGCACCCGAGCTCTTCAGCCGCTTCGTGGCCTACAGCTCAGTCATGCTGGGCCTGCTCTT
CGCGGTGCCCTTTGCCGTCATCCTTGTCTGTTACGTGCTCATGGCTCGGCGACTGCTAAAGCCA
GCCTACGGGACCTCGGGCGGCCTGCCTAGGGCCAAGCGCAAGTCCGTGCGCACCATCGCCGT
GGTGCTGGCTGTCTTCGCCCTCTGCTFCCTGCCATTCCACGTCACCCGCACCCTCTACTACTCC
TTCCGTTCGCTGGACCTCAGCTGCCACACCCTCAACGCCATCAACATGGCCTACAAGGTTACC
CGGCCGCTGGCCAGTGCTAACAGTTGCCTTGACCCCGTGCTCTACTTCCTGGCTGGGCAGAGG
CTCGTACGCTTTGCCCGAGATGCCAAGCCACCCACTGGCCCCAGCCCTGCCACCCCGGCTCGC
TGCAGGCTGGGCCTGCGCAGATCCGACAGAACTGACATGCAGAGGATAGAAGATGTGTTGGGC
AGCAGTGAGGACTCTAGGCGGACAGAGTCCACGCCGGCTGGTAGCGAGAACACTAAGGACATT
CGGCTGTAGTTCTAGACGTCGTAG (SEQ ID NO:4)

Figure 12A

```
                   10         20         30         40         50
            MAADLGPWND TINGTWDGDE LGYRCRFNED FKYVLLPVSY GVVCVLGLCL 60         70         80         90        100
            NAVALYIFLC RLKTWNASTT YMFHLAVSDA LYAASLPLLV YYYARGDHWP 110        120        130        140        150
            FSTVLCKLVR FLFYTNLYCS ILFLTCISVH RCLGVLRPLR SLRWGRARYA 160        170        180        190        200
            RRVAGAVWVL VLACQAPVLY FVTTSARGGR VTCHDTSAPE LFSRFVAYSS 210        220        230        240        250
            VMLGLLFAVP FAVILVCYVL MARRLLKPAY GTSGGLPRAK RKSVRTAVV 260        270        280        290        300
            LAVFALCFLP FHVTRTLYYS FRSLDLSCHT LNAINMAYKV TRPLASANSC 310        320        330        340        350
            LDPVLYFLAG QRLVRFARDA KPPTGPSPAT PARCRLGLRR SDRTDMQRIE

360        370
            DVLGSSEDSR RTESTPAGSE NTKDIRL   377    (SEQ ID NO:5)
```

*Figure 12B*

GAATTCCTGCAGCCCGGGGGGATCCGCCCCACCATGAACTGCATATCCGACTTCTTCACCTAT
GAGACCACCAAGTCGGTGGTTGTGAAGAGCTGGACCATCGGGATCATCAACCGAGTAGTTCAG
CTTCTGATCATCTCCTACTTTGTAGGGTGGGTTTTCTTGCACGAGAAGGCTACCAGGTACGGG
ACACAGCCATTGAGTCCTCGGTGGTAACCAAGGTGAAGGGCTCCGGACTCTACGCCAACAGAG
TCATGGATGTGTCTGATTACGTGACGCCACCTCAGGGCACCTCGGTCTTTGTCATCATCACCAA
GATGATGTTACTGAAAATCAGATGCAAGGATTCTGCCCAGAGAGTGAGGAGAAATACCGCTG
TGTATCAGACAGCCAGTGCGGGCCTGAGCGCTTGCCAGGTGGGGGGATCCTCACTGGCCGCTG
CGTGAACTACAGCTCTGTGCTCCGGACCTGTGAGATCCAGGGCTGGTGCCCCACGGAGGTGGA
CACAGTGGAAACGCCCATCATGATGGAAGCTGAGAACTTCACTATTTCATCAAGAACAGCAT
CCGTTTCCCCCTCTTCAACTTTGAGAAGGGAAACTCCTTCCCAACCTGACAGCCAGGGACAT
GAAGACCTGCCGCTTCCACCCGGACAAGGACCCTTTCTGCCCCATCTTGCGGGTAGGGACGT
GGTCAAGTTTGCGGGACAGGATTTTGCCAAACTGGCGCGCACGGGGGAGTTCTGGGCATTAA
GATCGGCTGGGTGTGCGACTTGGACAAGGCCTGGGACCAGTGCATCCCCAAATACTCCTTCAC
CCGGCTCGACAGCGTTTCTGAGAAAAGCAGCGTGTCCCCAGGCTACAACTTCAGGTTTGCCAA
GTACTACAAAATGGAAAATGGCAGTGAGTACCGCACCCTCCTGAAGGCTTTTGGCATCCGCTT
CGACGTGCTGGTATACGGGAATGCTGGCAAGTTCAACATCATCCCCACCATCATCAGCTCTGT
GGCGGCCTTTACTTCTGTGGGAGTGGGAACTGTTCTCTGTGACATCATCCTGCTCAACTTCCTC
AAGGGGGCCGACCAGTACAAAGCCAAGAAGTTTGAGGAGGTGAATGAGACTACGCTGAAAATC
GCGGCTTTGACCAACCCAGTGTACCCCAGCGACCAGACCACAGCGGAGAAGCAGTCCACCGA
TTCGGGGGCCTTCTCCATAGGCCACTAGGGGCTAGAGCGGCCGC (SEQ ID NO:5)

Figure 13

CTACTACTACTAGGCCACGCGTCGACTAGTACGGGGGGGGGGGGGGACCGGGGACGACCAC
CACCTACCTCCTCAGGCTGCGGCCTCGCGAGGGCCCCGGCGCGAGAGGACCCCCCTCTCCTG
AGGCCACCACTGGGCCCCCTTCTGAGTGTCCCCTGAGCACTCTCTCAGCATGAACTGCATATC
CGACTTCTTCACCTATGAGACCACCAAGTCGGTGGTTGTGAAAAGCTGGACCATCGGGATCAT
CAACCGAGTAGTTCAGCTTCTGATCATCTCCTACTTTGTAGGGTGGGTTTTCTIGCACGAGAAG
GCTTACCAGGTACGGGACACAGCCATTAAGTCCTCGGTGGTAACCAAGGTGAAGGGCTCCGGA
CTCTACACCAACAGAGTCATGGATGTGTCTGATTACGTGACGCCACCTCAGGGCACCTCGGTC
TTTGTCATCATCACCAAGATGATTGTTACTGAAAATCAGATGCAAGGATTCTGCCCAGAGAGTG
AGGAGAAATACCGCTGTGTATCAGACAGCCAGTGCGGGCCTGAGCGCTTGCCAGGGATCCTCA
CTGGCCGCTGCGTGAACTACAGCTCTGCGCTCCGGACCTGTGAGATCCAGGGCTGGTGCCCCA
CGGAGGTGGACACAGTGGAAACGCCCATCATGATGGAAGCTGAGAACTTCACTATTTTCATCA
AGAACAGCATCCGTTTCCCCCTCTTCAACTTTGAGAAGGGAAACCTCCTTCTCCAACCTGACAG
CCAGGGACATGAAGACCTGCCGCTTCCACCCGGACAAGGACCCTTCTCACCCCATCTTGCGGG
TAGGGACGTGGTCAAGTTTGCGGGGCAGGATTTTGCCAAACTGGCGCGCACGGGGGAGTTC
TGGGCATTAAGATCGGCTGGGTGTGCGACTTGGACAAGGCCTGGGACCAGTGCATCCCCAAAT
ACTCCTTCACCCGGCTCGACAGCGTTTCTGAGAAAAGCAGCGTGTCCCAGGCTACAACTTCA
GGTTTGCCAAGTACTACAAAATGGAAAATGGCAGTGAGTACCGCACCCTCCTGAAGGCTTTTG
GCATCCGCTTCGACGTGCTGGTATACGGGAATGCTGGCAAGTTCAACATCATCCCCACCATCA
TCAGCTCTGTGGCGGCCTTTACTTCTGTGGGAGTGGGAACTGTTCTCTGTGACATCATCCTGCT
CAACTTCCTCAGGGGGGCCGACCAGTACAAAGCCAAGAAGTTGAGGAGGTGAATGAGACTAC
ACTGAAAATCG (SEQ ID NO:23)

*Figure 14*

ACCACAGTGGAGAAGCAGTCCACCGATTCGGGGGCCTTCTCCATAGGCCACTAGGGCCTCTTT
CCAGGGCCCCACACTCACAAAGGCTCCAGGCCTCCCCACAGAGGACCCTGCCTGAGCAAGGG
GGCATGGGAGGGAAGAGGGGCTCTCATTTCTGCTGCTCATTCCATGAGCATAGCTGGGACCCA
AGTGTCTGGGCCTCCGACTGCTCCAGCAGACAGGCAGTGCTCCCTGCTGAGACCCCAGTCTCA
CCTTCACTCCTTGCCTGGCCCCATCTGCTTCCTAGGACCCCTGGGGCAGGAGCACCTGAGCCA
TCCCCTTCCCAAAGAGTAGAGATTATAATGTAGGACAGATGGCCACAAGGGCCTACCAAGTGC
CAGGCACTTTCACACACGTTATCTCATTTAATCCTTAGAATAATCCTATGAGGTAGATATTAGTT
TCCCTTGTTTTGAAGATAAACCAAGGCTCAGAGAGACTGAGTCATTTGCCCCAGGCCAGATAG
CCAGGATGTGAGAGAGCTGGGATTTGAACGTCCGTCTGACTAACTCCATCGCCCACACCCCAT
GAGAGAAGATGAACTCCCAGGGTCCATCAGCCCTGCTGCTTCAGCCGCCTCCACCCTGACGGT
GATTCGGTTAATAAAGAGTAAGCCCCAAAAAAAAAAAAAAAAAAAAAAAAAAAAAGTACTAGT
CGACGCGTGGCC (SEQ ID NO:24)

FIG. 15

SEQUENCE LISTING

<160> NUMBER OF SEQ ID NOS: 32

<210> SEQ ID NO 1
<211> LENGTH: 229
<212> TYPE: DNA

-continued

```
<213> ORGANISM: Artificial Sequence
<220> FEATURE:
<223> OTHER INFORMATION: Synthetic Oligonucleotide for PCR
<220> FEATURE:
<221> NAME/KEY: modified_base
<222> LOCATION: (103)...(103)
<223> OTHER INFORMATION: n = a or g or c or t/u, unknown, or other
<220> FEATURE:
<221> NAME/KEY: modified_base
<222> LOCATION: (106)...(106)
<223> OTHER INFORMATION: n = a or g or c or t/u, unknown, or other

<400> SEQUENCE: 1
cccgaatcgg tggactgctt ctccactgtg gtctggtcgc tggggtacac tgggttggtc      60
aaagccgcga ttttcagtgt agtctcattc acntgnaggc gaaagagctg gtgttgtcaa    120
gttctgacta tgggcaatgt cctctttttgt gaccccattt gacagactca gcagtgggcg    180
cccatgacct agtcatgagg ggagccagga catctgtgtg atcccaagg                  229

<210> SEQ ID NO 2
<211> LENGTH: 20
<212> TYPE: DNA
<213> ORGANISM: Artificial Sequence
<220> FEATURE:
<223> OTHER INFORMATION: Sequencing Primer

<400> SEQUENCE: 2
tttaccaacc cagtgtaccc                                                   20

<210> SEQ ID NO 3
<211> LENGTH: 20
<212> TYPE: DNA
<213> ORGANISM: Artificial Sequence
<220> FEATURE:
<223> OTHER INFORMATION: Sequencing Primer

<400> SEQUENCE: 3
accacagtgg agaagcagtc                                                   20

<210> SEQ ID NO 4
<211> LENGTH: 20
<212> TYPE: DNA
<213> ORGANISM: Artificial Sequence
<220> FEATURE:
<223> OTHER INFORMATION: Sequencing Primer

<400> SEQUENCE: 4
gaatcggtgg actgcttctc                                                   20

<210> SEQ ID NO 5
<211> LENGTH: 23
<212> TYPE: DNA
<213> ORGANISM: Artificial Sequence
<220> FEATURE:
<223> OTHER INFORMATION: Sequencing Primer

<400> SEQUENCE: 5
cgattttcag tgtagtctca ttc                                               23

<210> SEQ ID NO 6
<211> LENGTH: 20
<212> TYPE: DNA
<213> ORGANISM: Artificial Sequence
<220> FEATURE:
<223> OTHER INFORMATION: Sequencing Primer

<400> SEQUENCE: 6
```

```
ggggtacact gggttggtaa                                            20

<210> SEQ ID NO 7
<211> LENGTH: 48
<212> TYPE: DNA
<213> ORGANISM: Artificial Sequence
<220> FEATURE:
<223> OTHER INFORMATION: 5'RACE Anchor Primer
<220> FEATURE:
<221> NAME/KEY: modified_base
<222> LOCATION: (36)...(37)
<223> OTHER INFORMATION: n = a or g or c or t/u, unknown, or other
<220> FEATURE:
<221> NAME/KEY: modified_base
<222> LOCATION: (41)...(42)
<223> OTHER INFORMATION: n = a or g or c or t/u, unknown, or other
<220> FEATURE:
<221> NAME/KEY: modified_base
<222> LOCATION: (46)...(47)
<223> OTHER INFORMATION: n = a or g or c or t/u, unknown, or other

<400> SEQUENCE: 7
cuacuacuac uaggccacgc gtcgactagt acgggnnggg nngggnng             48

<210> SEQ ID NO 8
<211> LENGTH: 32
<212> TYPE: DNA
<213> ORGANISM: Artificial Sequence
<220> FEATURE:
<223> OTHER INFORMATION: Universal Adapter Primer

<400> SEQUENCE: 8
cuacuacuac uaggccacgc gtcgactagt ac                              32

<210> SEQ ID NO 9
<211> LENGTH: 37
<212> TYPE: DNA
<213> ORGANISM: Artificial Sequence
<220> FEATURE:
<223> OTHER INFORMATION: Adapter Sequencing Primer

<400> SEQUENCE: 9
ggccacgcgt cgactagtac tttttttttt ttttttt                         37

<210> SEQ ID NO 10
<211> LENGTH: 20
<212> TYPE: DNA
<213> ORGANISM: Artificial Sequence
<220> FEATURE:
<223> OTHER INFORMATION: Abridged Universal Adapter Sequencing Primer

<400> SEQUENCE: 10
ggccacgcgt cgactagtac                                            20

<210> SEQ ID NO 11
<211> LENGTH: 25
<212> TYPE: DNA
<213> ORGANISM: Artificial Sequence
<220> FEATURE:
<223> OTHER INFORMATION: Sequencing Primer

<400> SEQUENCE: 11
caccatgaac tgcatatccg acttc                                      25

<210> SEQ ID NO 12
<211> LENGTH: 21
<212> TYPE: DNA
```

<213> ORGANISM: Artificial Sequence
<220> FEATURE:
<223> OTHER INFORMATION: Sequencing Primer

<400> SEQUENCE: 12
ctagtggcct atggagaagg c                                             21

<210> SEQ ID NO 13
<211> LENGTH: 1272
<212> TYPE: DNA
<213> ORGANISM: Artificial Sequence
<220> FEATURE:
<223> OTHER INFORMATION: Sequencing Primer

<400> SEQUENCE: 13

| ctactactac taggccacgc gtcgactagt acggggggg ggggggacc gggacgacc | 60 |
| accacctacc tcctcaggct gcggcctcgc gagggcccg gcgcgagagg accccctct | 120 |
| cctgaggcca ccactgggcc cccttctgag tgtccctga gcactctctc agcatgaact | 180 |
| gcatatccga cttcttcacc tatgagacca ccaagtcgt ggttgtgaaa agctggacca | 240 |
| tcgggatcat caaccgagta gttcagcttc tgatcatctc ctactttgta gggtgggttt | 300 |
| tcttgcacga gaaggcttac caggtacggg acacagccat taagtcctcg gtggtaacca | 360 |
| aggtgaaggg ctccggactc tacaccaaca gagtcatgga tgtgtctgat tacgtgacgc | 420 |
| cacctcaggg cacctcggtc tttgtcatca tcaccaagat gattgttact gaaaatcaga | 480 |
| tgcaaggatt ctgcccagag agtgaggaga aataccgctg tgtatcagac agccagtgcg | 540 |
| ggcctgagcg cttgccaggg atcctcactg gccgctgcgt gaactacagc tctgcgctcc | 600 |
| ggacctgtga gatccaggc tggtgcccca cggaggtgga cacagtggaa acgcccatca | 660 |
| tgatggaagc tgagaacttc actattttca tcaagaacag catccgtttc cccctcttca | 720 |
| actttgagaa gggaaacctc cttcccaacc tgacagccag ggacatgaag acctgccgct | 780 |
| tccacccgga caaggaccct ttctacccca tcttgcgggt aggggacgtg gtcaagtttg | 840 |
| cggggcagga ttttgccaaa ctggcgcgca cggggggagt tctgggcatt aagatcggct | 900 |
| gggtgtgcga cttggacaag gcctgggacc agtgcatccc caaatactcc ttcacccggc | 960 |
| tcgacagcgt ttctgagaaa agcagcgtgt ccccaggcta caacttcagg tttgccaagt | 1020 |
| actacaaaat ggaaatggc agtgagtacc gcaccctcct gaaggctttt ggcatccgct | 1080 |
| tcgacgtgct ggtatacggg aatgctggca agttcaacat catccccacc atcatcagct | 1140 |
| ctgtggcggc cttacttct gtgggagtgg gaactgttct ctgtgacatc atcctgctca | 1200 |
| acttcctcag gggggccgac cagtacaaag ccaagaagtt tgaggaggtg aatgagacta | 1260 |
| cactgaaaat cg | 1272 |

<210> SEQ ID NO 14
<211> LENGTH: 706
<212> TYPE: DNA
<213> ORGANISM: Artificial Sequence
<220> FEATURE:
<223> OTHER INFORMATION: Sequencing Primer

<400> SEQUENCE: 14

| accacagtgg agaagcagtc caccgattcg ggggccttct ccataggcca ctagggcctc | 60 |
| tttccagggc cccacactca caaaggctcc aggcctcccc acagaggacc ctgcctgagc | 120 |
| aaggggcat gggagggaag agggctctc atttctgctc ctcattccat gagcatagct | 180 |
| gggacccaag tgtctgggcc tccgactgct ccagcagaca ggcagtgctc cctgctgaga | 240 |

-continued

```
ccccagtctc accttcactc cttgcctggc cccatctgct tcctaggacc cctggggcag    300
gagcacctga gccatcccct tcccaaagag tagagattat aatgtaggac agatggccac    360
aagggcctac caagtgccag gcactttcac acacgttatc tcatttaatc cttagaataa    420
tcctatgagg tagatattag tttcccttgt tttgaagata aaccaaggct cagagagact    480
gagtcatttg ccccaggcca gatagccagg atgtgagaga gctggatttt gaacgtccgt    540
ctgactaact ccatcgccca caccccatga gagaagatga actcccaggg tccatcagcc    600
ctgctgcttc agccgcctcc accctgacgg tgattcggtt aataaagagt aagcccaaa    660 aaaaaaaaaa aaaaaaaaa aaaaagtac tagtcgacgc gtggcc          706
```

<210> SEQ ID NO 15
<211> LENGTH: 1243
<212> TYPE: DNA
<213> ORGANISM: Homo sapiens

<400> SEQUENCE: 15

```
gaattcctgc agcccggggg gatccgcccc accatgaact gcatatccga cttcttcacc     60
tatgagacca ccaagtcggt ggttgtgaag agctggacca tcgggatcat caaccgagta    120
gttcagcttc tgatcatctc ctactttgta gggtgggttt tcttgcacga gaaggcttac    180
caggtacggg acacagccat tgagtcctcg gtggtaacca aggtgaaggg ctccggactc    240
tacgccaaca gagtcatgga tgtgtctgat tacgtgacgc cacctcaggg cacctcggtc    300
tttgtcatca tcaccaagat gattgttact gaaaatcaga tgcaaggatt ctgcccagag    360
agtgaggaga ataccgctg tgtatcagac agccagtgcg ggcctgagcg cttgccaggt    420 gggggggatcc tcactggccg ctgcgtgaac tacagctctg tgctccggac ctgtgagatc    480
cagggctggt gccccacgga ggtggacaca gtggaaacgc ccatcatgat ggaagctgag    540
aacttcacta ttttcatcaa gaacagcatc cgtttccccc tcttcaactt tgagaaggga    600
aacctccttc caaacctgac agccaggggac atgaagacct gccgcttcca cccggacaag    660
gaccctttct gccccatctt gcgggtaggg gacgtggtca gtttgcggg acaggatttt    720 gccaaactgg cgcgcacggg gggagttctg ggcattaaga tcggctgggt gtgcgacttg    780
gacaaggcct gggaccagtg catccccaaa tactccttca cccggctcga cagcgttttct    840 gagaaaagca gcgtgtcccc aggctacaac ttcaggtttg ccaagtacta caaaatggaa    900
aatggcagtg agtaccgcac cctcctgaag gctttttggca tccgcttcga cgtgctggta    960
tacgggaatg ctggcaagtt caacatcatc cccaccatca tcagctctgt ggcggccttt   1020
acttctgtgg gagtgggaac tgttctctgt gacatcatcc tgctcaactt cctcaagggg   1080
gccgaccagt acaaagccaa gaagtttgag gaggtgaatg agactacgct gaaaatcgcg   1140
gctttgacca acccagtgta ccccagcgac cagaccacga cggagaagca gtccaccgat   1200
tcgggggcct tctccatagg ccactagggg ctagagcggc cgc                    1243
```

<210> SEQ ID NO 16
<211> LENGTH: 397
<212> TYPE: PRT
<213> ORGANISM: Homo sapiens

<400> SEQUENCE: 16

```
Met Asn Cys Ile Ser Asp Phe Phe Thr Tyr Glu Thr Thr Lys Ser Val
  1               5                  10                  15

Val Val Lys Ser Trp Thr Ile Gly Ile Ile Asn Arg Val Val Gln Leu
```

|   |   |   | 20  |   |   | 25  |   |   | 30  |   |   |
|---|---|---|---|---|---|---|---|---|---|---|---|

Leu Ile Ile Ser Tyr Phe Val Gly Trp Val Phe Leu His Glu Lys Ala
       35              40              45

Tyr Gln Val Arg Asp Thr Ala Ile Glu Ser Ser Val Thr Lys Val
50              55              60

Lys Gly Ser Gly Leu Tyr Ala Asn Arg Val Met Asp Val Ser Asp Tyr
65              70              75              80

Val Thr Pro Pro Gln Gly Thr Ser Val Phe Val Ile Ile Thr Lys Met
             85               90              95

Ile Val Thr Glu Asn Gln Met Gln Gly Phe Cys Pro Glu Ser Glu Glu
           100              105            110

Lys Tyr Arg Cys Val Ser Asp Ser Gln Cys Gly Pro Glu Arg Leu Pro
           115              120            125

Gly Gly Gly Ile Leu Thr Gly Arg Cys Val Asn Tyr Ser Ser Val Leu
           130              135            140

Arg Thr Cys Glu Ile Gln Gly Trp Cys Pro Thr Glu Val Asp Thr Val
145              150              155            160

Glu Thr Pro Ile Met Met Glu Ala Glu Asn Phe Thr Ile Phe Ile Lys
           165              170            175

Asn Ser Ile Arg Phe Pro Leu Phe Asn Phe Glu Lys Gly Asn Leu Leu
           180              185            190

Pro Asn Leu Thr Ala Arg Asp Met Lys Thr Cys Arg Phe His Pro Asp
           195              200            205

Lys Asp Pro Phe Cys Pro Ile Leu Arg Val Gly Asp Val Val Lys Phe
210              215              220

Ala Gly Gln Asp Phe Ala Lys Leu Ala Arg Thr Gly Gly Val Leu Gly
225              230              235            240

Ile Lys Ile Gly Trp Val Cys Asp Leu Asp Lys Ala Trp Asp Gln Cys
           245              250            255

Ile Pro Lys Tyr Ser Phe Thr Arg Leu Asp Ser Val Ser Glu Lys Ser
           260              265            270

Ser Val Ser Pro Gly Tyr Asn Phe Arg Phe Ala Lys Tyr Tyr Lys Met
           275              280            285

Glu Asn Gly Ser Glu Tyr Arg Thr Leu Leu Lys Ala Phe Gly Ile Arg
           290              295            300

Phe Asp Val Leu Val Tyr Gly Asn Ala Gly Lys Phe Asn Ile Ile Pro
305              310              315            320

Thr Ile Ile Ser Ser Val Ala Ala Phe Thr Ser Val Gly Val Gly Thr
           325              330            335

Val Leu Cys Asp Ile Ile Leu Leu Asn Phe Leu Lys Gly Ala Asp Gln
           340              345            350

Tyr Lys Ala Lys Lys Phe Glu Glu Val Asn Glu Thr Thr Leu Lys Ile
           355              360            365

Ala Ala Leu Thr Asn Pro Val Tyr Pro Ser Asp Gln Thr Thr Ala Glu
           370              375            380

Lys Gln Ser Thr Asp Ser Gly Ala Phe Ser Ile Gly His
385              390              395

<210> SEQ ID NO 17
<211> LENGTH: 397
<212> TYPE: PRT
<213> ORGANISM: Rattus rattus

<400> SEQUENCE: 17

```
Met Asn Cys Ile Ser Asp Phe Phe Thr Tyr Glu Thr Thr Lys Ser Val
 1               5                  10                  15

Val Val Lys Ser Trp Thr Ile Gly Ile Ile Asn Arg Ala Val Gln Leu
             20                  25                  30

Leu Ile Ile Ser Tyr Phe Val Gly Trp Val Phe Leu His Glu Lys Ala
         35                  40                  45

Tyr Gln Val Arg Asp Thr Ala Ile Glu Ser Ser Val Thr Lys Val
 50                  55                  60

Lys Gly Phe Gly Arg Tyr Ala Asn Arg Val Met Asp Val Ser Asp Tyr
 65                  70                  75                  80

Val Thr Pro Pro Gln Gly Thr Ser Val Phe Val Ile Ile Thr Lys Ile
                 85                  90                  95

Ile Val Thr Glu Asn Gln Met Gln Gly Phe Cys Pro Glu Asn Glu Glu
             100                 105                 110

Lys Tyr Arg Cys Val Ser Asp Ser Gln Cys Gly Pro Glu Arg Phe Pro
             115                 120                 125

Gly Gly Gly Ile Leu Thr Gly Arg Cys Val Asn Tyr Ser Ser Val Leu
 130                 135                 140

Arg Thr Cys Glu Ile Gln Gly Trp Cys Pro Thr Glu Val Asp Thr Val
145                 150                 155                 160

Glu Met Pro Ile Met Met Glu Ala Glu Asn Phe Thr Ile Phe Ile Lys
                 165                 170                 175

Asn Ser Ile Arg Phe Pro Leu Phe Asn Phe Glu Lys Gly Asn Leu Leu
             180                 185                 190

Pro Asn Leu Thr Asp Lys Asp Ile Lys Arg Cys Arg Phe His Pro Glu
             195                 200                 205

Lys Ala Pro Phe Cys Pro Ile Leu Arg Val Gly Asp Val Val Lys Phe
 210                 215                 220

Ala Gly Gln Asp Phe Ala Lys Leu Ala Arg Thr Gly Gly Val Leu Gly
225                 230                 235                 240

Ile Lys Ile Gly Trp Val Cys Asp Leu Asp Lys Ala Trp Asp Gln Cys
             245                 250                 255

Ile Pro Lys Tyr Ser Phe Thr Arg Leu Asp Gly Val Ser Glu Lys Ser
             260                 265                 270

Ser Val Ser Pro Gly Tyr Asn Phe Arg Phe Ala Lys Tyr Tyr Lys Met
 275                 280                 285

Glu Asn Gly Ser Glu Tyr Arg Thr Leu Leu Lys Ala Phe Gly Ile Arg
290                 295                 300

Phe Asp Val Leu Val Tyr Gly Asn Ala Gly Lys Phe Asn Ile Ile Pro
305                 310                 315                 320

Thr Ile Ile Ser Ser Val Ala Ala Phe Thr Ser Val Gly Val Gly Thr
             325                 330                 335

Val Leu Cys Asp Ile Ile Leu Leu Asn Phe Leu Lys Gly Ala Asp His
             340                 345                 350

Tyr Lys Ala Arg Lys Phe Glu Glu Val Thr Glu Thr Thr Leu Lys Gly
             355                 360                 365

Thr Ala Ser Thr Asn Pro Val Phe Ala Ser Asp Gln Ala Thr Val Glu
             370                 375                 380

Lys Gln Ser Thr Asp Ser Gly Ala Tyr Ser Ile Gly His
385                 390                 395

<210> SEQ ID NO 18
<211> LENGTH: 94
<212> TYPE: DNA
```

<213> ORGANISM: Homo sapiens

<400> SEQUENCE: 18
gacagccact cactggtggg agcaaccggg tgtggaggcc cgcaccctgc tcaagctcta    60
tggaatccgc ttcgacatcc tcgtcaccgg gcag    94

<210> SEQ ID NO 19
<211> LENGTH: 18
<212> TYPE: DNA
<213> ORGANISM: Artificial Sequence
<220> FEATURE:
<223> OTHER INFORMATION: Sequencing Primer

<400> SEQUENCE: 19
gtgacgagga tgtcgaag    18

<210> SEQ ID NO 20
<211> LENGTH: 20
<212> TYPE: DNA
<213> ORGANISM: Artificial Sequence
<220> FEATURE:
<223> OTHER INFORMATION: Sequencing Primer

<400> SEQUENCE: 20
agagcttgag cagggtgcgg    20

<210> SEQ ID NO 21
<211> LENGTH: 20
<212> TYPE: DNA
<213> ORGANISM: Artificial Sequence
<220> FEATURE:
<223> OTHER INFORMATION: Sequencing Primer

<400> SEQUENCE: 21
tgctcccacc agtgagtggc    20

<210> SEQ ID NO 22
<211> LENGTH: 20
<212> TYPE: DNA
<213> ORGANISM: Artificial Sequence
<220> FEATURE:
<223> OTHER INFORMATION: Sequencing Primer

<400> SEQUENCE: 22
caccctgctc aagctctatg    20

<210> SEQ ID NO 23
<211> LENGTH: 20
<212> TYPE: DNA
<213> ORGANISM: Artificial Sequence
<220> FEATURE:
<223> OTHER INFORMATION: Sequencing Primer

<400> SEQUENCE: 23
aatccgcttc gacatcctcg    20

<210> SEQ ID NO 24
<211> LENGTH: 20
<212> TYPE: DNA
<213> ORGANISM: Artificial Sequence
<220> FEATURE:
<223> OTHER INFORMATION: Abridged Universal Adapter Sequencing Primer

<400> SEQUENCE: 24
ggccacgcgt cgactagtac    20

<210> SEQ ID NO 25
<211> LENGTH: 30
<212> TYPE: DNA
<213> ORGANISM: Artificial Sequence
<220> FEATURE:
<223> OTHER INFORMATION: Sequencing Primer

<400> SEQUENCE: 25
ccaccatgtg cccgcagcta gcaggagctg                                30

<210> SEQ ID NO 26
<211> LENGTH: 26
<212> TYPE: DNA
<213> ORGANISM: Artificial Sequence
<220> FEATURE:
<223> OTHER INFORMATION: Sequencing Primer

<400> SEQUENCE: 26
ggctacaggc tcccggaatg ggttgg                                    26

<210> SEQ ID NO 27
<211> LENGTH: 394
<212> TYPE: DNA
<213> ORGANISM: Artificial Sequence
<220> FEATURE:
<223> OTHER INFORMATION: Universal Amplification Sequencing Primer

<400> SEQUENCE: 27
ggccacgcgt cgactagtac gggggggggg ggggtgcagg gcagctggga ttaggggttg    60
agggctgggt gttggaggct ggatctggat cctgctttag tggaagtgtc cctttaacag   120
caactggcct ggcctggctc gggccctgct ttgcctcctg ttcagctgcg gctgcagctg   180
ccatgctgac tcatgtgccc gcagctagca ggagctggca gcatgggctc ccagggggct   240
acaacaggct gggggcttct ggattataag acggataatt atgtgatgac caggaactgg   300
cgggtgggcg ccctgcagag gctgctgcag tttgggatcg tggtctatgt ggtagggtgg   360
gctctcctcg ccaaaaaagg ctaccaggag cggg                              394

<210> SEQ ID NO 28
<211> LENGTH: 396
<212> TYPE: DNA
<213> ORGANISM: Artificial Sequence
<220> FEATURE:
<223> OTHER INFORMATION: Sequencing Primer

<400> SEQUENCE: 28
aatccgcttc gacatcctcg tcaccgggca ggcagggaag ttcgggctca tccccacggc    60
cgtcacactg ggcaccgggg cagcttggct gggcgtggtc acctttttct gtgacctgct   120
actgctgtat gtggatagag aagcccattt ctactggagg acaaagtatg aggaggccaa   180
ggccccgaaa gcaaccgcca actctgtgtg gagggagctg gcccttgcat cccaagcccg   240
actggccgag tgcctcagac ggagctcagc acctgcaccc acggccactg ctgctgggag   300
tcagacacag acaccaggat ggccctgtcc aagttctgac acccacttgc caacccattc   360
cgggagcctg tagccgttcc ctgctggttg agaatt                            396

<210> SEQ ID NO 29
<211> LENGTH: 237
<212> TYPE: DNA
<213> ORGANISM: Artificial Sequence
<220> FEATURE:

<223> OTHER INFORMATION: Sequencing Primer

<400> SEQUENCE: 29

| | | | | |
|---|---|---|---|---|
| tccagagcca | tgtccatggg | gaggtgggtt | ttgaagggtg | aaggtgggag agcagggccc | 60 |
| ctgaggcctg | ggtatccaag | gaggggcacg | tgcacctgat | tttccttggg gcccagagga | 120 |
| agctgatttc | atggctggac | aaagtcacgg | agtaaagcca | gcaaagccac cctcaaaaaa | 180 |
| aaaaaaaaaa | aaaaaaaaaa | aaaaaaaaaa | aaaaaagta | ctagtcgacg cgtggcc | 237 |

<210> SEQ ID NO 30
<211> LENGTH: 1360
<212> TYPE: DNA
<213> ORGANISM: Artificial Sequence
<220> FEATURE:
<223> OTHER INFORMATION: Sequencing Primer (polynucleotide)

<400> SEQUENCE: 30

| | | | | | |
|---|---|---|---|---|---|
| ggatccgccc | ccaccatgtg | cccgcagcta | gcaggagctg | gcagcatggg ctccccaggg | 60 |
| gctacgacag | gctgggggct | tctggattat | aagacggaga | agtatgtgat gaccaggaac | 120 |
| tggcgggtgg | gcgccctgca | gaggctgctg | cagtttggga | tcgtggtcta tgtggtaggg | 180 |
| tgggcgctcc | tcgccaaaaa | aggctaccag | gagcgggacc | tggaacccca gttttccatc | 240 |
| atcaccaaac | tcaaagggt | ttccgtcact | cagatcaag | agcttggaaa ccggctgtgg | 300 |
| gatgtggccg | acttcgtgaa | gccacctcag | ggagagaacg | tgttcttctt ggtgaccaac | 360 |
| ttccttgtga | cgccagccca | agttcagggc | agatgcccag | agcaccgtc cgtcccactg | 420 |
| gctaactgct | gggtcgacga | ggactgcccc | gaagggagg | gaggcacaca cagccacggt | 480 |
| gtaaaaacag | gccagtgtgt | ggtgttcaat | gggacccaca | ggacctgtga gatctggagt | 540 |
| tggtgcccag | tggagagtgg | cgttgtgccc | tcgaggcccc | tgctggccca ggcccagaac | 600 |
| ttcacactgt | tcatcaaaaa | cacagtcacc | ttcagcaagt | tcaacttctc taagtccaat | 660 |
| gccttggaga | cctgggaccc | cacctatttt | aagcactgcc | gctatgaacc acaattcagc | 720 |
| ccctactgtc | ccgtgttccg | cattggggac | ctcgtggcca | aggctggagg gaccttcgag | 780 |
| gacctggcgt | tgctgggtgg | ctctgtaggc | atcagagttc | actgggattg tgacctggac | 840 |
| accggggact | ctggctgctg | gcctcactac | tccttccagc | tgcaggagaa gagctacaac | 900 |
| ttcaggacag | ccactcactg | gtgggagcaa | ccgggtgtgg | aggcccgcac cctgctcaag | 960 |
| ctctatggaa | tccgcttcga | catcctcgtc | accgggcagg | cagggaagtt cgggctcatc | 1020 |
| cccacggccg | tcacactggg | caccgggca | gcttggctgg | gcgtggtcac ctttttctgt | 1080 |
| gacctgctac | tgctgtatgt | ggatagaaa | gcccatttct | actggaggac aaagtatgag | 1140 |
| gaggccaagg | ccccgaaagc | aaccgccaac | tctgtgtgga | gggagctggc ccttgcatcc | 1200 |
| caagcccgac | tggccgagtg | cctcagacgg | agctcagcac | ctgcacccac ggccactgct | 1260 |
| gctgggagtc | agacacagac | accaggatgg | ccctgtccaa | gttctgacac ccacttgcca | 1320 |
| acccattccg | ggagcctgta | gccagggcta | gagcggccgc | | 1360 |

<210> SEQ ID NO 31
<211> LENGTH: 441
<212> TYPE: PRT
<213> ORGANISM: Homo sapiens (polypeptide)

<400> SEQUENCE: 31

Met Cys Pro Gln Leu Ala Gly Ala Gly Ser Met Gly Ser Pro Gly Ala
1               5                   10                  15

-continued

```
Thr Thr Gly Trp Gly Leu Leu Asp Tyr Lys Thr Glu Lys Tyr Val Met
            20                  25                  30

Thr Arg Asn Trp Arg Val Gly Ala Leu Gln Arg Leu Leu Gln Phe Gly
            35                  40                  45

Ile Val Val Tyr Val Val Gly Trp Ala Leu Leu Ala Lys Lys Gly Tyr
50                  55                  60

Gln Glu Arg Asp Leu Glu Pro Gln Phe Ser Ile Ile Thr Lys Leu Lys
65                  70                  75                  80

Gly Val Ser Val Thr Gln Ile Lys Glu Leu Gly Asn Arg Leu Trp Asp
                85                  90                  95

Val Ala Asp Phe Val Lys Pro Gln Gly Glu Asn Val Phe Phe Leu
                100                 105                 110

Val Thr Asn Phe Leu Val Thr Pro Ala Gln Val Gln Gly Arg Cys Pro
            115                 120                 125

Glu His Pro Ser Val Pro Leu Ala Asn Cys Trp Val Asp Glu Asp Cys
            130                 135                 140

Pro Glu Gly Glu Gly Gly Thr His Ser His Gly Val Lys Thr Gly Gln
145                 150                 155                 160

Cys Val Val Phe Asn Gly Thr His Arg Thr Cys Glu Ile Trp Ser Trp
                165                 170                 175

Cys Pro Val Glu Ser Gly Val Val Pro Ser Arg Pro Leu Leu Ala Gln
            180                 185                 190

Ala Gln Asn Phe Thr Leu Phe Ile Lys Asn Thr Val Thr Phe Ser Lys
            195                 200                 205

Phe Asn Phe Ser Lys Ser Asn Ala Leu Glu Thr Trp Asp Pro Thr Tyr
210                 215                 220

Phe Lys His Cys Arg Tyr Glu Pro Gln Phe Ser Pro Tyr Cys Pro Val
225                 230                 235                 240

Phe Arg Ile Gly Asp Leu Val Ala Lys Ala Gly Gly Thr Phe Glu Asp
                245                 250                 255

Leu Ala Leu Leu Gly Gly Ser Val Gly Ile Arg Val His Trp Asp Cys
            260                 265                 270

Asp Leu Asp Thr Gly Asp Ser Gly Cys Trp Pro His Tyr Ser Phe Gln
            275                 280                 285

Leu Gln Glu Lys Ser Tyr Asn Phe Arg Thr Ala Thr His Trp Trp Glu
            290                 295                 300

Gln Pro Gly Val Glu Ala Arg Thr Leu Leu Lys Leu Tyr Gly Ile Arg
305                 310                 315                 320

Phe Asp Ile Leu Val Thr Gly Gln Ala Gly Lys Phe Gly Leu Ile Pro
                325                 330                 335

Thr Ala Val Thr Leu Gly Thr Gly Ala Ala Trp Leu Gly Val Val Thr
            340                 345                 350

Phe Phe Cys Asp Leu Leu Leu Tyr Val Asp Arg Glu Ala His Phe
            355                 360                 365

Tyr Trp Arg Thr Lys Tyr Glu Glu Ala Lys Ala Pro Lys Ala Thr Ala
            370                 375                 380

Asn Ser Val Trp Arg Glu Leu Ala Leu Ala Ser Gln Ala Arg Leu Ala
385                 390                 395                 400

Glu Cys Leu Arg Arg Ser Ser Ala Pro Ala Pro Thr Ala Thr Ala Ala
                405                 410                 415

Gly Ser Gln Thr Gln Thr Pro Gly Trp Pro Cys Pro Ser Ser Asp Thr
            420                 425                 430

His Leu Pro Thr His Ser Gly Ser Leu
```

```
                435                 440
```

<210> SEQ ID NO 32
<211> LENGTH: 379
<212> TYPE: PRT
<213> ORGANISM: Rattus rattus

<400> SEQUENCE: 32

```
Met Ala Ser Ala Val Ala Ala Leu Val Ser Trp Gly Phe Leu Asp
  1               5                  10                  15

Tyr Lys Thr Glu Lys Tyr Val Met Thr Arg Asn Cys Trp Val Gly Ile
                 20                  25                  30

Ser Gln Arg Leu Leu Gln Leu Gly Val Val Tyr Val Ile Gly Trp
             35                  40                  45

Ala Leu Leu Ala Lys Lys Gly Tyr Gln Glu Trp Asp Met Asp Pro Gln
         50                  55                  60

Ile Ser Val Ile Thr Lys Leu Lys Gly Val Ser Val Thr Gln Val Lys
 65                  70                  75                  80

Glu Leu Glu Lys Arg Leu Trp Asp Val Ala Asp Phe Val Arg Pro Ser
                 85                  90                  95

Gln Gly Glu Asn Val Phe Phe Leu Val Thr Asn Phe Leu Val Thr Pro
            100                 105                 110

Ala Gln Val Gln Gly Arg Cys Pro Glu His Pro Ser Val Pro Leu Ala
        115                 120                 125

Asn Cys Trp Ala Asp Glu Asp Cys Pro Glu Gly Glu Met Gly Thr Tyr
130                 135                 140

Ser His Gly Ile Lys Thr Gly Gln Cys Val Ala Phe Asn Gly Thr His
145                 150                 155                 160

Arg Thr Cys Glu Ile Trp Ser Trp Cys Pro Val Glu Ser Ser Ala Val
                165                 170                 175

Pro Arg Lys Pro Leu Leu Ala Gln Ala Lys Asn Phe Thr Leu Phe Ile
            180                 185                 190

Lys Asn Thr Val Thr Phe Asn Lys Phe Asn Phe Ser Arg Thr Asn Ala
        195                 200                 205

Leu Asp Thr Trp Asp Asn Thr Tyr Phe Lys Tyr Cys Leu Tyr Asp Ser
210                 215                 220

Leu Ser Ser Pro Tyr Cys Pro Val Phe Arg Ile Gly Asp Leu Val Ala
225                 230                 235                 240

Met Thr Gly Gly Asp Phe Glu Asp Leu Ala Leu Leu Gly Gly Ala Val
                245                 250                 255

Gly Ile Asn Ile His Trp Asp Cys Asn Leu Asp Thr Lys Gly Ser Asp
            260                 265                 270

Cys Ser Pro Gln Tyr Ser Phe Gln Leu Gln Glu Arg Gly Tyr Asn Phe
        275                 280                 285

Arg Thr Ala Asn Tyr Trp Trp Ala Ala Ser Gly Val Glu Ser Arg Ser
    290                 295                 300

Leu Leu Lys Leu Tyr Gly Ile Arg Phe Asp Ile Leu Val Thr Gly Gln
305                 310                 315                 320

Ala Gly Lys Phe Ala Leu Ile Pro Thr Ala Ile Thr Val Gly Thr Gly
                325                 330                 335
```

```
Ala Ala Trp Leu Gly Met Val Thr Phe Leu Cys Asp Leu Leu Leu Leu
            340             345             350

Tyr Val Asp Arg Glu Ala Gly Phe Tyr Trp Arg Thr Lys Tyr Glu Glu
            355             360             365

Ala Arg Ala Pro Lys Ala Thr Thr Asn Ser Ala
370                 375
```

NUCLEIC ACIDS ENCODING A FUNCTIONAL HUMAN PURINORECEPTOR P2X3 AND P2X6, AND METHODS OF PRODUCTION AND USE THEREOF

This application is a continuation-in-part of Ser. No. 09/008,526 filed on Jan. 16, 1998, now abandoned, and Ser. No. 09/008,185 filed on Jan. 16, 1998, now abandoned; and also claims priority to provisional application Ser. No. 60/071,298 filed Jan. 16, 1998 and provisional application Ser. No. 60/071,669 filed Jan. 16, 1998.

TECHNICAL FIELD

The invention relates generally to receptor proteins and to DNA and RNA molecules encoding therefor. In particular, the invention relates to a nucleic acid sequence that encodes a human receptor P2X$_3$ and P2X$_6$. The invention also relates to methods of using the receptors encoded thereby to identify compounds that interact with them. This invention further relates to compounds which act as antagonists and agonists to compounds which have reactivity with the various P2X receptor and methods utilized in determining said reactivity. The invention also involves therapeutic uses involving aspects of these receptors. The invention relates generally to receptor ligand screening methods. In particular, the invention relates to a method of using stably transfected cell lines that express human purinoreceptors to identify purinoreceptor ligands.

BACKGROUND OF THE INVENTION

P2 receptors have been generally categorized as either metabotropic nucleotide receptors or ionotropic receptors for extracellular nucleotides. Metabotropic nucleotide receptors (usually designated P2Y or P2Y$_n$, where "n" is a subscript integer indicating subtype) are believed to differ from ionotropic receptors (usually designated P2X or P2X$_n$) in that they are based on a different fundamental means of transmembrane signal transduction: P2Y receptors operate through a G protein-coupled system, while P2X receptors are ligand-gated ion channels. The ligand for these P2X receptors is ATP, and/or other natural nucleotides, for example, ADP, UTP, UDP, or synthetic nucleotides, for example 2-methylthioATP.

At least seven P2X receptors, and the cDNA sequences encoding them, have been identified to date. P2X$_1$ cDNA was cloned from the smooth muscle of the rat vas deferens (Valera et al. (1994) Nature 371:516–519) and P2X$_2$ cDNA was cloned from PC12 cells (Brake et al. (1994) Nature 371:519–523). Five other P2X receptors have been found in cDNA libraries by virtue of their sequence similarity to P2X$_1$ and P2X$_2$ (P2X$_3$: Lewis et al. (1995) Nature 377:432–435, Chen et al. (1995) Nature 377:428–431; P2X$_4$: Buell et al. (1996) EMBO J. 15:55–62, Seguela et al. (1996) J. Neurosci. 16:448–455, Bo et al. (1995) FEBS Lett. 375:129–133, Soto et al. (1996) Proc. Natl. Acad. Sci. USA 93:3684–3688, Wang et al. (1996) Biochem. Biophys. Res. Commun.220:196–202; P2X$_5$: Collo et al. (1996) J. Neurosci. 16:2495–2507, Garcia-Guzman et al. (1996) FEBS Lett. 388:123–127; P2X$_6$: Collo et al. (1996), supra, Soto et al. (1996) Biochem. Biophys. Res. Commun. 223:456–460; P2X$_7$: Surprenant et al. (1996) Science 272:735–738). For a comparison of the amino acid sequences of rat P2X receptors see Buell et al. (1996) Eur. J. Neurosci. 8:2221–2228.

Native P2X receptors form rapidly activated, nonselective cationic channels that are activated by ATP. Rat P2X$_1$ and rat P2X$_2$ have equal permeability to Na$^+$ and K$^+$ but significantly less to Cs$^+$. The channels formed by the P2X receptors generally have high Ca$^{2+}$ permeability (P$_{Ca}$/P$_{Na}$≈4). The cloned rat P2X$_1$, P2X$_2$ and P2X$_4$ receptors exhibit the same permeability for Ca$^{2+}$ observed with native receptors. However, the mechanism by which P2X receptors form an ionic pore or bind ATP is not known.

A variety of tissues and cell types, including epithelial, immune, muscle and neuronal, express at least one form of P2X receptor. The widespread distribution of P2X$_4$ receptors in the rat central nervous system suggests a role for P2X$_4$-mediated events in the central nervous system. However, study of the role of individual P2X receptors is hampered by the lack of receptor subtype-specific agonists and antagonists. For example, one agonist useful for studying ATP-gated channels is α,β-methylene-ATP (α,βmeATP). However, the P2X receptors display differential sensitivity to the agonist with P2X$_1$ and P2X$_2$ being α,βmeATP-sensitive and insensitive, respectively. Furthermore, binding of α,βmeATP to P2X receptors does not always result in channel opening. The predominant forms of P2X receptors in the rat brain, P2X$_4$ and P2X$_6$ receptors, cannot be blocked by suramin or PPADS. These two forms of the P2X receptor are also not activated by α,βmeATP and are, thus, intractable to study with currently available pharmacological tools.

A therapeutic role for P2 receptors has been suggested, for example, for cystic fibrosis (Boucher et al. (1995) in: Belardinelli et al. (eds) Adenosine and Adenine Nucleotides: From Molecular Biology to Integrative Physiology (Kluwer Acad., Norwell Mass.) pp 525–532), diabetes (Loubatiéres-Mariani et al. (1995) in: Belardinelli et al. (eds), supra, pp 337–345), immune and inflammatory diseases (Di Virgilio et al. (1995) in: Belardinelli et al. (eds), supra, pp 329–335), cancer (Rapaport (1993) Drug Dev. Res. 28:428–431), constipation and diarrhea (Milner et al. (1994) in: Kamm et al. (eds.) Constipation and Related Disorders: Pathophysiology and Management in Adults and Children (Wrightson Biomedical, Bristol) pp 41–49), behavioral disorders such as epilepsy, depression and aging-associated degenerative diseases (Williams (1993) Drug. Dev. Res. 28:438–444), contraception and sterility (Foresta et al. (1992) J. Biol. Chem. 257:19443–19447), and wound healing (Wang et al. (1990) Biochim. Biophys. Res. Commun. 166:251–258).

Accordingly, there is a need in the art for specific agonists and antagonists for each P2X receptor subtype and, in particular, agents that will be effective in vivo, as well as for methods for identifying P2X receptor-specific agonist and antagonist compounds. P2 purinoreceptors have been generally categorized as either metabotropic nucleotide receptors or ionotropic receptors for extracellular nucleotides. Metabotropic nucleotide receptors, designated P2Y$_n$, and the ionotropic receptors, designated P2X$_n$, are distinguished on the basis of their respective transmembrane signal transduction mechanisms as well as structural differences; the P2Y$_n$ receptors operate through a G protein-coupled system, while the P2X$_n$ receptors are ligand-gated ion channels. The ligand for these receptors may be ATP and/or another natural nucleotide such as ADP, UTP and UDP, or a synthetic nucleotides such as 2-methylthioATP.

At least seven P2X receptors, and the cDNA sequences therefore, have been identified to date. P2X$_1$ cDNA has been cloned from the smooth muscle of the rat vas deferens (Valera et al. (1994) *Nature* 371:516–519) and P2X$_2$ cDNA was cloned from PC12 cells (Brake et al. (1994) *Nature* 371:519–523). Five other P2X receptors have been found in rat neuronal cDNA libraries by virtue of their sequence similarity to P2X$_1$ and P2X$_2$ (P2X$_3$: Lewis et al. (1995)

Nature 377:432–435, Chen et al. (1995) Nature 377:428–431; P2X$_4$: Buell et al. (1996) EMBO J. 15:55–62, Seguela et al. (1996) J. Neurosci. 16:448–455, Bo et al. (1995) FEBS Lett. 375:129–133, Soto et al. (1996) Proc. Natl. Acad. Sci. USA 93:3684–3688, Wang et al. (1996) Biochem. Biophys. Res. Commun.220:196–202; P2X$_5$: Collo et al. (1996) J. Neurosci.16:2495–2507, Garcia-Guzman et al. (1996) FEBS Lett. 388:123–127; P2X$_4$: Collo et al. (1996), supra, Soto et al. (1996) Biochem. Biophys. Res. Commun. 223:456–460; P2X$_7$ Surprenant et al. (1996) Science 272:735–738. For a comparison of the amino acid sequences of rat P2X receptors see Buell et al. (1996) Eur. J. Neurosci. 8:2221–2228. -38-

Native P2X receptors form rapidly-activated, nonselective cationic channels that are activated by ATP. P2X$_1$ and P2X$_2$ have equal permeability to Na$^+$ and K$^+$ but significantly less to Cs$^+$. The channels formed by the P2X receptors generally have high Ca$^{2+}$ permeability ($P_{Ca}/P_{Na}^4$). The cloned rat P2X$_1$, P2X$_2$, and P2X$_4$ receptors exhibit the same permeability for Ca$^{2+}$ observed with native receptors. However, the mechanism by which P2X receptors form an ionic pore or bind ATP is not known.

A variety of tissues and cell types, including epithelial, immune, muscle and neuronal, express at least one form of P2X receptor. (As there appear to be heteromeric as well as homomeric P2X receptors in certain tissues, and without intending to be bound by theory, it is believed that some cells in fact express two or more receptor forms.) Moreover, the association of particular receptor types with certain tissues suggests a functional specialization for some of these receptors. For example, the widespread distribution of P2X$_4$ receptors in the rat central nervous system suggests a role for P2X$_4$-mediated events in the central nervous system.

Unfortunately, study of the role of individual P2X receptors is hampered by the lack of receptor subtype-specific agonists and antagonists. One agonist useful for studying ATP-gated channels is, -methylene-ATP (, meATP); however, the P2X receptors display differential sensitivity to the agonist with P2X$_1$ and P2X$_2$ being, meATP-sensitive and insensitive, respectively. Furthermore, binding of, meATP to P2X receptors does not always result in channel opening. The predominant forms of P2X receptors in the rat brain, P2X$_4$ and P2X$_6$ receptors, cannot be blocked by suramin or pyridoxal phosphate-6-azophenyl-2',4'-disulphonic acid ("PPADS"). These two forms of the P2X receptor are also not activated by, meATP and are, thus, intractable to study with currently available pharmacological tools.

Similarly, a variety of P2Y receptors have been identified and cloned from tissues such as erythroleukemia cells (P2Y$_1$), airway epithelium (P2Y$_2$ and P2Y$_6$), and placenta (P2Y$_4$).

A potential therapeutic role for P2 purinoreceptors has been suggested, e.g., for cystic fibrosis (Boucher et al. (1995) in: Belardinelli et al. (eds.) *Adenosine and Adenine Nucleotides: From Molecular Biology to Integrative Physiology* (Kluwer Acad., Norwell Mass.) pp 525–532), diabetes (Loubatiéres-Mariani et al. (1995) in: Belardinelli et al. (eds), supra, pp 337–345, immune and inflammatory diseases (Di Virgilio et al. (1995) in: Belardinelli et al. (eds), supra, pp 329–335), cancer (Rapaport (1993) *Drug Dev. Res.* 28:428–431), constipation and diarrhea (Milner et al. (1994) in: Kamm et al. (eds.) *Constipation and Related Disorders: Pathophysiology and Management in Adults and Children* (Wrightson Biomedical, Bristol) pp 41–49), behavioral disorders such as epilepsy, depression and aging-associated degenerative diseases (Williams (1993) *Drug. Dev. Res.* 28:438–444), contraception and sterility (Foresta et al. (1992) *J. Biol. Chem.* 257:19443–19447 ) and wound healing (Wang et al. (1990) *Biochim. Biophys. Res. Commun.* 166:251–258). There additionally may be possibilities in the treatment of pain, particularly in connection with P2X$_3$ homomeric receptors and P2X$_2$/X$_3$ heteromeric receptors.

Accordingly, for both research and therapeutic purposes there is a need in the art for specific agonists and antagonists for each purinoreceptor subtype and, in particular, agents that will be effective in vivo, as well as for methods for identifying purinoreceptor-specific agonist and antagonist compounds.

SUMMARY OF THE INVENTION

The present invention relates to human P2X$_3$and P2X$_6$ receptors.

In one embodiment, a DNA molecule or fragments thereof is provided, wherein the DNA molecule encodes aforementioned human P2X receptors, or subunits thereof.

In another embodiment, a recombinant vector comprising such DNA molecules, or fragments thereof, is provided.

In another embodiment, the subject invention is directed to a human P2X$_3$ and P2X$_6$ receptor polypeptides, either alone or in multimeric form.

In still other embodiments, the invention is directed to messenger RNA encoded by the DNA, recombinant host cells transformed or transfected with vectors comprising the DNA or fragments thereof, and methods of producing recombinant P2X polypeptides using such cells.

In yet another embodiment, the invention is directed to a method of expressing the above human P2X receptors, or a subunit thereof, in a cell to produce the resultant P2X-containing receptors.

In a further embodiment, the invention is directed to a method of using such cells to identify potentially therapeutic compounds that modulate or otherwise interact with the above P2X-containing receptors.

In another embodiment, therapeutic uses involving P2X modulators, such as an ATP agonist or antagonist are contemplated.

These and other embodiments of the present invention will readily occur to those of ordinary skill in the art in view of the disclosure herein. The present invention relates to a method of identifying compounds that modulate the receptor or other therapeutic compounds using such cells. The method herein offers a variety of advantages, in that it (a) provides a means of distinguishing, during screening of compounds, between receptor agonists and antagonists; (b) exhibits greater sensitivity than conventional methodologies, especially with respect to P2Y receptors and known phosphoinositide hydrolysis assays; and/or (c) is suitable for testing all P2 receptor agonists over a broad range of ligand concentrations.

In one embodiment, the invention is directed to a method for identifying compounds that modulate the activity of a purinoreceptor selected from the group consisting of human P2X and P2Y purinoreceptors. The method comprises (a) providing a cell which is a purinoreceptor null cell in its native non-transformed state and which comprises and expresses a polynucleotide encoding a human purinoreceptor polypeptide; (b) mixing a test compound with the cell; and (c) measuring either (i) the effect of the test compound on the activation of the human purinoreceptor or the cell expressing the purinoreceptor receptor, or (ii) the binding of the test compound to the cell or the receptor.

In another embodiment, the invention relates to a method for determining the amount of a receptor agonist or antagonist in a test sample. The method comprises (a) providing a cell that expresses a purinoreceptor polypeptide coding sequence, (b) mixing a the cell with a test sample, and (c) measuring the effect of the test compound on the activation of the purinoreceptor or the cell expressing the purinoreceptor receptor.

The purinoreceptors so expressed and utilized for testing may comprise either P2X or P2Y receptor subunits or, in the case of heteromeric constructs, both. Preferred types of P2X receptor include $P2X_2$, $P2X_3$ and $P2X_7$, as well as $P2X_2/X3$ heteromers, with $P2X_3$ being particularly favored. Preferred types of P2Y receptor include $P2Y_1$, $P2Y_2$, $P2Y_4$ and $P2Y_6$, with $P2Y_2$ being particularly favored.

These and other embodiments of the present invention will readily occur to those of ordinary skill in the art in view of the disclosure herein. In particular, while the description and examples which follow are drawn to the cloning, expression and testing of human purinoreceptors, it is anticipated that the method of the present invention may be carried out using analogous mammalian receptors from non-human sources, whose sequences and/or functional properties are similar enough to those of the corresponding human receptors as to be readily substituted therefor without undue experimentation. Such non-human, and especially rat, P2 receptor clones may in such instances be regarded as equivalents to their human counterparts.

BRIEF DESCRIPTION OF THE DRAWINGS

FIG. 1 depicts the sequence of the $P2X_3$ 5'RACE product of Example 2(SEQ ID NO: 13), in which the sequences of primers are underlined and the predicted initiation codon (ATG) is shown in boldface.

FIG. 2 depicts the sequence of the $P2X_3$ 3'RACE product of Example 3 (SEQ ID NO:14), in which the sequences of primers are underlined and the predicted termination codon (TAG) is shown in boldface.

FIG. 3 depicts the sequence of the complete open reading frame of cDNA encoding human $P2X_3$ receptor polypeptide (SEQ ID NO:15). The initiation (ATG) and termination (TAG) codons are shown in boldface; 5' and 3' flanking sequences introduced during plasmid construction, including the EcoRI (GAATTC) and Not I (GCGGCCGC) restriction sites, are underlined.

FIG. 4 depicts the aligned predicted amino acid sequences of human ($hP2X_3$) (SEQ ID NO:16) and rat (r $P2X_3$) (SEQ ID NO:17) receptor polypeptides. Identical residues are identified by boxing.

FIG. 5 depicts the sequence of the 5' end of the $P2X_6$ 5'RACE product of Example 7 (SEQ ID NO:27), in which the predicted initiation codon (ATG) is shown in boldface and the Universal Amplification Primer (see below) is underlined. The length of the poly-dG-dC stretch (double-underlined) varied between clones analyzed.

FIG. 6 depicts the sequence of the 5' end of the $P2X_6$ 3'RACE product of Example 7) (SEQ ID NO:28), in which the sequence of Primer H $P2X_6$-2s is underlined and the predicted termination codon (TAG) is shown in boldface.

FIG. 7 depicts the concensus 3' end of the 3'RACE product of Example 8 (SEQ ID NO:29), in which the sequence complementary to the Adapter Primer is underlined. The length of the poly-adenylation stretch varied between clones analyzed.

FIG. 8 depicts the sequence of the complete open reading frame of cDNA encoding human $P2X_6$ receptor polypeptide (SEQ ID NO:30). The initiation and termination codons are shown in boldface: 5' and 3' flanking sequences introduced during plasmid construction, including the BamHI (GGATCC) and Not I (GCGGCCGC) restruction sites, are underlined.

FIG. 9 depicts the aligned predicted amino acid sequences of human ($hP2X_6$) (SEQ ID NO:31) and rat (r $P2X_6$) (SEQ ID NO:32) $P2X_6$ receptor polypeptides. Identical residues are identified by blocking.

FIG. 10 depicts the sequence of the intact open reading frame of the human $P2X_4$ receptor (SEQ ID NO:1). The EcoRI sites used in subcloning are underlined and the start (ATG) and stop (TGA) codons of the open reading frame ("ORF") are shaded.

FIG. 11A is the Genbank submission (Accession No.U07225) of the human $P2Y_2$ receptor DNA sequence described in Example 4 (SEQ ID NO:2), in which the regions used for sense and antisense primer design are underlined. FIG. 11B is the Genbank submission (same accession number) of the wild type human $P2Y_2$ amino acid sequence (SEQ ID NO:3).

FIG. 12A is the cDNA sequence (SEQ ID NO:4) of the $P2Y_2$ clone prepared as described in Example 4, in which the primer sequences are underlined and the start (ATG) and stop (TGA) codons of the open reading frame are shown in bold italics. FIG. 12B is the amino acid sequence (SEQ ID NO:5) of the $P2Y_2$ receptor encoded by the cDNA sequence depicted in FIG. 12A.

FIG. 13 is the cDNA sequence (SEQ ID NO:6) of the $P2X_3$ clone prepared as described in Example 7.

FIG. 14 is the sequence of the RACE product of Example 7B (SEQ ID NO:23), including the EcoRl sites from the TA vector, in which the sequences of the amplimers (universal amplification primer and the complement to 5'RACE primer 4a) are underlined and the predicted termination codon is in bold.

FIG. 15 is the sequence of the RACE product of Example 7C (SEQ ID NO:24), including the EcoRl sites from the TA vector, in which the sequences of the amplimers (universal amplification primer and the complement to 3'RACE primer 2s) are underlined and the predicted termination codon is in bold.

DETAILED DESCRIPTION OF THE INVENTION

The practice of the present invention will employ, unless otherwise indicated, conventional techniques of molecular biology, microbiology, recombinant DNA technology, electrophysiology, and pharmacology, that are within the skill of the art. Such techniques are explained fully in the literature. See, for example, Sambrook, Fritsch & Maniatis, Molecular Cloning: A Laboratory Manual, Second Edition (1989); DNA Cloning, Vols. I and II (D.N. Glover Ed. 1985); Perbal, B., A Practical Guide to Molecular Cloning (1984); the series, Methods In Enzymology (S. Colowick and N. Kaplan eds., Academic Press, Inc.); Transcription and Translation (Hames et al. eds. 1984); Gene Transfer Vectors For Mammalian Cells (J. H. Miller et al. eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. eds. (1991) IRL Press).

All patents, patent applications and publications cited herein, whether supra or infra, are hereby incorporated by reference in their entirety and are deemed representative of the prevailing state of the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

In describing the present invention, the following terms will be employed, and are intended to be defined as indicated below.

The term "P2 receptor" intends a purinergic receptor for the ligand ATP and/or other purine or pyrimidine nucleotides, whether natural or synthetic. P2 receptors are broadly subclassified as "P2X" or "P2Y" receptors. These types differ in their pharmacology, structure, and signal transduction mechanisms. The P2X receptors are generally ligand-gated ion channels, while the P2Y receptors operate generally through a G protein-coupled system. Moreover, and without intending to be limited by theory, it is believed that P2X receptors comprise multimers of receptor polypeptides, which multimers may be of either the same or different subtypes. Consequently, the term "P2X receptor" refers, as appropriate, to the individual receptor subunit or subunits, as well as to the homomeric and heteromeric receptors comprised thereby.

The term "$P2X_n$" intends a P2X receptor subtype wherein n is an integer of at least 1. At the time of the invention, at least 7 $P2X_n$ receptor subtypes have been isolated and/or characterized.

A "$P2X_3$ receptor agonist" is a compound that binds to and activates a $P2X_3$ receptor. Similarly, a "$P2X_6$ receptor agonist" is a compound that binds to and activates a $P2X_6$ receptor. By "activates" is intended the elicitation of one or more pharmacological, physiological, or electrophysiological responses. Such responses may include, but are not limited to, an increase in receptor-specific cellular depolarization.

A "$P2X_3$ receptor antagonist" is a substance that binds to a $P2X_3$ receptor and prevents agonists from activating the receptor. Similarly, a "$P2X_6$ receptor antagonist", is a substance that binds to a $P2X_6$ receptor, and prevents agonists from activating its corresponding receptor. Pure antagonists do not activate the receptor, but some substances may have mixed agonist and antagonist properties.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, such as by methylation and/or by capping, and unmodified forms of the polynucleotide.

The term "variant" is used to refer to an oligonucleotide sequence which differs from the related wild-type sequence in the insertion, deletion or substitution of one or more nucleotides. When not caused by a structurally conservative mutation (see below), such a variant oligonucleotide is expressed as a "protein variant" which, as used herein, indicates a polypeptide sequence that differs from the wild-type polypeptide in the insertion, deletion or substitution of one or more amino acids. The protein variant differs in primary structure (amino acid sequence), but may or may not differ significantly in secondary or tertiary structure or in function relative to the wild-type.

The term "mutant" generally refers to an organism or a cell displaying a new genetic character or phenotype as the result of change in its gene or chromosome. In some instances, however, "mutant" may be used in reference to a variant protein or oligonucleotide and "mutation" may refer to the change underlying the variant.

"Polypeptide" and "protein" are used interchangeably herein and indicate a molecular chain of amino acids linked through peptide bonds. The terms do not refer to a specific length of the product. Thus, peptides, oligopeptides, and proteins are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide, provided that such fragments, etc. retain the binding or other characteristics necessary for their intended use.

A "functionally conservative mutation" as used herein intends a change in a polynucleotide encoding a derivative polypeptide in which the activity is not substantially altered compared to that of the polypeptide from which the derivative is made. Such derivatives may have, for example, amino acid insertions, deletions, or substitutions in the relevant molecule that do not substantially affect its properties. For example, the derivative can include conservative amino acid substitutions, such as substitutions which preserve the general charge, hydrophobicity/hydrophilicity, side chain moiety, and/or steric bulk of the amino acid substituted, for example, Gly/Ala, Val/Ile/Leu, Asp/Glu, Lys/Arg, Asn/Gln, Thr/Ser, and Phe/Trp/Tyr.

By the term "structurally conservative mutant" is intended a polynucleotide containing changes in the nucleic acid sequence but encoding a polypeptide having the same amino acid sequence as the polypeptide encoded by the polynucleotide from which the degenerate variant is derived. This can occur because a specific amino acid may be encoded by more than one "codon," or sequence of three nucleotides, i.e., because of the degeneracy of the genetic code.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vectors or other transfer DNA, immaterial of the method by which the DNA is introduced into the cell or the subsequent disposition of the cell. The terms include the progeny of the original cell which has been transfected. Cells in primary culture as well as cells such as oocytes also can be used as recipients.

A "vector" is a replicon in which another polynucleotide segment is attached, such as to bring about the replication and/or expression of the attached segment. The term includes expression vectors, cloning vectors, and the like.

A "coding sequence" is a polynucleotide sequence that is transcribed into mRNA and/or translated into a polypeptide. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences. Variants or analogs may be prepared by the deletion of a portion of the coding sequence, by insertion of a sequence, and/or by substitution of one or more nucleotides within the sequence. Techniques for modifying nucleotide sequences, such as site-directed mutagenesis, are well known to those skilled in the art. See, for example, Sambrook et al., supra; DNA Cloning, Vols. I and II, supra; Nucleic Acid Hybridization, supra.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences. A coding sequence may be operably linked to control sequences that direct the transcription of the polynucleotide whereby said polynucleotide is expressed in a host cell.

The term "transfection" refers to the insertion of an exogenous polynucleotide into a host cell, irrespective of the method used for the insertion, or the molecular form of the polynucleotide that is inserted. The insertion of a polynucleotide per se and the insertion of a plasmid or vector comprised of the exogenous polynucleotide are included. The exogenous polynucleotide may be directly transcribed and translated by the cell, maintained as a nonintegrated vector, for example, a plasmid, or alternatively, may be stably integrated into the host genome. "Transfection" generally is used in reference to a eukaryotic cell while the term "transformation" is used to refer to the insertion of a polynucleotide into a prokaryotic cell. "Transformation" of a eukaryotic cell also may refer to the formation of a cancerous or tumorigenic state.

The term "isolated," when referring to a polynucleotide or a polypeptide, intends that the indicated molecule is present in the substantial absence of other similar biological macromolecules. The term "isolated" as used herein means that at least 75 wt. %, more preferably at least 85 wt. %, more preferably still at least 95 wt. %, and most preferably at least 98 wt. % of a composition is the isolated polynucleotide or polypeptide. An "isolated polynucleotide" that encodes a particular polypeptide refers to a polynucleotide that is substantially free of other nucleic acid molecules that do not encode the subject polypeptide; however, the molecule may include functionally and/or structurally conservative mutations as defined herein.

A "test sample" as used herein intends a component of an individual's body which is a source of one of the P2X receptors, including $P2X_3$ and $P2X_6$. These test samples include biological samples which can be evaluated by the methods of the present invention described herein and include body fluids such as whole blood, tissues and cell preparations.

The following single-letter amino acid abbreviations are used throughout the text:

| Alanine | A | Arginine | R |
| Asparagine | N | Aspartic acid | D |
| Cysteine | C | Glutamine | Q |
| Glutamic acid | E | Glycine | G |
| Histidine | H | Isoleucine | I |
| Leucine | L | Lysine | K |
| Methionine | M | Phenylalanine | F |
| Proline | P | Serine | S |
| Threonine | T | Tryptophan | W |
| Tyrosine | Y | Valine | V |

Human $P2X_3$ and $P2X_6$ receptors, polynucleotides encoding variant receptors or polypeptide subunits thereof, and methods of making these receptors are provided herein. The invention includes not only the above P2X receptors but also methods for screening compounds using the receptor and cells expressing the receptor. Further, polynucleotides and antibodies which can be used in methods for detection of the receptor, as well as the reagents useful in these methods, are provided. Compounds and polynucleotides useful in regulating the receptor and its expression also are provided as disclosed hereinbelow.

In one preferred embodiment, the polynucleotide encodes the aforementioned human P2X receptor polypeptides or protein variants thereof containing conservative amino acid substitutions.

DNA encoding the above mentioned human P2X receptors, and variants thereof, can be derived from genomic or cDNA, prepared by synthesis, or by a combination of techniques. The DNA can then be used to express the human P2X receptor or as a template for the preparation of RNA using methods well known in the art (see, Sambrook et al., supra), or as a molecular probe capable of selectively hybridizing to, and therefore detecting the presence of, other P2X-encoding nucleotide sequences.

cDNA encoding the $P2X_3$ and $P2X_6$ receptors may be obtained from an appropriate DNA library. cDNA libraries may be probed using the procedure described by Grunstein et al. (1975) Proc. Natl. Acad. Sci. USA 73:3961. The cDNA thus obtained can then be modified and amplified using the polymerase chain reaction ("PCR") and primer sequences to obtain the specific DNA encoding the human P2X receptor.

More particularly, PCR employs short oligonucleotide primers (generally 10–20 nucleotides in length) that match opposite ends of a desired sequence within the DNA molecule. The sequence between the primers need not be known. The initial template can be either RNA or DNA. If RNA is used, it is first reverse transcribed to cDNA. The cDNA is then denatured, using well-known techniques such as heat, and appropriate oligonucleotide primers are added in molar excess.

Primer extension is effected using DNA polymerase in the presence of deoxynucleotide triphosphates or nucleotide analogs. The resulting product includes the respective primers at their 5'-termini, covalently linked to the newly synthesized complements of the original strands. The replicated molecule is again denatured, hybridized with primers, and so on, until the product is sufficiently amplified. Such PCR methods are described in for example, U.S. Pat. Nos. 4,965,188; 4,800,159; 4,683,202; 4,683,195; incorporated herein by reference in their entireties. The product of the PCR is cloned and the clones containing the P2X receptor DNA, derived by segregation of the primer extended strand, selected. Selection can be accomplished using a primer as a hybridization probe.

Alternatively still, the respective P2X receptor DNA could be generated using an RT-PCR (reverse transcriptase-polymerase chain reaction) approach starting with human RNA. Human RNA may be obtained from cells or tissue in which the specific P2X receptor is expressed, for example, brain, spinal cord, uterus or lung, using conventional methods. For example, single-stranded cDNA is synthesized from human RNA as the template using standard reverse transcriptase procedures and the cDNA is amplified using PCR. This is but one example of the generation of P2X receptor variants from a human tissue RNA template.

Reverse transcription of human RNAs can also be accomplished utiilzing reagents from the Superscript Preamplification System (GibcoBRL, Gaithersburg, Md.) and the following method: Poly A+ RNA (1 microgram) derived from pituitary gland tissue (Clontech, Inc. Palo Alto, Calif.) and 1 µl (50 nanograms) random hexamer primers are combined in a final volume of 12 µl $dH_2O$. This mixture is heated to 70° C. for 10 minutes and chilled on ice for 1 minute. The following components are added: 2 µl 10X PCR buffer (200 mM Tris-HCl pH 8.4, 500 mM KCl), 2 µl 25 mM MgCl$_2$, 1 μl 10 mM dNTP mix, and 2 μl 0.1M dithiothreitol. The reaction is equilibrated for 5 minutes at 25° C. after which 1 μl (200 units) Superscript II reverse transcriptase is added and incubation continued at 25° C. for 10 minutes, followed by 50 minutes at 42° C. Alternatively, 10 picomoles Oligo dT primer can be substituted for the random hexamer primers in the above reaction mixture. In this case, equilibration is carried out at 42° C. for 2 minutes after which the reverse transcriptase is added and incubation continued at 42° C. for 50 minutes. The reverse transcription reaction is terminated by incubation at 70° C. for 15 minutes and chilled on ice. Rnase H (1 μl; 2 units) is added and the mixture incubated for 20 minutes at 37° C., then stored on ice.

Synthetic oligonucleotides may be prepared using an automated oligonucleotide synthesizer such as that described by Warner (1984) DNA 3:401. If desired, the synthetic strands may be labeled with $^{32}$P by treatment with polynucleotide kinase in the presence of $^{32}$P-ATP, using standard conditions for the reaction. DNA sequences, including those isolated from genomic or cDNA libraries, may be modified by known methods which include site-directed mutagenesis as described by Zoller (1982) Nucleic Acids Res. 10:6487. Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. Culture of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions suitable for hybridization with the correct strand, but not with the unmodified sequence. The sequences which have been identified by hybridization are recovered and cloned. Alternatively, it may be necessary to identify clones by sequence analysis if there is difficulty in distinguishing the variant from wild type by hybridization. In any case, the DNA would be sequence-confirmed.

Once produced, DNA encoding the specific P2X receptor may then be incorporated into a cloning vector or an expression vector for replication in a suitable host cell. Vector construction employs methods known in the art. Generally, site-specific DNA cleavage is performed by treating with suitable restriction enzymes under conditions that generally are specified by the manufacturer of these commercially available enzymes. After incubation with the restriction enzyme, protein is removed by extraction and the DNA recovered by precipitation. The cleaved fragments may be separated using, for example, polyacrylamide or agarose gel electrophoresis methods, according to methods known by those of skill in the art.

Sticky end cleavage fragments may be blunt ended using *E. coli* DNA polymerase 1 (Klenow) in the presence of the appropriate deoxynucleotide triphosphates (dNTPs) present in the mixture. Treatment with S1 nuclease also may be used, resulting in the hydrolysis of any single stranded DNA portions.

Ligations are performed using standard buffer and temperature conditions using T4 DNA ligase and ATP. Alternatively, restriction enzyme digestion of unwanted fragments can be used to prevent ligation.

Standard vector constructions generally include specific antibiotic resistance elements. Ligation mixtures are transformed into a suitable host, and successful transformants selected by antibiotic resistance or other markers. Plasmids from the transformants can then be prepared according to methods known to those in the art usually following a chloramphenicol amplification as reported by Clewell et al. (1972) J. Bacteriol. 110:667. The DNA is isolated and analyzed usually by restriction enzyme analysis and/or sequencing. Sequencing may be by the well-known dideoxy method of Sanger et al. (1977) Proc. Natl. Acad. Sci. USA 74:5463) as further described by Messing et al. (1981) Nucleic Acid Res. 9:309, or by the method reported by Maxam et al. (1980) Meth. Enzymol. 65:499. Problems with band compression, which are sometimes observed in GC rich regions, are overcome by use of, for example, T-deazoguanosine or inosine, according to the method reported by Barr et al. (1986) Biotechniques 4:428.

Host cells are genetically engineered with the vectors of this invention, which may be a cloning vector or an expression vector. The vector may be in the form of a plasmid, a viral particle, a phage, etc. The engineered host cells can be cultured in conventional nutrient media modified as appropriate for activating promoters, selecting transformants/transfectants or amplifying the subunit-encoding polynucleotide. The culture conditions, such as temperature, pH and the like, generally are similar to those previously used with the host cell selected for expression, and will be apparent to those of skill in the art.

Both prokaryotic and eukaryotic host cells may be used for expression of desired coding sequences when appropriate control sequences that are compatible with the designated host are used. For example, among prokaryotic hosts, *Escherichia coli* is frequently used. Also, for example, expression control sequences for prokaryotes include but are not limited to promoters, optionally containing operator portions, and ribosome binding sites. Transfer vectors compatible with prokaryotic hosts can be derived from, for example, the plasmid pBR322 that contains operons conferring ampicillin and tetracycline resistance, and the various pUC vectors, that also contain sequences conferring antibiotic resistance markers. These markers may be used to obtain successful transformants by selection. Commonly used prokaryotic control sequences include but are not limited to the lactose operon system (Chang et al. (1977) Nature 198:1056), the tryptophan operon system (reported by Goeddel et al. (1980) Nucleic Acid Res. 8:4057) and the lambda-derived P1 promoter and N gene ribosome binding site (Shimatake et al. (1981) Nature 292:128), the hybrid Tac promoter (De Boer et al. (1983) Proc. Natl. Acad. Sci. USA 292:128) derived from sequences of the trp and lac Uv5 promoters. The foregoing systems are particularly compatible with *E. coli*; however, other prokaryotic hosts such as strains of Bacillus or Pseudomonas may be used if desired.

Eukaryotic hosts include yeast and mammalian cells in culture systems. *Pichia pastoris, Saccharomyces cerevisiae* and *S. carlsbergensis* are commonly used yeast hosts. Yeast-compatible vectors carry markers that permit selection of successful transformants by conferring protrophy to auxotrophic mutants or resistance to heavy metals on wild-type strains. Yeast-compatible vectors may employ the 2-μ origin of replication (Broach et al. (1983) Meth. Enzymol. 101:307), the combination of CEN3 and ARS1 or other means for assuring replication, such as sequences that will result in incorporation of an appropriate fragment into the host cell genome. Control sequences for yeast vectors are known in the art and include but are not limited to promoters for the synthesis of glycolytic enzymes, including the promoter for 3-phosphoglycerate kinase. See, for example, Hess et al. (1968) J. Adv. Enzyme Reg. 7:149, Holland et al. (1978) Biochemistry 17:4900 and Hitzeman (1980) J. Biol. Chem. 255:2073. For example, some useful control systems are those that comprise the glyceraldehyde-3-phosphate dehydrogenase (GAPDH) promoter or alcohol dehydrogenase (ADH) regulatable promoter, or the hybrid yeast promoter ADH2/GAPDH described in Cousens et al. Gene (1987) 61:265–275, terminators also derived from GAPDH, and, if secretion is desired, leader sequences from yeast alpha factor. In addition, the transcriptional regulatory region and the transcriptional initiation region which are operably linked may be such that they are not naturally associated in the wild-type organism.

Mammalian cell lines available as hosts for expression are known in the art and are available from depositories such as the American Type Culture Collection. These include but are not limited to HeLa cells, human embryonic kidney (HEK) cells, Chinese hamster ovary (CHO) cells, baby hamster kidney (BHK) cells, and others. Suitable promoters for mammalian cells also are known in the art and include viral promoters such as that from Simian Virus 40 (SV40), Rous sarcoma virus (RSV), adenovirus (ADV), bovine papilloma virus (BPV) and cytomegalovirus (CMV). Mammalian cells also may require terminator sequences and poly A addition sequences; enhancer sequences which increase expression also may be included, and sequences which cause amplification of the gene also may be desirable. These sequences are known in the art. Vectors suitable for replication in mammalian cells may include viral replicons, or sequences which ensure integration of the appropriate sequences encoding the P2X receptors into the host genome. An example of such a mammalian expression system is described in Gopalakrishnan et al. (1995), Eur. J. Pharmacol.-Mol. Pharmacol. 290:237–246.

Other eukaryotic systems are also known, as are methods for introducing polynucleotides into such systems, such as amphibian cells, using standard methods such as described in Briggs et al. (1995) Neuropharmacol. 34:583–590 or St ühmer (1992) Meth. Enzymol. 207:319–345, insect cells using methods described in Summers and Smith, Texas Agricultural Experiment Station Bulletin No. 1555 (1987), and the like.

The baculovirus expression system can be used to generate high levels of recombinant proteins in insect host cells. This system allows for high level of protein expression, while post-translationally processing the protein in a manner similar to mammalian cells. These expression systems use viral promoters that are activated following baculovirus infection to drive expression of cloned genes in the insect cells (O'Reilly et al. (1992) Baculovirus Expression Vectors: A Laboratory Manual, IRL/Oxford University Press).

Transfection may be by any known method for introducing polynucleotides into a host cell, including packaging the polynucleotide in a virus and transducing a host cell with the virus, by direct uptake of the polynucleotide by the host cell, and the like, which methods are known to those skilled in the art. The transfection procedures selected depend upon the host to be transfected and are determined by the rountineer.

The expression of the receptor may be detected by use of a radioligand selective for the receptor. However, any radioligand binding technique known in the art may be used to detect the receptor (see, for example, Winzor et al. (1995) Quantitative Characterization of Ligand Binding, Wiley-Liss, Inc., N.Y.; Michel et al. (1997) Mol. Pharmacol. 51:524–532). Alternatively, expression can be detected by utilizing antibodies or functional measurements, i.e., ATP-stimulated cellular depolarization using methods that are well known to those skilled in the art. For example, agonist-stimulated $Ca^{2+}$influx, or inhibition by antagonists of agonist-stimulated $Ca^{2+}$influx, can be measured in mammalian cells transfected with the recombinant $P2X_2$ receptor cDNA, such as COS, CHO or HEK cells. Alternatively, $Ca^{2+}$influx can be measured in cells that do not naturally express P2 receptors, for example, the 1321N1 human astrocytoma cell line, have been prepared using recombinant technology to transiently or stably express the $P2X_3$ and $P2X_6$ receptors.

The P2X polypeptides are recovered and purified from recombinant host cell cultures expressing the same by known methods including ammonium sulfate or ethanol precipitation, acid extraction, anion or cation exchange chromatography, phosphocellulose chromatography, hydrophobic interaction chromatography, hydroxyapatite chromatography or lectin chromatography. Protein refolding steps can be used, as necessary, in completing configuration of the protein. Finally, high performance liquid chromatography (HPLC) can be employed for final purification steps.

The human P2X receptor polypeptides, or fragments thereof, of the present invention also may be synthesized by conventional techniques known in the art, for example, by chemical synthesis such as solid phase peptide synthesis. In general, these methods employ either solid or solution phase synthesis methods. See, for example, J. M. Stewart and J. D. Young, Solid Phase Peptide Synthesis, 2nd Ed., Pierce Chemical Co., Rockford, Ill. (1984) and G. Barany and R. B. Merrifield, The Peptides: Analysis, Synthesis, Biology, editors E. Gross and J. Meienhofer, Vol. 2, Academic Press, New York, (1980), pp. 3–254, for solid phase peptide synthesis techniques; and M. Bodansky, Principles of Peptide Synthesis, Springer-Verlag, Berlin (1984) and E. Gross and J. Meienhofer, Eds., The Peptides: Analysis, Synthesis, Biology, supra, Vol. 1, for classical solution synthesis.

In one preferred system, either the DNA or the RNA derived therefrom, each of which encode the specific human P2X receptor, may be expressed by direct injection into a cell, such as a Xenopus laevis oocyte. Using this method, the functionality of the human $P2X_3$ and/or $P2X_6$ receptor encoded by the DNA or the mRNA can be evaluated as follows. A receptor-encoding polynucleotide is injected into an oocyte for translation into a functional receptor subunit. The function of the expressed variant human $P2X_3$ and/or $P2X_6$ receptor can be assessed in the oocyte by a variety of techniques including electrophysiological techniques such as voltage-clamping, and the like.

Receptors expressed in a recombinant host cell may be used to identify compounds that modulate $P2X_3$ and $P2X_6$ activity. In this regard, the specificity of the binding of a compound showing affinity for the receptor is demonstrated by measuring the affinity of the compound for cells expressing the receptor or membranes from these cells. This may be done by measuring specific binding of labeled (for example, radioactive) compound to the cells, cell membranes or isolated receptor, or by measuring the ability of the compound to displace the specific binding of a standard labeled ligand. See, Michel et al., supra. Expression of variant receptors and screening for compounds that bind to, or inhibit the binding of labeled ligand to these cells or membranes, provide a method for rapid selection of compounds with high affinity for the receptor. These compounds may be agonists, antagonists or modulators of the receptor.

Expressed receptors also may be used to screen for compounds that modulate P2X receptor activity. One method for identifying compounds that modulate P2X activity, comprises providing a cell that expresses a specific human P2X receptor polypeptide, combining a test compound with the cell and measuring the effect of the test compound on that P2X receptor activity. The cell may be a bacterial cell, a mammalian cell, a yeast cell, an amphibian cell, an insect or any other cell expressing the receptor. Preferably, the cell is a mammalian cell or an amphibian cell. Thus, for example, a test compound is evaluated for its ability to elicit an appropriate response, for example, the stimulation of cellular depolarization, or for its ability to modulate the response to an agonist or antagonist.

Additionally, compounds capable of modulating P2X receptors are considered potential therapeutic agents in several disorders including, without limitation, central nervous system or peripheral nervous system conditions, for example, epilepsy, pain, depression, neurodegenerative diseases, and the like, and in disorders of skeletal muscle such as neuromuscular diseases.

In addition, the DNA, or RNA derived therefrom, can be used to design oligonucleotide probes for DNAs that express specific P2X receptors. As used herein, the term "probe" refers to a structure comprised of a polynucleotide, as defined above, which contains a nucleic acid sequence complementary to a nucleic acid sequence present in a target polynucleotide. The polynucleotide regions of probes may be composed of DNA, and/or RNA, and/or synthetic nucleotide analogs. Such probes could be useful in in vitro hybridization assays to distinguish $P2X_2$, and $P2X_4$ variants from wild-type message, with the proviso that it may be difficult to design a method capable of making such a distinction given the small differences that may exist between sequences coding the wild-type and a variant P2X receptor. Alternatively, a PCR-based assay could be used to amplify the sample RNA or DNA for sequence analysis.

Furthermore, each specific P2X polypeptide or fragment (s) thereof can be used to prepare monoclonal antibodies using techniques that are well known in the art. The specific P2X receptor or relevant fragments can be obtained using the recombinant technology outlined below, i.e., a recombinant cell that expresses the receptor or fragments can be cultured to produce quantities of the receptor or fragment that can be recovered and isolated. Alternatively, the specific P2X polypeptide or fragment(s) thereof can be synthesized using conventional polypeptide synthetic techniques as known in the art. Monoclonal antibodies that display specificity and selectivity for a particular P2X polypeptide can be labeled with a measurable and detectable moiety, for example, a fluorescent moiety, radiolabels, enzymes, chemiluminescent labels and the like, and used in in vitro assays. It is theorized that such antibodies could be used to identify wild-type or variant P2X receptor polypeptides for immunodiagnostic purposes. For example, antibodies have been generated to detect amyloid b1-40 v. 1-42 in brain tissue (Wisniewski et al. (1996) Biochem. J. 313:575–580; also see, Suzuki et al. (1994) Science 264:1336–1340; Gravina et al. (1995) J. Biol. Chem. 270:7013–7016; and Turnet et al. (1996) J. Biol. Chem. 271:8966–8970).

Therapeutic Indications for Modulators of the Human P2X Receptors

Activation of the P2X receptors by ATP and other nucleotides regulates ion gradients across the cell membrane, modulates the cytosolic concentrations of cations, including $Ca^{2+}$, $Na^+$ and $K^+$, and has a role in the regulation of cell membrane potential. Pain. The rat $P2X_2$ receptor is expressed in the spinal cord, and in the nodose and dorsal root ganglia (Brake et al., Nature 371:519–523 (1994)), while rat $P2X_3$ receptor expression is found primarily in a subset of neurons of the sensory ganglia (Chen et al., Nature 377:428–430 (1995); Vulchanova et al., Neuropharmacol. 36:1229–1242 (1997)). The distribution of both receptors are consistent with a role in pain transmission. The $P2X_2$ and $P2X_3$ receptor subunits form functional channels when expressed alone, and can also form a functional heteromultimeric channel that has properties similar to currents seen in native sensory channels when co-expressed (Lewis et al., Nature 377:432–435 (1995)). Evidence from studies in rat nodose ganglia indicate that both $P2X_2/P2X_3$ heteromeric channels and $P2X_2$ homomeric channels contribute to ATP -induced currents (Virginio et al., J Physiol (Lond) 510:27–35 (1998); Thomas et al., J Physiol (Lond) 509 (Pt 2):411–417 (1998)) ; Vulchanova et al., Proc Natl Acad Sci USA 93:8063–8067 (1996);; Simon et al., Mol Pharmacol 52:237–248 (1997)). ATP, which activates $P2X_2$, $P2X_3$, and $P2X_2/P2X_3$ receptors, functions as an excitatory neurotransmitter in the spinal cord dorsal horn and in primary afferents from sensory ganglia (Holton and Holton, J. Physiol. (Lond.) 126: 124–140 (1954)). ATP-induced activation of P2X receptors on dorsal root ganglion nerve terminals in the spinal cord stimulates the release of glutamate, a key neurotransmitter involved in nociceptive signaling (Gu and MacDermott, Nature 389:749–753 (1997)). Thus, ATP released from damaged cells may evoke pain by activating $P2X_2$, $P2X_3$, or $P2X_2/P2X_3$ receptors on nociceptive nerve endings of sensory nerves. This is consistent with the induction of pain by intradermally applied ATP in the human blister-base model (Bleehen, Br J Pharmacol 62:573–577 (1978)), the identification of $P2X_3$ receptors on nociceptive neurons in the tooth pulp (Cook et al., Nature 387:505–508 (1997)), and with reports that P2X receptor antagonists are analgesic in animal models (Driessen and Starke, Naunyn Schmiedebergs Arch Pharmacol 350:618–625 (1994)). This evidence suggests that $P2X_2$ and $P2X_3$ function in nociception, and that modulators of these human P2X receptors may be useful as analgesics.

Thus, compounds which block or inhibit activation of $P2X_3$ receptors serve to block the pain stimulus Antagonists to compounds which normally activate the $P2X_3$ receptor and/or $P2X_2/P2X_3$ heteromeric channels, such as ATP, could successfully block the transmission of pain.

Other.

ATP is a potent neurotransmitter in neurons of the gastrointestinal tract, and ATP-mediated signals from enteric neurons appear to be characteristic of $P2X_2$ receptors (Zhou and Galligan, J Physiol (Lond) 496 ( Pt 3):719–729 (1996)). Additionally, the discovery of the human $P2X_2$ EST from a library derived from colon tissue suggests that this receptor plays a role in gastrointestinal function. $P2X_2$ is also expressed in vascular smooth muscle tissue, where ATP has been shown to influence vascular tone (Nori et al., J Vasc Res 35:179– 185 (1998) : Kennedy et al., Eur J Pharmacol 107:161–168 (1985)).

The rat $P2X_6$ receptor message has been found to be expressed in a variety of central nervous system tissues, and the distribution of this receptor parallels that of the rat $P2X_4$ receptor (Collo et al., J. Neuroscience 16:2495–2507 (1996)). These two P2X subtypes can interact to form heteromeric receptors with novel pharmacologic properties (Lí et al., J. Neuroscience. 18:7152–7159 (1998)). The tissue distribution of these P2X receptors suggest that these receptors could be a target for pharmaceutical intervention in diseases of the central nervous system.

A recent study identified an mRNA identical to the human P2X6 receptor described herein which is expressed at high levels in skeletal muscle (Urano et al. Cancer Res. 57:3281–3287 (1997)). Additionally, this gene is inducible by the p53 tumor suppressor gene product, suggesting that the human P2X$_6$ receptor plays a role in skeletal muscle cell proliferation and/or differentiation. Therefore, agents that modulate the activity of the P2X$_6$ receptor may be useful as therapeutics for musculoskeletal disorders such as sarcomas. The practice of the present invention will employ, unless otherwise indicated, conventional techniques of molecular biology, microbiology, recombinant DNA technology, electrophysiology, and pharmacology, that are within the skill of the art. Such techniques are explained fully in the literature. See, e.g., Sambrook, Fritsch & Maniatis, *Molecular Cloning: A Laboratory Manual,* Second Edition (1989); *DNA Cloning,* Vols. I and II (D.N. Glover ed. 1985); Perbal, B., *A Practical Guide to Molecular Cloning* (1984); the series, *Methods In Enzymology* (S. Colowick and N. Kaplan eds., Academic Press, Inc.); *Transcription and Translation* (Hames et al. eds. 1984); *Gene Transfer Vectors For Mammalian Cells* (J. H. Miller et al. eds. (1987) Cold Spring Harbor Laboratory, Cold Spring Harbor, N.Y.); Scopes, *Protein Purification: Principles and Practice* (2nd ed., Springer-Verlag); and *PCR: A Practical Approach* (McPherson et al. eds. (1991) IRL Press).

All patents, patent applications and publications cited herein, whether supra or infra, are hereby incorporated by reference in their entirety.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

A. DEFINITIONS

In describing the present invention, the following terms will be employed, and are intended to be defined as indicated below.

The terms "P2 receptor" intends a purinergic receptor for the ligand ATP and/or other purine or pyrimidine nucleotides, natural or synthetic. P2 receptors are broadly subclassified as "P2X" or "P2Y" receptors. These types differ in their pharmacology, structure, and signal transduction mechanisms. The P2X receptors are generally ligand-gated ion channels, while the P2Y receptors operate generally through a G protein-coupled system. Moreover, and unless otherwise specified, the term "P2 receptor" is further intended to mean both homomeric (consisting of one or more identical subunits) and heteromeric (comprising two or more different P2X subunits) receptors. Without intending to be limited by theory, such homomers and heteromers are believed to exist in vivo but may also be expressed by the cloning and transfection methods described below.

The term "subunit" when used in reference to purinoreceptors intends a polypeptide which, either alone or in combinantion with one or more other polypeptides, forms a functional purinoreceptor. Where a purinoreceptor comprises more than one polypeptide subunit, the subunits may be either identical (forming a homomeric multimer) or different (forming a heteromeric multimer).

The term "P2X$_n$" intends a P2X receptor subtype wherein n is an integer of one or more. At the time of the invention, at least 7 human P2X$_n$ receptor subtypes have been isolated and/or characterized.

The term "P2Y$_n$" intends a P2Y receptor subtype wherein n is an integer of one or more. At the time of the invention, at least 4 human P2Y$_n$ receptor subtypes have been isolated and/or characterized.

A "P2X$_n$ receptor agonist" or a "P2Y$_n$ receptor agonist" is a compound that binds to and activates a P2X$_n$ receptor or a P2Y$_n$ receptor, respectively. By "activates" is intended the elicitation of one or more pharmacological, physiological, or electrophysiological responses. Such a response includes, but is not limited to, an increase in receptor-specific cellular depolarization or increase in intracellular calcium levels due to calcium ion influx for a P2X$_n$ receptor, or an increase in intracellular concentration of free $Ca^{2+}$ ($[Ca^{2+}]_i$) and/or inositolphospholipid hydrolysis and the formation of inositol phosphate for a P2Y$_n$ receptor.

A "P2X$_n$ receptor antagonist" or a "P2Y$_n$ receptor antagonist" is a substance that binds to a P2X$_n$ receptor or a P2Y$_n$ receptor, respectively, and prevents agonists from activating the receptor. Pure antagonists do not activate the receptor, but some substances may have mixed agonist and antagonist properties.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, such as by methylation and/or by capping, and unmodified forms of the polynucleotide.

The term "variant" is used to refer to an oligonucleotide sequence which differs from the related wild-type sequence in one or more nucleotides. Such a variant oligonucleotide is expressed as a "protein variant" which, as used herein, indicates a polypeptide sequence that differs from the wild-type polypeptide in the substitution, insertion or deletion of one or more amino acids. A protein variant differs in primary structure (amino acid sequence), but may or may not differ significantly in secondary or tertiary structure or in function relative to the wild-type.

The term "mutant" generally refers to an organism or a cell displaying a new genetic character or phenotype as the result of change in its gene or chromosome. In some instances, however, "mutant" may be used in reference to a variant protein or oligonucleotide and "mutation" may refer to the change underlying the variant.

"Polypeptide" and "protein" are used interchangeably herein and indicate a molecular chain of amino acids linked through peptide bonds. The terms do not refer to a specific length of the product. Thus, peptides, oligopeptides, and proteins are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide.

A "functionally conservative mutation" as used herein intends a change in a polynucleotide encoding a derivative polypeptide in which the activity is not substantially altered compared to that of the polypeptide from which the derivative is made. Such derivatives may have, for example, amino acid insertions, deletions, or substitutions in the relevant molecule that do not substantially affect its properties. For example, the derivative can include conservative amino acid substitutions, such as substitutions which preserve the general charge, hydrophobicity/hydrophilicity, side chain moiety, and/or stearic bulk of the amino acid substituted, for example, Gly/Ala, Val/Ile/Leu, Asp/Glu, Lys/Arg, Asn/Gln, Thr/Ser, and Phe/Trp/Tyr.

By the term "structurally conservative mutant" is intended a polynucleotide containing changes in the nucleic acid sequence but encoding a polypeptide having the same amino acid sequence as the polypeptide encoded by the polynucleotide from which the degenerate variant is derived. This can occur because a specific amino acid may be encoded by more than one "codon," or sequence of three nucleotides, i.e., because of the degeneracy of the genetic code.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vectors or other transfer DNA, immaterial of the method by which the DNA is introduced into the cell or the subsequent disposition of the cell. The terms include the progeny of the original cell which has been transfected. Cells in primary culture as well as cells such as oocytes also can be used as recipients.

A "null" host cell is a host cell that does not express a purinoreceptor of interest within the limits of the methods used to measure the expression of such receptors, either pharmacologically, electrophysiologically, biochemically, or the like. Thus, a P2X-P2Y null cell, that is, a "$P2X^-$-$P2Y^-$ host cell," is a cell in which the presence of neither the P2X receptor nor the P2Y receptor can be measured. This characteristic of the null host cell may be due to mutation of a gene that otherwise naturally encodes a P2X or P2Y receptor such that the mutant encodes a purinoreceptor polypeptide that is not detectable by methods used to detect the native P2X or P2Y receptor. On the other hand, a null host cell may not express a purinoreceptor polypeptide to any measurable extent. The definition of "null" host cell is not intended to be limited to any particular mechanism underlying the absence of measurable levels of a purinoreceptor.

A "vector" is a replicon in which another polynucleotide segment is attached, such as to bring about the replication and/or expression of the attached segment. The term includes expression vectors, cloning vectors, and the like.

A "coding sequence" is a polynucleotide sequence that is transcribed into mRNA and/or translated into a polypeptide. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences. Variants or analogs may be prepared by the deletion of a portion of the coding sequence, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences. A coding sequence may be operably linked to control sequences that direct the transcription of the polynucleotide whereby said polynucleotide is expressed in a host cell.

The term "transfection" refers to the insertion of an exogenous polynucleotide into a host cell, irrespective of the method used for the insertion, or the molecular form of the polynucleotide that is inserted. The insertion of a polynucleotide per se and the insertion of a plasmid or vector comprised of the exogenous polynucleotide are included. The exogenous polynucleotide may be directly transcribed and translated by the cell, maintained as a nonintegrated vector, for example, a plasmid, or alternatively, may be stably integrated into the host genome. "Transfection" generally is used in reference to a eukaryotic cell while the term "transformation" is used to refer to the insertion of a polynucleotide into a prokaryotic cell. "Transformation" of a eukaryotic cell also may refer to the formation of a cancerous or tumorigenic state.

The term "isolated," when referring to a polynucleotide or a polypeptide, intends that the indicated molecule is present in the substantial absence of other similar biological macromolecules. The term "isolated" as used herein means that at least 75 wt. %, more preferably at least 85 wt. %, more preferably still at least 95 wt. %, and most preferably at least 98 wt. % of a composition is the isolated polynucleotide or polypeptide. An "isolated polynucleotide" that encodes a particular polypeptide refers to a polynucleotide that is substantially free of other nucleic acid molecules that do not encode the subject polypeptide; however, the molecule may include functionally and/or structurally conservative mutations as defined herein.

A "test sample" as used herein intends a component of an individual's body which is a source of a purinoreceptor. These test samples include biological samples which can be evaluated by the methods of the present invention described herein and include body fluids such as whole blood, serum, tissues and cell preparations.

The following single-letter amino acid abbreviations are used throughout the text:

| Alanine       | A | Arginine      | R |
|---------------|---|---------------|---|
| Asparagine    | N | Aspartic acid | D |
| Cysteine      | C | Glutamine     | Q |
| Glutamic acid | E | Glycine       | G |
| Histidine     | H | Isoleucine    | I |
| Leucine       | L | Lysine        | K |
| Methionine    | M | Phenylalanine | F |
| Proline       | P | Serine        | S |
| Threonine     | T | Tryptophan    | W |
| Tyrosine      | Y | Valine        | V |

B. GENERAL METHODS

The present invention provides a method for screening a plurality of compounds for specific binding to a purinoreceptor to identify a compound that modulates the activity of the receptor. The method comprises (a) providing a cell that expresses the human (or other mammalian) purinoreceptor polypeptide coding sequence, (b) mixing a test compound with the cell, and (c) measuring the effect of the test compound on the activation of the purinoreceptor or the cell expressing the purinoreceptor receptor.

In addition, the invention provides a method for determining the amount of a receptor agonist or antagonist in a test sample. The method comprises (a) providing a cell that expresses the human (or other mammalian) purinoreceptor polypeptide coding sequence, (b) mixing a the cell with a test sample, and (c) measuring the effect of the test compound on the activation of the purinoreceptor or the cell expressing the purinoreceptor receptor.

The invention disclosed and claimed herein comprises providing a host cell that encodes the purinoreceptor of interest. The host cell is genetically engineered with a vector, which may be a cloning vector or an expression vector, comprising a polynucleotide sequence encoding a purinoreceptor operably linked to control sequences that control its expression. Preferably, the host cell is stably transfected to express the purinoreceptor. More preferably, the host cell is a purinoreceptor null cell which, if not already lacking endogenous purinoreceptor expression, has been so engineered.

The vector may be in the form of a plasmid, a viral particle, a phage, etc. The engineered host cells can be cultured in conventional nutrient media modified as appropriate for activating promoters, selecting transformants/transfectants or amplifying the subunit-encoding polynucleotide. The culture conditions, such as temperature, pH and the like, generally are similar to those previously used with the host cell selected for expression, and will be apparent to those of skill in the art.

Either a prokaryotic or a eukaryotic host cell may be used for expression of desired coding sequences when appropriate control sequences that are compatible with the designated host are used. Preferably the host cell is a null host cell, more preferably, when the expression of the coding sequence result in production of a P2X purinoreceptor polypeptide, the host cell is any P2X$^-$ cell or a cell in which expression of P2X purinoreceptors is less than can be detectably measured. When a P2Y purinoreceptor is produced from expression of the coding sequence, the host cell is preferably a P2Y$^-$ null cell or a cell in which expression of P2Y purinoreceptors is less than can be detectably measured; optionally, but not necessarily, the host cell used to express a P2Y purinoreceptor may be 1321N1 (human astrocytoma) or another P2X$^-$-P2Y$^-$ null cell.

Among prokaryotic hosts, *Escherichia coli* is frequently used. Expression control sequences for prokaryotic host cells include but are not limited to promoters, optionally containing operator portions, and ribosome binding sites. Transfer vectors compatible with prokaryotic hosts can be derived from, for example, the plasmid pBR322 that contains operons conferring ampicillin and tetracycline resistance, and the various pUC vectors, that also contain sequences conferring antibiotic resistance markers. These markers may be used to obtain successful transformants by selection. Commonly used prokaryotic control sequences include but are not limited to the lactose operon system (Chang et al. (1977) *Nature* 198:1056), the tryptophan operon system (reported by Goeddel et al. (1980) *Nucleic Acid Res.* 8:4057) and the lambda-derived P1 promoter and N gene ribosome binding site (Shimatake et al. (1981) *Nature* 292:128), the hybrid Tac promoter (De Boer et al. (1983) *Proc. Natl. Acad. Sci. USA* 292:128) derived from sequences of the trp and lac UV5 promoters. The foregoing systems are particularly compatible with *E. coli;* however, other prokaryotic hosts such as strains of Bacillus or Pseudomonas may be used if desired.

Eukaryotic hosts include yeast and mammalian cells in culture systems. *Pichia pastoris, Saccharomyces cerevisiae* and *S. carlsbergensis* are commonly used yeast hosts. Yeast-compatible vectors carry markers that permit selection of successful transformants by conferring protrophy to auxotrophic mutants or resistance to heavy metals on wild-type strains. Yeast-compatible vectors may employ the 2-μ origin of replication (Broach et al. (1983) *Meth. Enzymol.* 101:307), the combination of CEN3 and ARS1 or other means for assuring replication, such as sequences that will result in incorporation of an appropriate fragment into the host cell genome. Control sequences for yeast vectors are known in the art and include but are not limited to promoters for the synthesis of glycolytic enzymes, including the promoter for 3-phosphoglycerate kinase. See, for example, Hess et al. (1968) *J. Adv. Enzyme Reg.* 7:149, Holland et al. (1978) *Biochemistry* 17:4900 and Hitzeman (1980) *J. Biol. Chem.* 255:2073. For example, some useful control systems are those that comprise the glyceraldehyde-3-phosphate dehydrogenase (GAPDH) promoter or alcohol dehydrogenase (ADH) regulatable promoter, or the hybrid yeast promoter ADH2/GAPDH described in Cousens et al. *Gene* (1987) 61:265–275, terminators also derived from GAPDH, and, if secretion is desired, leader sequences from yeast alpha factor. In addition, the transcriptional regulatory region and the transcriptional initiation region which are operably linked may be such that they are not naturally associated in the wild-type organism.

Mammalian cell lines available as hosts for expression are known in the art and are available from depositories such as the American Type Culture Collection. These include but are not limited to HeLa cells, human embryonic kidney (HEK) cells, Chinese hamster ovary (CHO) cells, baby hamster kidney (BHK) cells, and others. Suitable promoters for mammalian cells also are known in the art and include viral promoters such as that from Simian Virus 40 (SV40), Rous sarcoma virus (RSV), adenovirus (ADV), bovine papilloma virus (BPV) and cytomegalovirus (CMV). Mammalian cells also may require terminator sequences and poly A addition sequences; enhancer sequences which increase expression also may be included, and sequences which cause amplification of the gene also may be desirable. These sequences are known in the art. Vectors suitable for replication in mammalian cells may include viral replicons, or sequences which ensure integration of the appropriate sequences encoding the purinoreceptor into the host genome. An example of such a mammalian expression system is described in Gopalakrishnan et al. (1995), *Eur. J. Pharmacol.* 290: 237–246.]

Other eukaryotic systems are also known, as are methods for introducing polynucleotides into such systems, such as amphibian cells, using standard methods such as described in Briggs et al. (1995) *Neuropharmacol.* 34:583–590 or Stühmer (1992) *Meth. Enzymol.* 207:319–345, insect cells using methods described in Summers and Smith, Texas Agricultural Experiment Station Bulletin No. 1555 (1987), and the like.

The baculovirus expression system can be used to generate high levels of recombinant proteins in insect host cells. This system allows for high level of protein expression, while post-translationally processing the protein in a manner similar to mammalian cells. These expression systems use viral promoters that are activated following baculovirus infection to drive expression of cloned genes in the insect cells (O'Reilly et al. (1992) Baculovirus Expression Vectors: A Laboratory Manual, IRL/Oxford University Press).

DNA encoding the purinoreceptor of interest can be derived from genomic or cDNA, prepared by synthesis, or by a combination of techniques. The DNA can then be used to express the purinoreceptor or as a template for the preparation of RNA using methods well known in the art (see, Sambrook et al., supra). For example, the human P2X$_1$ purinoreceptor cDNA may be obtained as described in International Publication Number WO 95/33048, while the human P2Y$_1$ receptor cDNA may be obtained as described in Léon et al. (1966) *Gene* 171:295–297.

cDNA encoding a P2X$_n$ receptor or a P2Y$_n$ receptor may be obtained from an appropriate DNA library. cDNA libraries may be probed using the procedure described by Grunstein et al. (1975) *Proc. Natl. Acad. Sci. USA* 73:3961. The cDNA thus obtained can then be modified and amplified using the polymerase chain reaction ("PCR") and primer sequences to obtain the DNA encoding the desired P2X$_n$ or P2Y$_n$ receptor. Alternatively, the wild-type DNA may be obtained from an appropriate DNA library. DNA libraries may be probed using the procedure described by Grunstein et al. (1975) *Proc. Natl. Acad. Sci. USA* 73:3961. The wild-type cDNA thus obtained can then modified and amplified using PCR and mutated primer sequences to obtain the DNA encoding the receptor of interest.

More particularly, PCR employs short oligonucleotide primers (generally 10–20 nucleotides in length) that match opposite ends of a desired sequence within the DNA molecule. The sequence between the primers need not be known. The initial template can be either RNA or DNA. If RNA is used, it is first reverse transcribed to cDNA. The cDNA is then denatured, using well known techniques such as heat, and appropriate oligonucleotide primers are added in molar excess.

Alternatively, DNA encoding a human (or other mammalian) $P2X_n$ or $P2Y_n$ receptor can be derived from genomic or cDNA, prepared by synthesis, or by a combination of techniques. The DNA can then be used to express the receptor or as a template for the preparation of RNA using methods well known in the art (see, Sambrook et al., supra). An example of a method for obtaining the desired DNA involves isolating cDNA encoding the wild-type human $P2Y_2$ receptor as described by Parr et al. (1994), supra.

Primer extension is effected using DNA polymerase in the presence of deoxynucleotide triphosphates or nucleotide analogs. The resulting product includes the respective primers at their 5'-termini, covalently linked to the newly synthesized complements of the original strands. The replicated molecule is again denatured, hybridized with primers, and so on, until the product is sufficiently amplified. Such PCR methods are described in, for example, U.S. Pat. Nos. 4,965,188, 4,800,159, 4,683,202 and 4,683,195, and are believed to be well-known to the skilled artisan. The product of the PCR is cloned and the clones containing the $P2X_4$ receptor DNA, derived by segregation of the primer extended strand, selected. Selection can be accomplished using a primer as a hybridization probe.

Alternatively still, the P2Xn receptor or $P2Y^n$ receptor DNA could be generated using an RT-PCR (reverse transcriptase—polymerase chain reaction) approach starting with RNA. The RNA may be obtained from cells or tissue in which the $P2X_n$ or $P2Y_n$ receptor is expressed, e.g., brain, spinal cord, uterus or lung, using conventional methods. For example, single-stranded cDNA is synthesized from RNA as the template using standard reverse transcriptase procedures and the cDNA is amplified using. This is but one example of the generation of a $P2X_n$ or $P2Y_n$ receptor from a mammalian tissue RNA template.

Synthetic oligonucleotides may be prepared using an automated oligonucleotide synthesizer such as that described by Warner (1984) *DNA* 3:401. If desired, the synthetic strands may be labeled with $^{32}P$ by treatment with polynucleotide kinase in the presence of $^{32}P$-ATP, using standard conditions for the reaction. DNA sequences, including those isolated from genomic or cDNA libraries, may be modified by known methods which include site-directed mutagenesis as described by Zoller (1982) *Nucleic Acids Res.* 10:6487. Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. Culture of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions suitable for hybridization with the correct strand, but not with the unmodified sequence. The sequences which have been identified by hybridization are recovered and cloned. Alternatively, it may be necessary to identify clones by sequence analysis if there is difficulty in distinguishing the variant from wild-type by hybridization. In any case, the DNA would be sequence-confirmed.

Once produced, DNA encoding the $P2X_n$ or $P2Y_n$ purinoreceptor may then be incorporated into a cloning vector or an expression vector for replication in a suitable host cell. Vector construction employs methods known in the art. Generally, site-specific DNA cleavage is performed by treating with suitable restriction enzymes under conditions that generally are specified by the manufacturer of these commercially available enzymes. After incubation with the restriction enzyme, protein is removed by extraction and the DNA recovered by precipitation. The cleaved fragments may be separated using, for example, polyacrylamide or agarose gel electrophoresis methods, according to methods known by those of skill in the art.

Sticky end cleavage fragments may be blunt ended using *E. coli* DNA polymerase 1 (Klenow) in the presence of the appropriate deoxynucleotide triphosphates (dNTPs) present in the mixture. Treatment with S1 nuclease also may be used, resulting in the hydrolysis of any single stranded DNA portions.

Ligations are performed using standard buffer and temperature conditions using T4 DNA ligase and ATP. Alternatively, restriction enzyme digestion of unwanted fragments can be used to prevent ligation.

Standard vector constructions generally include specific antibiotic resistance elements. Ligation mixtures are transformed into a suitable host, and successful transformants selected by antibiotic resistance or other markers. Plasmids from the transformants can then be prepared according to methods known to those in the art usually following a chloramphenicol amplification as reported by Clewell et al. (1972) *J. Bacteriol.* 110:667. The DNA is isolated and analyzed usually by restriction enzyme analysis and/or sequencing. Sequencing may be by the well-known dideoxy method of Sanger et al. (1977) *Proc. Natl. Acad. Sci. USA* 74:5463) as further described by Messing et al. (1981) *Nucleic Acid Res.* 9:309, or by the method reported by Maxam et al. (1980) *Meth. Enzymol.* 65:499. Problems with band compression, which are sometimes observed in GC rich regions, are overcome by use of, for example, T-deazoguanosine or inosine, according to the method reported by Barr et al. (1986) *Biotechniques* 4:428.

Transfection may be by any known method for introducing polynucleotides into a host cell, including packaging the polynucleotide in a virus and transducing a host cell with the virus, by direct uptake of the polynucleotide by the host cell, and the like, which methods are known to those skilled in the art. The transfection procedures selected depend upon the host to be transfected and are determined by the rountineer.

The expression of the purinoreceptor may be detected by use of a radioligand selective for the receptor. For example, such ligands include [$^{35}S$]ATP S, [$^{35}S$]ATP S, [$^{35}S$]ATP S, [$^{3}H$]ATP and [$^{3}H$] meATP (see, Michel et al. (1997) *Mol. Pharmacol.* 51:524–532). However, any radioligand binding technique known in the art may be used to detect the receptor (see, e.g., Winzor et al. (1995) *Quantitative Characterization of Ligand Binding,* Wiley-Liss, Inc., N.Y.). Alternatively, expression can be detected by utilizing antibodies or functional measurements, i.e., ATP- or UTP-stimulated cellular depolarization using methods that are well known to those skilled in the art. For example, agonist-stimulated $Ca^{2+}$influx, or inhibition by antagonists of agonist-stimulated $Ca^{2+}$influx, can be measured in mammalian cells that express endogenous and/or recombinant P2 receptor, such as HEK, CHO, COS and PC12 (rat pheochromocytoma) cells. In a particular embodiment of such methods, $Ca^{2+}$influx can be measured in cells that do not naturally express any P2 receptor (such as the 1321N1 human astrocytoma cell line) but have been prepared using recombinant technology to transiently or stably express a human P2X or P2Y purinoreceptor.

In one method of expression, DNA which encodes a P2X or P2Y purinoreceptor, or messenger RNA derived therefrom, may be introduced by direct injection into a cell such as a Xenopus laevis oocyte. Using this method, the functionality of the purinoreceptor encoded by the DNA or the mRNA can be evaluated as follows. A receptor-encoding polynucleotide is injected into an oocyte for translation into a functional receptor subunit. The function of the expressed human purinoreceptor can be assessed in the oocyte by a variety of techniques including electrophysiological techniques such as voltage-clamping (see, e.g., Briggs et al. (1995), supra) and the like.

Receptors expressed in a recombinant host cell may be used to identify compounds that bind to and/or modulate the activity of a purinoreceptor. In this regard, the specificity of the binding of a compound showing affinity for the receptor is demonstrated by measuring the affinity of the compound for cells expressing the receptor or membranes from these cells. This may be done by measuring specific binding of labeled (e.g., radioactive) compound to the cells, cell membranes or isolated receptor, or by measuring the ability of the compound to displace the specific binding of a standard labeled ligand. See, Michel et al., supra. Expression of variant receptors and screening for compounds that bind to, or inhibit the binding of labeled ligand to these cells or membranes, provide a method for rapid selection of compounds with high affinity for the receptor. These compounds may be agonists, antagonists or modulators of the receptor.

Expressed receptors also may be used to screen for compounds that modulate purinoreceptor activity. One method for identifying compounds that modulate human purinoreceptor activity, comprises providing a cell that expresses a human (or, if analogous, other mammalian) purinoreceptor polypeptide, combining a test compound with the cell and measuring the effect of the test compound on the purinoreceptor activity. The cell may be a bacterial cell, a mammalian cell, a yeast cell, an amphibian cell, an insect cell or any other cell expressing the receptor. Preferably, the cell is a mammalian cell or an amphibian cell, more preferably the cell is a purinoreceptor null cell as described above. Thus, for example, a test compound is evaluated for its ability to elicit an appropriate response, e.g., the stimulation of cellular depolarization or increase in intracellular calcium levels due to calcium ion influx if a P2X purinoreceptor is expressed in the host cell, the stimulation of an increase in intracellular calcium ion levels and/or inositolphospholipid hydrolysis and the formation of inositol phosphate if a P2Y purinoreceptor is expressed, or for the compound's ability to modulate the response to a P2X or P2Y purinoreceptor agonist or antagonist.

The level of intracellular calcium may be analyzed using a calcium ion-sensitive fluorescent indicator. Cellular fluorescence may be monitored using a fluorometer. Examples of calcium ion-sensitive fluorescent dyes include, for example, quin-2 (see, e.g., Tsien et al. (1982) *J. Cell. Biol.* 94:325), fura-2 (see, e.g., Grynkiewicz et al. (1985) *J. Biol. Chem.* 260:3440), calcium green-1, indo-1 (see, e.g., Grynkiewicz et al., supra), fluo-3 (see, e.g., Kao et al. (1989) *J. Biol. Chem.* 264:8179) and rhod-2 (see, e.g., Tsien et al. (1987) *J. Biol. Chem.* abstract 89a), and the nonspecific esterase-hydrolyzable acetoxymethyl esters thereof, all of which are commercially available (Molecular Probes, Eugene, Oreg.; Sigma Chemical Co., St. Louis, Mo.).

Membrane depolarization of cells genetically engineered to express a $P2X_n$ purinoreceptor may be monitored using a fluorescent dye that is sensitive to changes in membrane potential. For example, the potential-sensitive fluorescent dye partitions into a membrane upon depolarization and results in a detectable increase in cellular fluorescence. Examples of such membrane potential-sensitive fluorescent dyes include carbocyanines, such as 3,3'-dipentyloxacarbocyanine iodide ($DiOC_5$) and 3,3'-dipropylthiadicarbocyanine iodide ($DiSC_3$), oxonols, such as bis-(1,3-dibutylbarbituric acid)pentamethine oxonol ($DiBAC_4(5)$) or bis-(1,3-dibutylbarbituric acid) pentamethine oxonol ($DiBAC_4(5)$), or the like.

In order to calibrate the fluorescence emission of these dyes in situ, an agent that quenches the fluorescence emission may be used. Thus, for example, anti-fluorescein (Molecular Probes) quenches approximately 87% of the fluorescence of a 5 nM solution of fluo-3 at pH 7.0, and may used to calibrate the fluorescence emission of this dye. When acetoxymethyl ester dye derivatives are use, incomplete hydrolysis of the ester may result in a fluorescent indicator that is flourescent but insensitive to calcium ions. Controls for such a situation include transporting saturating amounts of calcium ions into the cell by an ionophore to achieve the maximum fluorescence response and transport of manganese ions into the cell to quench the fluorescence of the indicator if all acetoxymethyl esters have been hydrolyzed. One means by which such ions can be transported into cells is with the use of an ionophore, such as A23187 (see, e.g., Pressman et al. (1976) *Ann. Rev. Biochem.* 45:501) (Sigma Chemical Co.), the brominated derivative thereof (see, e.g., Deber et al. (1985) *Anal. Biochem.* 146:349) (Molecuar Probes), or other ionophores well known in the art.

In addition, it may be desirable to quantify the amount of intracellular calcium ion from the fluorescence emission of a cell by comparing the fluorescence data obtained from the test compounds to a calibration curve that was generating by a series of calibrators each having a known calcium ion concentration. Thus, calcium ion standards are made having a range of concentrations bu preparing a stock solution of, e.g., $CaCl_2$, from which dilutions may be made to attain the desired standard concentration(s). The fluorescence emission of the standards in the presence of the calcium ion-sensitive fluorescent indicator dye is used to construct a standard curve and the intracellular calcium ion concentration of the genetically engineered cell in the assay is determined from the standard curve. Alternatively, cells previously treated with a calcium ionophore may be incubated with the indicator dye and the calcium ion standards used to generate the standard curve.

The assay may be conducted manually or using an automated system. For a high capacity functional screening assay identifying human purinoreceptor ligands, an automated system is preferred. An example of such an automated system comprises providing a 96-well culture plate in each well of which is cultured a cell genetically engineered to encode and express a human purinoreceptor polypeptide. The plate is loaded into a fluorescence imaging plate reader ("FLIPR"), which simultaneously measures the kinetics of intracellular calcium flux in each of the 96 wells. Such an FLIPR is commercially available from Molecular Devices Corp. (Sunnyvale, Calif.). The FLIPR is capable of quantitatively transferring fluids into and from each well of the 96-well plate and thus can be used to add the calcium-ion sensitive fluorescent indicator dye, a candidate compound, a purinoreceptor agonist, e.g., ATP, UTP, 2-methylthioATP, or the like, and/or a purinoreceptor antagonist, e.g., suramin, cibacron blue, PPADS, or the like. The FLIPR collects fluorescence data throughout the course of the assay.

In a similar manner, the presence of a purinoreceptor agonist or antagonist in a test sample may be determined using a manual or an automated system. An automated system for practicing the method comprises providing a 96-well culture plate in each well of which a genetically engineered cell that expresses a purinoreceptor is cultured. The fluorescent indicator dye, test sample, and/or purinoreceptor agonist are added to each well and the fluorescence emission from each well is simultaneously monitored by an FLIPR.

P2X purinoreceptor drugs are considered potential therapeutic agents in several disorders including, without limitation, central nervous system or peripheral nervous system conditions, e.g., epilepsy, pain, depression, neurodegenerative diseases, and the like, and in disorders of the reproductive system, asthma, peripheral vascular disease, hypertension, immune system disorders, irritable bowel disorder or premature ejaculation.

P2Y purinoreceptors are believed to mediate the activity of extracellular nucleotide triphosphates to regulate chloride secretion in human airway epithelia. Cystic fibrosis exhibits reduced chloride secretion by airway epithelia and, consequently, dehydrated, viscous mucus that obstructs airways and compromises pulmonary function. Thus, drugs that are able to regulate epithelia chloride secretion may provide an alternative non-CFTR-dependent mechanism to induce fluid secretion in cystic fibrosis airways. In addition, extracellular nucleotides stimulate mucus secretion by goblet cells in vitro and excessive activation of this pathway in vivo may be partly responsible for the hypersecretion observed in chronic bronchitis. Thus, drugs that regulate this pathway may have therapeutic value in chronic bronchitis.

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Identification of a Human cDNA Sequence Likely to Encode P2X$_3$ Polypeptide

The predicted amino acid sequence of the rat P2X$_3$ receptor (NCBI sequence I.D. number 1103623) was used to search for human DNA sequences which would code for similar polypeptides. The TBLASTN database search tool (Altschul (1993) *J. Mol. Evol.* 36:390–300) was used, which allows querying nucleotide databases with a protein sequence by dynamically translating the DNA sequences into all 6 possible reading frames. A search of the Genbank sequence-tagged sites (STS) database revealed a human genomic fragment, 229 basepairs in length, containing an open reading fame which would be predicted to encode a polypeptide having a high degree of homology to a region of the rat P2X3 receptor. The deposited sequence for this fragment (Genbank accession number G03901) was as follows:

```
CCCGAATCGG TGGACTGCTT CTCCACTGTG GTCTGGTCGC TGGGGTACAC  (SEQ ID NO:1)
TGGGTTGGTC AAAGCCGCGA TTTTCAGTGT AGTCTCATTC ACNTGNAGGC
GAAAGAGCTG GTGTTGTCAA GTTCTGACTA TGGGCAATGT CCTCTTTTGT
GACCCCATTT GACAGACTCA GCAGTGGGCG CCCATGACCT AGTCATGAGG
GGAGCCAGGA CATCTGTGTG ATCCCAAGG
```

Where "N" represents any of the bases A, T, G and C.

EXAMPLE 2

Identification of the 5' End of the PX2$_3$ cDNA

Based on the sequence of G03901, primers were designed for use in reverse-transcription polymerase chain reaction (RT-PCR) procedures in an effort to isolate the intact open reading frame for this receptor. The primers used in the reactions described below were as follows:

Primer 1s (SEQ ID. NO:2):
    5'-TTTACCAACCCAGTGTACCC-3'
Primer 2s (SEQ ID. NO:3):
    5'-ACCACAGTGGAGAAGCAGTC-3'
Primer 3as (SEQ ID. NO:4):
    5'-GAATCGGTGGACTGCTTCTC-3'
Primer 4as (SEQ ID. NO:5):
    5'CGATTTTCAGTGTAGTCTCATTC-3'
Primer 5as (SEQ ID. NO:6):
    5'GGGGTACACTGGGTTGGTAA-3'
5'RACE Anchor Primer (SEQ ID. NO:7):
    5'CUACUACUACUAGGCCACGCGTCGACTAGTAC GGGIIGGGIIGGGIIG-3'
Universal Adapter Primer (SEQ ID. NO:8):
    5'-CUACUACUACUAGGCCACGCGTCGA CTAGTAC-3'
Adapter Primer (SEQ ID. NO:9):
    5'-GGCCACGCGTCGACTAGTACTTTTTTTTTTTTT TTTT-3'
Abridged Universal Adapter Primer (SEQ ID. NO:10):
    5'-GGCCACGCGTCGACTAGTAC-3'
5'hP2X$_3$ Primer (SEQ ID. NO:11):
    5'-CACCATGAACTGCATATCCGACTTC-3'
3'hP2X$_3$ Primer (SEQ ID. NO:12):
    5'-CTAGTGGCCTATGGAGAAGGC-3'

To identify the 5' end of the cDNA which is derived from the genomic region which sequence G03901 is part of, the RACE technique (Rapid Amplification of cDNA Ends) (Frohman et al. (1988), *Proc. Natl. Acad. Sci. U.S.A.* 85:8998–9002) was employed. Extension of the cDNA identified through the RT-PCR step was accomplished using the 5'RACE™ reagent system (Life Technologies, Gaithersburg, Md.). One microgram of poly A+ RNA derived from human pituitary gland tissue (Cat. # 65894-1, Lot # 6080167; Clontech Laboratories, Palo Alto, Calif.) was used in a reaction using reagents provided in the kit as described; 1 µl (1 µg) of RNA was combined with 3 µl (3 pmol) Primer 3as and 11 µl Rnase-Free water (water treated with diethylpyrocarbonate, or DEPC) and heated to 70° C. for 10 minutes followed by 1 minute on ice. 2.5 µl 10x reaction buffer (200 mM Tris-HCl pH 8.4, 500 mM KCl), 3 µl 25 mM $MgCl_2$, 1 µl 10 mM dNTP mix, and 2.5 µl 0.1 M DTT were added. The mix was incubated at 42° C. for 2 minutes after which 1 µl Superscript II™ reverse transcriptase (Life Technologies) was added. The reaction was incubated for an additional 30 minutes at 42° C., 15 minutes at 70° C., and on ice for 1 minute. One microliter of RNase H (2 units) was added and incubated at 55° C. for 20 minutes. The cDNA was purified using the GlassMax™ columns included in the kit. The cDNA was eluted from the column in 50 µl distilled water ($dH_2O$), lyophilized, and resuspended in 21 µl $dH_2O$. Tailing of the cDNA was accomplished in the following reaction: 7.5 µl $dH_2O$, 2.5 µl reaction buffer (200 mM Tris-HCl pH 8.4, 500 mM KCl), 1.5 µl 25 mM $MgCl_2$, 2.5 µl 2 mM dCTP, and 10 µl of the cDNA were incubated at 94° C. for 3 minutes, then 1 minute on ice, followed by 10 minutes at 37° C. Finally, the mixture was incubated at 70° C. for 10 minutes and then placed on ice.

PCR amplification of the cDNA was performed in the following steps: 5 µl of the cDNA was included in a reaction which also contained 5 µl 10x GeneAmp™ PCR buffer (Perkin Elmer, Foster City, Calif.) (500 mM KCl, 100 mM Tris-HCl pH 8.3, 15 mM $MgCl_2$, and 0.0% (w/v) gelatin), 1 µl 10 mM dNTP mix, 1 µl (10 pmol) Anchor Primer, 1 µl (10 pmol) Primer 5as, and 35 µl $dH_2O$. The reaction was heated to 95° C. for 1 minute, then held at 80° C. for 2 minutes, during which 0.5 µl (2.5 units) Amplitaq™ polymerase (Perkin-Elmer) was added. The reaction was cycled 35 times under these conditions; 94° C. for 15 seconds, 52° C. for 20 seconds, and 72° C. for 1 minute.

After the amplification, the reaction products were purified utilizing the QiaQuick™ PCR product purification system (Qiagen, Inc., Chatsworth Calif.) as per the manufacturer's instructions. The products were eluted from the columns with 50 µl TE buffer (10 mM Tris, 1 mM EDTA pH 8.0), and one microliter of the eluent was utilized as template DNA in a PCR reaction to increase levels of specific product for subsequent isolation. The reamplification also included: 5 µl 10x GeneAmp™ PCR buffer, 1 µl 10 mM dNTP mix, 1 µl (10 pmol) Universal Amplification Primer, 1 µl (10 pmol) Primer 4as, and 40.5 µl $dH_2O$. The reaction was heated to 95° C. for 1 minute, then held at 80° C. during which 0.5 µl (2.5 units) Amplitaq™ polymerase was added. The reaction was cycled 35 times under these conditions; 94° C. for 15 seconds, 50° C. for 20 seconds, and 72° C. for 1 minute. Amplification products were analyzed via 0.8% agarose gel electrophoresis and a predominant product of approximately 1.3 kilobase pairs in length was detected. This product was excised from the gel and purified via the QiaQuick™ purification system. The product was eluted from the column with 50 µl $dH_2O$ and lyophilized to 10 µl volume.

Three microliters of the resulting DNA was used in a ligation reaction with pCR 2.1 vector (Invitrogen, Carlsbad, Calif.) incubated at 14° C. overnight. The ligation products were used to transform *E. coli* from the cloning kit using standard manufacturer's protocols. Insert sizes of resulting clones were determined using EcoRI digestions of the plasmids and clones containing inserts of the approximate size of the PCR product were sequenced using fluorescent dye-terminator reagents (Prism™, Perkin Elmer Applied Biosystems Division, Foster City, Calif.) and an Applied Biosystems Model 373 DNA sequencer. The sequence of the 5'RACE product including the EcoRI sites from the pCR 2.1 vector is shown in FIG. 1 (SEQ ID NO:13). The sequences of the amplimers (Universal Amplification Primer and the complement to Primer 4as) are underlined.

EXAMPLE 3

Identification of the 3' End of the $P2X_3$ cDNA

To identify the sequence surrounding the termination codon of the open reading frame encoding the human $P2X_3$ receptor, the Life Technologies 3'RACE™ System was employed with primers designed to STS G03901. Poly A+ RNA (500 nanograms) derived from pituitary gland tissue (see Example 2, above) was used in the reaction as follows: The RNA and 10 picomoles Adapter Primer were combined in a final volume of 12 µl $dH_2O$. This mixture was heated to 70° C. for 10 minutes and chilled on ice for 1 minute. The following components were added: 2 µl 10x PCR buffer (200 mM Tris-HCl pH 8.4, 500 mM KCl), 2 µl 25 mM $MgCl_2$, 1 µl 10 mM dNTP mix, and 2 µl 0.1M dithiothreitol. The reaction was equilibrated to 42° C. for 2 minutes after which 1 µl (200 units) Superscript II™ reverse transcriptase was added and incubation continued at 42° C. for 50 minutes. The reaction was terminated by incubation at 70° C. for 15 minutes and chilled on ice. Rnase H (1 µl; 2 units) was added and the mixture was incubated for 20 minutes at 37° C., then stored on ice.

Amplification of the 3' end of the $P2X_3$ cDNA was accomplished in the following reactions: 2 µl of the first strand cDNA synthesized above was used in a PCR mixture also including 5 µl 10x GeneAmp™ PCR buffer, 1 µl 10 mM dNTPs, 1 µl (10 picomoles) Primer 1s, 1 µl (10 picomoles) Abridged Universal Amplification Primer (AUAP) and 39.5 µl $dH_2O$. The reaction was heated to 95° C. for 1 minute, then held at 80° C. for 2 minutes, during which 0.5 µl (2.5 units) Amplitaq™ polymerase was added. The reaction was cycled 35 times under these conditions; 94° C. for 15 seconds, 54° C. for 20 seconds, and 72° C. for 2 minutes. After cycling, the reaction was incubated for 10 minutes at 70° C. and stored at 4° C.

After the amplification, the reaction products were purified utilizing the QiaQuick™ PCR product purification system as per the manufacturer's instructions. The products were eluted from the columns with 50 µl TE buffer (10 mM Tris, 0.1 mM EDTA pH 8.0) and one microliter of the eluent was utilized as template DNA in a PCR reaction to increase levels of specific product for subsequent isolation. The reamplification also included: 5 µl 10x GeneAmp™ PCR buffer, 1 µl 10 mM dNTP mix, 1 µl (10 pmol) AUAP, 1 µl (10 pmol) Primer 2s, and 40.5 µl $dH_2O$. The reaction was heated to 95° C. for 1 minute, then held at 80° C. during which 0.5 µl (2.5 units) Amplitaq™ polymerase was added. The reaction was cycled 35 times under these conditions; 94° C. for 15 seconds, 54° C. for 20 seconds, and 72° C. for 2 minutes. Amplification products were analyzed via 0.8% agarose gel electrophoresis and a predominant product of approximately 700 base pairs in length was detected. This product was excised from the gel and purified via the Qiaquick™ purification system. The product was eluted from the column with 50 µl $dH_2O$ and lyophilized to 10 µl volume.

Three microliters of the above DNA was used in a ligation reaction with pCR 2.1 vector (Invitrogen) incubated at 15° C. for 3.5 hours. The ligation products were used to transform *E. coli* from the cloning kit. Insert sizes of resulting clones were determined using EcoRI digestions of the plasmids and clones containing inserts of the approximate size of the PCR product were sequenced using fluorescent dye-terminator reagents (Prism, Applied Biosystems) and an Applied Biosystems 373 DNA sequencer. The sequence of the 3'RACE product including the EcoRI sites from the pCR 2.1 vector is shown in FIG. 2 (SEQ ID NO:14), in which the sequences of the amplimers (AUAP and the complement to Primer 2s) are underlined.

EXAMPLE 4

Isolation of cDNA Containing the Intact Open Reading Frame of Human P2X$_3$

Using information on the sequence surrounding the initiation and termination codons of the human P2X$_3$ message, oligonucleotide primers were designed and synthesized to enable RT-PCR of the intact open reading frame of the mRNA. The sequences of these primers, designated 5'hP2X$_3$ and 3'hP2X$_3$, are shown above. PCR amplification was performed on a portion (2 μl) of the pituitary gland cDNA described in Example 3. A proofreading thermostable polymerase (Cloned Pfu DNA Polymerase, Strategene, La Jolla, Calif.) was used in the amplification to ensure high-fidelity amplification. The reaction mixture consisted of 2 μl cDNA, 5 μl 10x cloned Pfu polymerase reaction buffer (200 mM Tris-HCl (pH 8.8), 100 mM KCl, 100 mM (NH$_4$)$_2$SO$_4$, 20 mM MgSO$_4$, 1% Triton X-100, 1 mg/ml nuclease-free bovine serum albumin), 1 μl dNTP mix, 1 μl (10 picomoles) 5'hP2X$_3$ Primer, 1 μl (10 picomoles) 3'hP2X$_3$ Primer, and 39.5 μl dH$_2$O. The reaction was heated to 95° C. for 1 minute, then held at 80° C. for 2 minutes, during which time 0.5 μl (1.25 units) cloned Pfu polymerase was added. The reaction was cycled 35 times under the following conditions: 94° C. for 20 seconds, 52° C. for 20 seconds, and 72° C. for 3.5 minutes. After cycling, the reaction was incubated for 10 minutes at 70° C.

The reaction products were separated on a 0.8% agarose gel and a product of approximately 1.2 kilobases was excised and purified via the QiaQuick™ gel purification system. The DNA was eluted with 50 μl dH$_2$O, lyophilized and resuspended in 10 μl dH$_2$O. One microliter of this DNA was use in a reamplification reaction which also inluded 5 μl 10x Pfu reaction buffer, 1 μl dNTP mix, 1 μl (10 picomoles) 5'hP2X$_3$ Primer, 1 μl (10 picomoles) 3'hP2X$_3$ Primer, and 40.5 μl dH$_2$O. The reaction was heated to 95° C. for 1 minute, then held at 80° C. for 2 minutes, during which 0.5 μl (1.25 units) cloned Pfu polymerase was added. The reaction was cycled 15 times under the following conditions: 94° C. for 20 seconds, 52° C. for 20 seconds, and 72° C. for 3.5 minutes. After cycling, the reaction was incubated for 10 minutes at 70° C.

The reaction products were separated on a 0.8% agarose gel and the 1.2 kilobase product was excised and purified via the QiaQuick™ gel purification system. The DNA was eluted with 50 μl dH$_2$O, lyophilized and resuspended in 15 μl dH$_2$O. Three microliters of the purified PCR product was used in a ligation reaction using the pCRscript™ cloning system (stratagene) which also included 0.5 μl (5 ng) of the pCRScript™ Amp SK(+) vector, 1 μl of pCRScript™ 10x Reaction Buffer, 0.5 μl of 10 mM ATP, 1 μl (5 units) Srf I restriction enzyme, 1 μl (4 units) T4 DNA ligase, and 3 μl dH$_2$O. The reaction mixture was incubated at room temperature for one hour, then at 65° C. for 10 minutes.

One microliter of this reaction product was used to transform XL-2 blue ultracompetent cells (Stratagene) as per standard manufacturer's protocols. Resulting clones were screened by restriction analysis and sequenced using fluorescent dye-terminator reagents (Prism, Applied Biosystems) and an Applied Biosystems Model 310 DNA sequencer. The sequence of the intact open reading frame is shown in FIG. 3 (SEQ ID NO:15). A comparison of the predicted protein sequence of the human P2X$_3$ of the present invention (SEQ ID NO:16) with that of the corresponding rat polypeptide (SEQ ID NO:17) is depicted in FIG. 4.

EXAMPLE 5

Expression and Electrophysiological Analysis of Recombinant P2X$_3$ Receptors in Xenopus oocytes Oocytes of *Xenopus laevis* were prepared and injected with receptor DNA of the present invention, and receptor responses were measured using two-electrode voltage-clamp, according to procedures previously described (Briggs et al. (1995), supra). Oocytes were maintained at 17–18° C. in normal Barth's solution (90 mM NaCl, 1 mM KCl, 0.66 mM NaNO$_3$, 0.74 mM CaCl$_2$, 0.82 mM MgCl$_2$, 2.4 mM NaHCO$_3$, 2.5 mM sodium pyruvate, and 10 mM Na N-(2-hydroxy-ethyl)-piperazine-N'-(2-ethanesulfonic acid) ("HEPES") buffer, final pH 7.55) containing 100 μg/ml gentamicin. Responses were measured at a holding potential of −60 mV in modified Barth's solution containing 10 mM BaCl$_2$ and lacking CaCl$_2$ and MgCl$_2$ (final pH 7.4). However, in some experiments, the cell potential was intentionally varied in order to determine the response current-voltage relationship. Agonist was applied briefly using a computer-controlled solenoid valve and a push/pull applicator positioned to within 200–400 μm from the oocyte. Responses were recorded by computer in synchrony with agonist application. Antagonists were included with agonist in the push/pull applicator and were applied to the bath by superfusion for at least 3 minutes before application of agonist. Responses were quantified by measuring the peak amplitude.

DNA for injection into oocytes was the P2X$_3$ insert from pCDNA3.1 prepared as described in Example 2. The clone was grown up and prepared in large scale using the QIAgen maxiprep DNA preparation system according to the manufacturer's instructions. T he DNA was ethanol precipitated and resuspended in TE buffer. For RNA production, the P2X$_3$-pCDNA3.1 construct was linearized by digestion with the restriction enzyme NotI and P2X$_3$ messenger RNA was produced using the T7 promoter in this vector and the Ambion mMessage mMachine™ in vitro transcription kit according to the manufacturer's instructions.

For functional anaysis of human P2X$_3$ receptors, 10 ng of human P2X$_3$ DNA prepared as described above were injected into the nucleus of Xenopus oocytes. Oocytes were incubated in normal Barth's solution containing 100 μg/ml gentamicin for 2–7 days following injection. The response to 10 μM ATP was then recorded.

The results of the above expression and analysis show the receptors of the present invention to be functional. Oocytes injected with human P2X$_3$ DNA responded to extracellular application of ATP by exhibiting a mixed-conductance cation current (100–6000 nA). Oocytes injected with an appropriate amount of water did not respond to ATP. An approximate ATP EC$_{50}$ of 0.7 μM was obtained from concentration-response relationships (0.01–1000 μM) from these oocytes. ATP-induced current-voltage relationships were also recorded from these oocytes. These revealed a reversal potential of approximately zero mV, with pronounced inward rectification recorded at negative membrane potentials.

Another P2X receptor agonist, α,β-methylene-ATP, elicited maximal currents similar to those evoked by ATP, although it was slightly less potent ($EC_{50}$=2.1 μM). Application of a third P2X receptor agonist, 2-methylthio-ATP, was slighly more potent ($EC_{50}$=0.4 μM) than either ATP or α,β-methylene-ATP. Functional antagonism of responses was determined by application of the non-specific P2X receptor antagonists suramin or pyridoxal-phosphate-6-azophenyl-2',4'-disulfonic acid (PPADS). Both antagonists produced a complete block of ATP (0.3 μM)-induced currents, with suramin displaying increased potency ($IC_{50}$= 0.3 μM) relative to PPADS ($IC_{50}$=1 μM).

In summary, injection of human $P2X_3$ receptor DNA into Xenopus oocytes resulted in expression of functional $P2X_3$ receptors on the cell surface, and these receptors function as ligand-gated non-specific cation channels. These receptors responded to extracellular P2 receptor agonists with a rank order potency of 2-methylthio-ATP>ATP>α,β-methylene-ATP. They also exhibit inward rectification and are blocked by both P2 receptor antagonists PPADS and suramin.

EXAMPLE 6

Identification of a Human cDNA Sequence Likely to Encode $P2X_6$ Polypeptide The predicted amino acid sequence of the rat $P2X_6$ receptor (Genbank accession number X92070) was used to search for human DNA sequences which would code for similar polypeptides. The TBLASTN database search tool (Altschul (1993) *J. Mol. Evol.* 36:290–300) was used, which allows querying nucleotide databases with a protein sequence by dynamically translating the DNA sequences into all 6 possible reading frames. A search of the Genbank sequence-tagged sites (STS) database revealed a human genomic fragment, 94 basepairs in length, containing an open reading frame which would be predicted to encode a polypeptide having a high degree of homology to a region of the rat $P2X_6$ receptor. The deposited sequence for this fragment (Genbank accession number H55214) was as follows:

5'-CACCCTGCTCAAGCTCTATG-3'
Primer hP2X6-2s (SEQ ID. NO:23):
   5'-AATCCGCTTCGACATCCTCG-3'
5'RACE Anchor Primer (SEQ ID. NO:7):
   5'-CUACUACUACUAGGCCACGCGTCGACTAGTACGGGIIGGGIIGGGIIG-3'
(where "U" represents uracil and "I" represents inosine)
Adapter Primer (SEQ ID. NO:24):
   5'-GGCCACGCGTCGACTAGTACTTTTTTTTTTTTTTTT-3'
Abridged Universal Adapter Primer (SEQ ID. NO:10):
   5'-GGCCACGCGTCGACTAGTAC-3'
5'hP2X₆ Primer (SEQ ID. NO:25):
   5'-CCACCATGTGCCCGCAGCTAGCAGGAGCTG-3'
3'hP2X₆ Primer (SEQ ID. NO:26):
   5'-GGCTACAGGCTCCCGGAATGGGTTGG-3'

To identify the 5' end of the message which is derived from the genomic region which sequence H55214 is part of, the RACE technique (Rapid Amplification of cDNA Ends) (Frohman et al. (1988), *Proc. Natl. Acad. Sci. U.S.A.* 85:8998–9002) was employed. Extension of the cDNA identified through the RT-PCR step was accomplished using the 5'RACEô reagent system (Life Technologies, Gaithersburg, Md.). 0.5 microgram of poly A+ RNA derived from human hippocampal tissue (Cat. # 6578-1, Lot # 44730; Clontech Laboratories, Palo Alto, Calif.) was used in a reaction using reagents provided in the kit as described; 0.5 μl RNA (1 μg/μl) was combined with 2.5 μl (2.5 pmol) Primer 5as and 12 μl RNase-free water (water treated with diethylpyrocarbonate, or DEPC) heated to 70° C. for 10 min., followed by 1 min. on ice. 2.5 μl 10x reaction buffer (200 mM Tris-HCl pH 8.4, 500 mM KCl), 3 μl 25 mM $MgCl_2$, 1 μl 10 mM dNTP mix, and 2.5 μl 0.1 M DTT were added. The mix was incubated at 42° C. for 2 min. after which 1 μl Superscript IIô reverse transcriptase (Life Technologies) was added. The reaction was incubated for an additional 30 min. at 42° C., 15 min. at 70° C., and on ice for 1 min. one microliter of RNase H (2 units) was added and incubated at 37° C. for 30 min. The cDNA was purified using the GlassMaxô DNA purification columns included in the kit. The cDNA was eluted from the column in 50 μl distilled water ($dH_2O$), lyophilized, and resuspended in 20 μl dH20. Poly dC-tailing of the cDNA was accomplished in the following reaction: 7.5 μl $dH_2O$, 2.5 μl reaction buffer (200 mM Tris-HCl pH 8.4, 500 mM KCl), 1.5 μl 25 MM $MgCl_2$, 2.5 μl 2 mM dCTP, and 10 μl of the cDNA were incubated

```
GACAGCCACT CACTGGTGGG AGCAACCGGG TGTGGAGGCC CGCACCCTGC (SEQ ID NO:18)
TCAAGCTCTA TGGAATCCGC TTCGACATCC TCGTCACCGG GCAG
```

EXAMPLE 7

Identification of the 5' End of the $P2X_6$ cDNA

Based on the sequence of H55214, primers were designed for use in reverse-transcription polymerase chain reaction (RT-PCR) procedures in an effort to isolate the intact open reading frame for this receptor. The primers used in the reactions described below were as follows:
Primer hP2X₆-5as (SEQ ID. NO:19):
   5'-GTGACGAGGATGTCGAAG-3'
Primer hP2X6-6as (SEQ ID. NO:20):
   5'-AGAGCTTGAGCAGGGTGCGG-3'
Primer hP2X6-7as (SEQ ID. NO:21):
   5'-TGCTCCCACCAGTGAGTGGC-3'
Primer hP2X₆-is (SEQ ID. NO:22):

at 94° C. for 3 min., then 1 min. on ice, followed by 10 min. at 37° C. Finally, the mixture was incubated at 70° C. for 10 min. and then placed on ice.

PCR amplification of the cDNA was performed in the following steps: 5 μl of the cDNA was included in a reaction which also contained 5 μl 10x GeneAmpô PCR buffer (Perkin-Elmer, Foster City, Calif.) (500 mM KCl, 100 mM Tris-HCl pH 8.3, 15 mM $MgCl_2$, and 0.01% (w/v) gelatin), 1 μl 10 mM dNTP mix, 1 μl (10 pmol) Anchor Primer, 1 μl (10 pmol) Primer 6as, and 35 μl $dH_2O$. The reaction was heated to 95° C. for 1 min., then held at 80° C. for 2 min., during which 0.5 μl (2.5 units) Amplitaqô polymerase was added. The reaction was cycled 35 times under these conditions: 94° C. for 15 sec., 58° C. for 20 sec., and 72° C. for 1 min. After the final amplification cycle, the reactions were incubated at 70° C. for 10 minutes followed by storage overnight at 4° C.

After the amplification, the reaction products were purified utilizing the QiaQuickô PCR product purification system (Qiagen, Inc., Chatsworth, Calif.) as per manufactureŕs instructions. The products were eluted from the columns with 50 µl TE buffer (10 mM Tris, 1 mM EDTA pH 8.0) and o ne microliter of the eluent was utilized as template DNA in a PCR reaction to increase levels of specific product for subsequent isolation. The reamplification reaction also included: 5 µl 10x GeneAmp PCRô buffer, 1 µl 10 mM dNTP mix, 1 µl (10 pmol) Abridged Universal Amplification Primer, 1 µl (10 pmol) Primer 7as, and 40.5 µl dH$_2$O. The reaction was heated to 95° C. for 1 min., then held at 80° C. while 0.5 µl (2.5 units) Amplitaqô polymerase was added. The reaction was cycled 35 times under these conditions: 94° C. for 15 sec., 50° C. for 20 sec., and 72° C. for 1 min. Amplification products were analyzed via 0.8% agarose gel electrophoresis and a predominant product of approximately 1.0 kilobase pairs in length was detected. This product was excised from the gel and purified via the Qiaquick purification system. The product was eluted from the column with 50 µl dH$_2$O and lyophilized to 10 µl volume.

Two microliters of the resulting DNA was used in a ligation reaction with pCR 2.1 vector (Invitrogen, Carlsbad, Calif.)) incubated at 14° C. for 3.5 hours. The ligation products (1.5 µl of 10 µl reaction were used to transform 50 µl of ultracompetent XL-2 blue *E. coli* (Stratagene, LaJolla, Calif.) using standard manufactureŕs protocols. Insert sizes of resulting clones were determined using EcoRI digestions of the plasmids and clones containing inserts of the approximate size of the PCR product were sequenced using fluorescent dye-terminator reagents (Prismô, Perkin Elmer Applied Biosystems Division, Foster City, Calif.) and an Applied Biosystems Model 373 DNA sequencer. The 5 ́sequence of the RACE product including the predicted initiation codon for the P2X$_6$ message (SEQ ID NO:27) is shown in FIG. 5 with the sequence of the Abridged Universal Amplification Primer underlined. Multiple clones were sequenced and, with the exception of varying poly dC stretches added during the RACE procedure, the consensus is as shown in FIG. 5.

EXAMPLE 8

Identification of the 3' End of the P2X$_6$ cDNA

To identify the sequence surrounding the termination codon of the open reading frame encoding the human P2X$_6$ receptor, the Life Technologies 3íRACE System was employed with primers designed to EST H55241. Poly A+ RNA (500 nanograms) derived from pituitary gland tissue (Cat. # 65894-1, Lot # 6080167; Clontech Laboratories, Palo Alto, Calif.) was used in the reaction as follows: The RNA and 10 picomoles Adapter Primer were combined in a final volume of 12 µl dH$_2$O. This mixture was heated to 70° C. for 10 min. and chilled on ice for 1 min. The following components were added: 2 µl 10x PCR buffer (200 mM Tris-HCl pH 8.4, 500 mM KCl), 2 µl 25 mM MgCl$_2$, 1 µl 10 mM dNTP mix, and 2 µl 0.1M dithiothreitol. The reaction was equilibrated to 42° C. for 2 min. after which 1 µl (200 units) Superscript IIô reverse transcriptase was added and incubation continued at 42° C. for 50 minutes. The reaction was terminated by incubation at 70° C. for 15 min. and chilled on ice. Rnase H (1 µl; 2 units) was added and the mixture was incubated for 20 minutes at 37° C., then stored on ice.

Amplification of the 3' end of the P2X$_6$ cDNA was accomplished in the following reactions: 2 µl of the first strand cDNA synthesized above was used in a PCR mixture also including 5 µl 10x GeneAmpô PCR buffer, 1 µl 10 mM dNTPs, 1 µl (10 picomoles) Primer 1s, 1 µl (10 picomoles) Abridged Universal Amplification Primer (AUAP) and 39.5 µl dH$_2$O. The reaction was heated to 95° C. for 1 min., then held at 80° C. for 2 min., during which 0.5 µl (2.5 units) Amplitaqô polymerase was added. The reaction was cycled 35 times under these conditions: 94° C. for 15 sec., 55° C. for 20 sec., and 72° C. for 2 min. After cycling, the reaction was incubated for 10 minutes at 70° C. and stored at 4° C.

After the amplification, the reaction products were purified utilizing the QiaQuickô PCR product purification system (Qiagen, Inc., Chatsworth Calif.) as per manufactureŕs instructions. The products were eluted from the columns with 50 µl TE buffer (10 mM Tris, 0.1 mM EDTA pH 8.0) and one microliter of the eluent was utilized as template DNA in a PCR reaction to increase levels of specific product for subsequent isolation. The reamplification also included: 5 µl 10x GeneAmpô PCR buffer, 1 µl 10 mM dNTP mix, 1 µl (10 pmol) AUAP, 1 µl (10 pmol) Primer 2s, and 40.5 µl dH$_2$O. The reaction was heated to 95° C. for 1 min., then held at 80° C. during which 0.5 µl (2.5 units) Amplitaqô polymerase was added. The reaction was cycled 35 times under these conditions: 94° C. for 15 sec., 55° C. for 20 sec., and 72° C. for 2 min. After cycling, the reaction was incubated for 10 minutes at 70° C. and stored at 4° C. Amplification products were analyzed via 0.8% agarose gel electrophoresis and two predominant products of approximately 1.3 and 1.5 kilobase pairs in length were detected. This products were excised from the gel and purified via the Qiaquickô purification system. The products were eluted from the columns with 50 µl dH$_2$O and lyophilized to 15 µl volume.

Two microliters of these DNAs were used in ligation reactions with pCR 2.1 vector (Invitrogen, Carlsbad, Calif.)) incubated at 15° C. for 4 hours. The ligation products (1.5 µl of 10 µl reaction) were used to transform 50 µl of ultracompetent XL-2 blue *E. coli* (Stratagene, LaJolla, Calif.) using standard manufactureŕs protocols. Insert sizes of resulting clones were determined using EcoRI digestions of the plasmids and clones containing inserts of the approximate sizes of the PCR products were sequenced using fluorescent dye-terminator reagents (Prismô, Perkin Elmer) and an Applied Biosystems Model 373 DNA sequencer. Although the two PCR products varied in size, the regions encompassing the open reading frame and termination region were found to be identical. This 5' sequence (SEQ ID NO:27) of the two 3'RACE products is shown in FIGS. 6 and 7, in which the sequences of the Primer 2s and the complement to the Adapter Primer are underlined. The 3' end of the two 3'RACE products, including a poly A stretch of variable length, is shown in FIG. 8 (SEQ ID NO:30). With the exception of variable lengths of polyadenlyation, this region was also found to be identical in each of the two sized clones.

EXAMPLE 9

Isolation of cDNA Containing the Intact Open Reading Frame of Human P2X$_6$

Using information on the sequence surrounding the initiation and termination codons of the human P2X$_6$ message, oligonucleotide primers were designed and synthesized to enable RT-PCR of the intact open reading frame of the mRNA. The sequences of these primers, designated 5'h P2X$_6$ and 3'h P2X$_6$, are shown above. The sequence of the gene immediately upstream of the initiation codon was modified in the 5' primer to better match that of a consensus translation initiation region (Kozak (1984), *Nucleic Acids Res.* 12:857–872). Poly A+ RNA derived from human bone marrow (Cat. # 6573-1, Lot # 4Z721; Clontech Laboratories) was used in a first-strand cDNA synthesis reaction as follows: The RNA and 10 picomoles Adapter Primer were combined in a final volume of 12 μl dH$_2$O. This mixture was heated to 70° C. for 10 min. and chilled on ice for 1 min. The following components were added: 2 μl 1X PCR buffer (200 mM Tris-HCl pH 8.4, 500 mM KCl), 2 μl 25 mM MgCl$_2$, 1 μl 10 mM dNTP mix, and 2 μl 0.1M dithiothreitol. The reaction was equilibrated to 42° C. for 2 min. after which 1 μl (200 units) Superscript IIô reverse transcriptase was added and incubation continued at 42° C. for 50 minutes. The reaction was terminated by incubation at 70° C. for 15 min. and chilled on ice. Rnase H (1 μl; 2 units) was added and the mixture was incubated for 20 minutes at 37° C., then stored on ice.

A proofreading thermostable polymerase (Cloned Pfu DNA Polymerase, Stratagene, La Jolla, Calif.) was used in the amplification to ensure high-fidelity amplification. The reaction mixture consisted of 2 μl cDNA, 5 μl 10x cloned Pfu polymerase reaction buffer (200 mM Tris-HCl (pH 8.8), 100 mM KCl, 100 mM(NH$_4$)$_2$SO$_4$, 20 mM Mg SO$_4$, 1% Triton X-100, 1 mg/ml nuclease-free bovine serum albumin), 1 μl dNTP mix, 1 μl (10 picomoles) 5'h P2X$_6$ Primer, 1 μl (10 picomoles) 3'h P2X$_6$ Primer, and 39.5 μl dH$_2$O. The reaction was heated to 95° C. for 1 min., then held at 80° C. for 2 min. during which time 0.5 μl (1.25 units) cloned Pfu polymerase was added. The reaction was cycled 35 times under these conditions: 94° C. for 20 sec., 52° C. for 20 sec., and 72° C. for 3.5 min. After cycling, the reaction was incubated for 10 minutes at 70° C.

The reaction products were separated on a 0.8% agarose gel and a product of approximately 1.2 kilobases was excised and purified via the QiaQuickô gel purification system. The reaction products were separated on a 0.8% agarose gel and the 1.3 kilobase product was excised and purified via the Qiaquickô gel purification system (Qiagen, Inc., Chatsworth, Calif.). The DNA was eluted with 50 μl dH$_2$O, lyophilized and resuspended in 9 μl dH$_2$O. Three microliters of the purified PCR product was used in a ligation reaction using the pCRscriptô cloning system (Stratagene) which also included 0.5 μl (5 ng) of the pCRScriptô Amp SK(+) vector, 1 μl of pCRScriptô 10x Reaction Buffer, 0.5 μl of 10 mM ATP, 1 μl (5 units) Srf I restriction enzyme, 1 μl (4 units) T4 DNA ligase, and 3 μl dH$_2$O. The reaction was incubated at room temperature for one hour, then at 65° C. for 10 minutes.

One microliter of this reaction was used to transform XL-2 blue ultracompetent cells (Stratagene) as per standard manufacturer's protocols. Resulting clones were screened by restriction analysis and sequenced using fluorescent dye-terminator reagents (Prismô, Perkin Elmer) and an Applied Biosystems Model 310 DNA sequencer. Multiple clones were isolated and sequenced; FIG. 8 shows the sequence (SEQ ID NO:30) of the intact open reading frame. A comparison of the predicted protein sequence of the human P2X$_6$ of the present invention (SEQ ID NO:31) with that of the corresponding rat polypeptide (SEQ ID NO:32) is depicted in FIG. 9.

EXAMPLE 10

Expression and Electrophysiological Analysis of Recombinant P2X$_6$ Receptors in Xenopus Oocytes Oocytes of *Xenopus laevis* are prepared and injected with receptor RNA or DNA, and receptor responses are measured using two-electrode voltage-clamp, according to procedures previously described (Briggs et al. (1995), supra). Oocytes are maintained at 17–18° C. in normal Barth's solution (90 mM NaCl, 1 mM KCl, 0.66 mM NaNO$_3$, 0.74 mM CaCl$_2$, 0.82 mM MgCl$_2$, 2.4 mM NaHCO$_3$, 2.5 mM sodium pyruvate, and 10 mM Na N-(2-hydroxy-ethyl)- piperazine-N'-( 2-ethanesulfonic acid) ("HEPES") buffer, final pH 7.55) containing 100 μg/ml gentamicin. Responses are measured at a holding potential of –60 mV in modified Barth's solution containing 10 mM BaCl$_2$ and lacking CaCl$_2$ and MgCl$_2$. However, in some experiments, the cell potential is intentionally varied in order to determine the response current-voltage relationship. Agonist is applied briefly using a computer-controlled solenoid valve and a push/pull applicator positioned to within 200–400 μm from the oocyte. Responses are recorded by computer in synchrony with agonist application. Antagonists are included with agonist in the push/pull applicator and are applied to the bath by superfusion for at least 3 minutes before application of agonist. Responses are quantified by measuring the peak amplitude.

DNA for injection into oocytes is the P2X$_6$ insert from pCDNA3.1 prepared as described in Example 2. The clone is grown and prepared in large scale using the QIAgen maxiprep DNA preparation system according to the manufacturer's instructions. The DNA is ethanol precipitated and resuspended in TE buffer. For RNA production, the P2X$_6$-pCDNA3.1 construct is linearized by digestion with the restriction enzyme NotI and P2X$_6$ messenger RNA is produced using the T7 promoter in this vector and the Ambion mMessage mMachineô in vitro transcription kit according to the manufacturer's instructions.

For functional analysis of human P2X$_6$ receptors according to the present invention, 10 ng of human P2X$_6$ receptor DNA prepared as described above are injected into the nucleus of Xenopus oocytes. Alternatively, 50 ng of human P2X$_6$ receptor RNA prepared as described above are injected into the oocyte cytoplasm. Oocytes are incubated in normal Barth's solution containing 100 μg/ml gentamicin for 2–7 days following injection. The response to 10 μM ATP is then recorded.

EXAMPLE 11

Cloning of Human P2X$_4$ cDNA into pcDNA3.1

A. Identification of a Human Sequence With Homology to P2X Receptors

The predicted amino acid sequence of the rat P2X$_4$ receptor (Genbank accession #X91200) was used to search for human DNA sequences that would code for similar polypeptides. The TBLASTN database search tool (Altschul (1993) *J. Mol. Evol.* 36:290–300) was used, which allows querying nucleotide databases with a protein sequence by dynamically translating the DNA sequences into all six possible reading frames. A search of the Lifeseq database (Incyte Pharmaceuticals, Inc., Palo Alto, Calif.) revealed a partial sequence of a cDNA clone derived from human knee synovium from a patient with rheumatoid arthritis encoding a polypeptide with a high degree of homology to a region of the rat P2X$_4$ receptor. The database entry for this sequence (Incyte clone #1260936) is shown below:

GCGGGNCCATGGCGGGCTGCTGCGCCGCGCTGGNGCCCTTTCCTGTTCGAGTACGACAC (SEQ ID NO:7)

GCCGCGCATCGTGCTCATCCGCAGCCGCAAAGTGGGGCTCATGAACCGCGCCGTGCAAC

TGCTCATCCTGGCCTACGTCATCGGGT
(N = A, T, G, or C)

The position of this sequence with respect to the rat $P2X_4$ sequence predicted that this cDNA clone should contain the entire coding sequence for the human $P2X_4$ receptor. The cDNA clone was ordered from Incyte. Additional clones from the Incyte database (#555697, 095809, 705958, and 711949) and the Genbank dbEST database (#60722) also aligned to the rat $P2X_4$ receptor sequence, and information from these sequences was compiled and used to design primers for PCR amplification of the intact open reading frame (ORF) for the human $P2X_4$ receptor from clone 1260936. The sequence immediately upstream of the initiation codon of the ORF was modified in the design of the primers to incorporate a consensus translation initiation signal to optimize gene expression (Kozak (1984) *Nucl. Acids Res.* 12:857–872). The sequences of the two human $P2X_4$ primers are: 5'-GCGCCACCATGGCGGGCTGCTGCGCCGCGCTG-3' (sense) (SEQ ID NO:8) and 5'-GGTAGGCCTCACTGGTCCAGCTCACTAGCAAG-3' (antisense) (SEQ ID NO:9).

B. Subcloning of the ORF for the Human $P2X_4$ Receptors

To facilitate transfer of the open reading frame of the human $P2X_4$ receptor, polymerase chain amplification reactions were used on the Incyte clone 1260936 using the primers designed from the consensus sequence of the predicted 5' and 3' ends of the open reading frame. Template DNA (100 ng) was used in a 100 μl amplification reaction that also included 200 μM dNTPs, 15 pmoles each primer, 10 μl 10X GeneAmp PCR buffer (Perkin Elmer, Foster City, Calif.) (500 mM KCl, 100 mM Tris-HCl pH 8.3, 15 mM $MgCl_2$, and 0.01% (w/v) gelatin), and 0.5 μl (2.5 units) Amplitaq® polymerase (Perkin Elmer). The reaction was cycled 35 times in a Perkin Elmer Model 9600 thermocycler under the following conditions: 95° C. for 30 sec, 55° C. for 30 sec, and 72° C. for 2 min. The predominant product of 1.2 kilobase pairs was isolated by electrophoresis on a 1% low melting point agarose gel and purified. A portion of the purified product (10%) was used in a ligation reaction with the vector pCRII (Invitrogen, Carlsbad, Calif.) using the manufacturer's protocols. The ligation products were used to transform competent DHS-alpha *E. coli*. Resulting clones were screened by restriction analysis and a representative clone was sequenced using fluorescent dye-terminator reagents (Prism, Perkin Elmer-Applied Biosystems Division) and a Perkin Elmer-Applied Biosystems Model 373 DNA sequencer. The insert from this clone was excised from the vector using the restriction enzyme EcoRI and was used in a ligation reaction with the mammalian expression vector pCDNA3.1(+) (Strategene, La Jolla, Calif.). Reaction products were used to transform competent *E. coli* and resulting clones were screened by restriction analysis. A representative clone was sequenced. The sequence of the insert is shown in FIG. 10. To guard against sequence errors introduced by the DNA amplification process, the ORF contained in the original Incyte clone 1260936 was also sequenced and found to be identical to that of the expression clone.

EXAMPLE 12

Stable Transfection of 1321N1 Cells with $P2X_4$ cDNA

Human astrocytoma cells, 1321N1, were grown to 80% confluence in 35-mm wells in Dulbeccols Modified Eagle's Medium (DMEM) containing 10% fetal bovine serum (FBS). Cells were incubated at 37° C. in a humidified atmosphere containing 5% $CO_2$. Human $P2X_4$ cDNA cloned into pcDNA3.1 as described in Example 11 was transfected into the 1321N1 cells using standard lipid-mediated transfection methodology. Briefly, 2 μg of plasmid DNA was preincubated with 12 μl LipofectAMINE (Life Technologies) in a 1 ml volume of serum-free DMEM for 30 minutes ate room temperature. The 1321N1 cells were washed with serum-free DMEM before the addition of the transfection medium. Cells were incubated with the transfection medium for 3 hours at 37° C. The transfection medium was aspirated and fresh DMEM +10% FBS was added). After 48 hours incubation at 37° C., the cells in a 35-mm dish were split into 5 150-mm plates. The plates were incubated for an additional 7–10 days at 37° C. in DMEM+10% FBS+800 μg/ml Geneticin (G418 antibiotic, Life Technologies). This step selects for cells in which the transfected plasmid has been stably integrated into the host chromosome.

Individual clones were grown to confluence in a 24-well plate in DMEM+10% FBS+300 μg/ml Geneticin. These clones were subsequently screened for functional $P2X_4$ expression using the calcium influx assay on an FLIPR instrument. Several positive clones were identified; one clone, 1321X4-15, was selected for further characterization and for use in the high-throughput screening assay.

EXAMPLE 13

Screening Assay For $P2X_4$ Receptor Ligands

1321X4-15 cells are grown to confluence in black-walled 96-well tissue culture plates in DMEM+10% FBS+300 μg/ml Geneticin. A Fluo-3 μM (Molecular Probes) solution is prepared by dispersing 40 μl of a 1 mg/ml stock DMSO solution into 10 ml Dulbecco's phosphate-buffered saline (D-PBS). The growth medium is aspirated from the cells and the Fluo-3 μM suspension is added. Cells are incubated in the dark for 2 hours at room temperature. In all cases, the tissue culture plates are handled with care because physical agitation might cause the release of endogenous ATP from the cells, thereby activating the $P2X_4$ receptors prior to the assay. Cells are washed gently three times with D-PBS on a Denley Cellwash instrument. The Cellwash leaves a final volume of 100 μl D-PBS in each well.

Three different plates are loaded into a fluorescence imaging plate reader ("FLIPR") for the assay: (1) the 1321X4-15 cell plate (washed); (2) a source plate of test compounds (at 4 times the desired final concentration); and (3) a plate containing approximately 4 times the final concentration of any $P2X_4$ receptor agonist. The cells are assayed in the FLIPR as follows. All pipetting steps are performed by the FLIPR's built-in pipetting armature: 50 μl test compound is added to the cell plate 10 seconds after the start of the run; and 50 μl agonist is added 3 min after the start of the run. The FLIPR instrument collects fluorescence data throughout the course of the run.

EXAMPLE 14

Cloning of Human $P2Y_2$ cDNA into pcDNA3.1

The DNA sequence and amino acid sequence of the reported human $P2Y_2$ (P2U) receptor depicted in FIG. 11A (SEQ ID NO:2) and FIG. 11B (SEQ ID NO:3), respectively, were retrieved from the Genbank database. Amplification primers were designed to amplify the intact open reading frame (ORF) contained in the P2Y$_2$ nucleotide sequence. The sequence immediately upstream of the initiation codon was modified in the design of the primers to incorporate a consensus translation initial signal to optimize recombinant gene expression (Kozak (1984) *Nucl. Acids Res.* 12:857–872). Flanking sense and antisense primers, respectively, used to subclone the human P2Y$_2$ open reading frame, in which the initiation (ATG) and termination (TAG-opposite strand) are underlined,

```
                                              (SEQ ID NO:10)
5'-GCGCGGTACCCACCATGGCAGCAGACCTGGGC-3'
``` and

```
                                              (SEQ ID NO:11)
5'-CTACGACGTCTAGACTACAGCCGAATGTCCTT-3'.
```

A reverse-transcription reaction was performed using standard methods. The 20 µl reaction mixture contained: 2 µg of total RNA from human placental tissue; 4 µl 25 mN MgCl$_2$, 2 µl 10X PCR Buffer II (500 mM KCl, 100 mM Tris-HCl, pH 8.3, and 0.01% (w/v) gelatin) (Perkin Elmer, Foster City, Calif.); 2 µl each 10 mM DATP, dGTP, dCTP, and dTTP; 1 µl RNAse inhibitor (Perkin Elmer); 1 µl 10 mM oligo d(T)$_{16}$ primer; and 1 µl MuLV reverse transcriptase. The reaction was incubated for 10 min at room temperature, 42° C. for 15 min, 99° C. for 5 min, and 5° C. for 5 min. The resulting cDNA was precipitated by adding 2.5 µl of 10 M NH$_4$OAc and 60 µl 100% ethanol, incubated at −20° C. for 1 hr, and centrifuged for 15 min at 4° C. The DNA thus obtained was washed with 70% ethanol and dried in vacuo. The reverse transcriptase products were suspended in 81.5 µl distilled water.

The PCR amplification reaction consisted of the reverse transcriptase products, 10 µl 10X PCR Buffer II, 4 µl 25 mM MgCl$_2$, 2 µl each 10 mM DATP, dGTP, dCTP, and dTTP, 15 picomoles each P2Y$_2$ primer, and 1.5 µl Amplitaq® polymerase (Perkin Elmer). The reaction was cycled 30 times in a Perkin-Elmer model 9600 thermocycler under the following parameters: 95° C., 30 sec; 50° C., 30 sec; and 72° C., 2 min. The major reaction product of 1.1 kilobase pairs was purified via low melting point agarose electrophoresis, and ligated into the vector pCR2.1 (Invitrogen, Carlsbad, Calif.) according to the manufacturer's instructions. The products were used to transform DH5-alpha competent *E.coli* and resulting clones were screened via restriction analysis. The insert from a representative clone was excised by digestion with EcoRI and inserted into the corresponding site of the mammalian expression vector pCDNA3.1 (+). The ligation products were used to transform DH5-alpha competent *E. coli* and resulting clones were screened via restriction analysis. A representative clone was chosen for sequencing via fluorescent dye-terminator reagents (Prism, Perkin Elmer-Applied Biosystems Division) and a Perkin Elmer-Applied Biosystems Model 373 DNA sequencer. The sequence of this clone is shown in FIG. 12A (SEQ ID NO:4), and the predicted amino acid sequence encoded thereby is depicted in FIG. 12B (SEQ ID NO:5). Six differences were observed between the sequence in FIG. 3 and the Genbank submission. These differences would result in three amino acid differences between the predicted polypeptides: R (Genbank) C at position 334; G E at position 350; and F S at position 359. The encoded receptors have been shown to exhibit identical functional characteristics.

EXAMPLE 15

Stable Transfection of 1321N1 Cells With P2Y$_2$ cDNA

The stably transfected 1321Y2-8 cell line was constructed as described in Example 12 substituting the P2Y$_2$ cDNA prepared as described in Example 14 for the P2X$_4$ cDNA.

EXAMPLE 16

Screening Assay For P2Y$_2$ Receptor Ligands

The assay for P2Y$_2$ receptor ligands is conducted as described in Example 13 for P2X$_4$ receptor ligands with the following difference: a 1321Y2-8 cell plate is substituted for the 1321X4-15 cell plate, and the third plate loaded into the FLIPR contains an appropriate amount of the P2 agonist.

EXAMPLE 17

Cloning of Human P2X$_3$ cDNA into pcDNA3.1
A. Identification of a human genomic sequence with homology to P2X receptors.

The predicted amino acid sequence of the rat P2X$_3$ receptor (NCBI seq. I.D. 1103623) was used to search for human DNA sequences which would code for similar polypeptides. The TBLASTN database search tool (Altschul (1993) *J. Mol. Evol.* 36:290–300) was used, which allows querying nucleotide databases with a protein sequence by dynamically translating the DNA sequences into all 6 possible reading frames. A search of the Genbank sequence-tagged sites (STS) database revealed a human genomic fragment containing an open reading frame which encodes a polypeptide with a high degree of homology to a region of the rat P2X$_3$ receptor (Genbank accession number G03901). Primers were designed based on the sequence of G03901 for use in reverse-transcription polymerase chain reaction (RT-PCR) procedures in an effort to isolate the intact open reading frame for this receptor. The primers used in the reactions described below are as follows:

5'TTTACCAACCCAGTGTACCC3' (hP2X$_3$-1S) (SEQ ID NO:12);
5'ACCACAGTGGAGAAGCAGTC3' (hP2X$_3$-2S) (SEQ ID NO:13);
5'GAATCGGTGGACTGCTTCTC3' (hP2X$_3$-3AS) (SEQ ID NO: 14);
5'CGATTTTCAGTGTAGTCTCATTC3' (hP2X$_3$-4AS) (SEQ ID NO: 15)
5'GGGGTACACTGGGTTGGTAA3' (hP2X$_3$-5AS) (SEQ ID NO:16);
5'CUACUACUACUAGGCCACGCGTCGAC-TAGTACGGGIIGGGIIGGGIIG3' (5' RACE Anchor Primer) (SEQ ID NO:17);
5'CUACUACUACUAGGCCACGCGTCGACTAGTAC3' (Universal Adapter Primer) (SEQ ID NO:18);
5'GGCCACGCGTCGACTAG-TACTTTTTTTTTTTTTTTTT3' (Adapter Primer) (SEQ ID NO:19);
5'GGCCACGCGTCGACTAGTAC3' (Abridged Universal Adapter Primer) (SEQ ID NO:20);
5'CACCATGAACTGCATATCCGACTTC3' (5'hP2X$_3$ Primer) (SEQ ID NO:21); and
5'CTAGTGGCCTATGGAGAAGGC3' (3'hP2X$_3$ Primer) (SEQ ID NO:22).
B. Identification of the 5' end of the P2X$_3$ cDNA.
To identify the 5' end of the cDNA which is derived from the genomic region which sequence G03901 is part of, the RACE technique (Rapid Amplification of cDNA Ends)

(Frohman et al. (1988) *Proc. Natl. Acad. Sci. U.S.A.* 85:8998–9002) was employed. Extension of the cDNA identified through the RT-PCR step was accomplished using the 5'RACE reagent system (Life Technologies). One microgram of poly A+ RNA derived from human pituitary gland tissue (Cat. # 65894-1, Lot # 6080167; Clontech Laboratories, Palo Alto, Calif.) was used in a reaction using reagents provided in the kit as described; 1 µl (1 µg) of RNA was combined with 3 µl (3 pmol) primer 3as and 11 µl DEPC-treated water and heated to 70° C. for 10 min. followed by 1 min. on ice. 2.5 µl 10X reaction buffer (200 mM Tris-HCl pH 8.4, 500 mM KCl), 3 µl 25 mM $MgCl_2$, 1 µl 10 mM dNTP mix, and 2.5 µl 0.1 M DTT were added. The mix was incubated at 42° C. for 2 min. after which 1 µl Superscript II reverse transcriptase was added. The reaction was incubated for an additional 30 min. at 42° C., 15 min. at 70° C., and on ice for 1 min. One microliter of RNase H (2 units) was added and incubated at 55° C. for 20 min. The cDNA was purified using the GlassMax columns included in the kit. The cDNA was eluted from the column in 50 µl $dH_2O$, lyophilized, and resuspended in 21 µl $dH_2O$. Tailing of the cDNA was accomplished in the following reaction: 7.5 µl $dH_2O$, 2.5 µl reaction buffer (200 mM Tris-HCl pH 8.4, 500 mM KCl), 1.5 µl 25 mm $MgCl_2$, 2.5 µl 2 mM dCTP, and 10 µl of the cDNA were incubated at 94° C. for 3 min., then 1 min. on ice, followed by 10 min. at 37° C. Finally, the mixture was incubated at 70° C. for 10 min. and then placed on ice. PCR amplification of the cDNA was performed in the following steps: 5 µl of the cDNA was included in a reaction which also contained 5 µl 10x GeneAmp PCR buffer (Perkin-Elmer) (500 mM KCl, 100 mM Tris-HCl pH 8.3, 15 mM $MgCl_2$, and 0.01% (w/v) gelatin), 1 µl 10 mM dNTP mix, 1 µl (10 pmol) anchor primer, 1 µl (10 pmol) primer 2A, and 35 µl $dH_2O$. The reaction was heated to 95° C. for 1 min., then held at 80° C. for 2 min., during which 0.5 µl (2.5 units) Amplitaq polymerase was added. The reaction was cycled 35 times under these conditions; 94° C. for 15 sec., 52° C. for 20 sec., and 72° C. for 1 min. After the amplification, the reaction products were purified utilizing the Cacique PCR product purification system (Qiagen,lnc., Chatsworth Calif.) as per manufacturer's instructions. The products were eluted from the columns with 50 µl TE buffer (10 mM Tris, 1 mM EDTA pH 8.0) and one microliter of the eluent was utilized as template DNA in a PCR reaction to increase levels of specific product for subsequent isolation. The reamplification also included: 5 µl 10x GeneAmp PCR buffer, 1 µl 10 mM dNTP mix, 1 µl (10 pmol) universal amplification primer, 1 µl (10 pmol) primer 4as, and 40.5 µl $dH_2O$. The reaction was heated to 95° C. for 1 min., then held at 80° C. during which 0.5 µl (2.5 units) Amplitaq polymerase was added. The reaction was cycled 35 times under these conditions; 94° C. for 15 sec., 50° C. for 20 sec., and 72° C. for 1 min. Amplification products were analyzed via 0.8% agarose gel electrophoresis and a predominant product of approximately 1.3 kilobase pairs in length was detected. This product was excised from the gel and purified via the Cacique purification system. The product was eluted from the column with 50 µl $dH_2O$ and lyophilized to 10 µl volume. Three microliters of this DNA was used in a ligation reaction with pCR 2.1 vector (Invitrogen, Carlsbad, Calif.)) incubated at 14° C. overnight. The ligation products were used to transform *E. coli* from the cloning kit using standard manufacturer's protocols. Insert sizes of resulting clones were determined using EcoRI digestions of the plasmids and clones containing inserts of the approximate size of the PCR product were sequenced using fluorescent dye-terminator reagents (Prism, Applied Biosystems) and an Applied Biosystems 373 DNA sequencer. The sequence of the RACE product (SEQ ID NO:23), including the EcoRl sites from the TA vector, is shown in FIG. 14.

C. Identification of the 3'end of the $P2X_3$ cDNA.

To identify the sequence surrounding the termination codon of the open reading frame encoding the human $P2X_3$ receptor, the Life Technologies 3'RACE System was employed with primers designed to STS G03901. Poly A+ RNA (500 nanograms) derived from pituitary gland tissue was used in the reaction as follows: The RNA and 10 picomoles primer AP were combined in a final volume of 12 µl $dH_2O$. This mixture was heated to 70° C. for 10 min. and chilled on ice for 1 min. The following components were added: 2 µl 10X PCR buffer (200 mM Tris-HCl pH 8.4, 500 mM KCl), 2 µl 25 mM $MgCl_2$, 1 µl 10 mM dNTP mix, and 2 µl 0.1 M dithiothreitol. The reaction was equilibrated to 42° C. for 2 min. after which 1 µl (200 units) Superscript II reverse transcriptase was added and incubation continued at 42° C. for 50 minutes. The reaction was terminated by incubation at 70° C. for 15 min. and chilled on ice. Rnase H (1 µl; 2 units) was added and the mixture was incubated for 20 minutes at 37° C., then stored on ice.

Amplification of the 3' end of the $P2X_3$ cDNA was accomplished in the following reactions: 2 µl of the first strand cDNA synthesized above was used in a PCR mixture also including 5 µl 10X GeneAmp PCR buffer, 1 µl 10 mM dNTPs, 1 µl (10 picomoles) $P2X_3$ primer 1s, 1 µl (10 picomoles) abridged universal amplification primer (AUAP) and 39.5 µl $dH_2O$. The reaction was heated to 95° C. for 1 min., then held at 80° C. for 2 min., during which 0.5 µl (2.5 units) Amplitaq polymerase was added. The reaction was cycled 35 times under these conditions; 94° C. for 15 sec., 54° C. for 20 sec., and 72° C. for 2 min. After cycling, the reaction was incubated for 10 minutes at 70° C. and stored at 4° C. After the amplification, the reaction products were purified utilizing the QiaQuick PCR product purification system as per manufacturer's instructions. The products were eluted from the columns with 50 µl TE buffer (10 mM Tris, 0.1 mM EDTA pH 8.0) and one microliter of the eluent was utilized as template DNA in a PCR reaction to increase levels of specific product for subsequent isolation. The reamplification also included: 5 µl 10X GeneAmp PCR buffer, 1 µl 10 mm dNTP mix, 1 µl (10 pmol) AUAP, 1 µl (10 pmol) primer 2s, and 40.5 µl $dH_2O$. The reaction was heated to 95° C. for 1 min., then held at 80° C. during which 0.5 µl (2.5 units) Amplitaq polymerase was added. The reaction was cycled 35 times under these conditions; 94° C. for 15 sec., 54° C. for 20 sec., and 72° C. for 2 min. Amplification products were analyzed via 0.8% agarose gel electrophoresis and a predominant product of approximately 700 base pairs in length was detected. This product was excised from the gel and purified via the Qiaquick purification system. The product was eluted from the column with 50 µl $dH_2O$ and lyophilized to 10 µl volume. Three microliters of this DNA was used in a ligation reaction with pCR 2.1 vector (Invitrogen, Carlsbad, Calif.)) incubated at 15° C. for 3.5 hours. The ligation products were used to transform *E. coli* from the cloning kit. Insert sizes of resulting clones were determined using EcoRI digestions of the plasrnids and clones containing inserts of the approximate size of the PCR product were sequenced using fluorescent dye-terminator reagents (Prism, Applied Biosystems) and an Applied Biosystems 373 DNA sequencer. The sequence of the RACE product (SEQ ID NO:24), including the EcoRI sites from the TA vector, are shown in FIG. 15.

D. Isolation of cDNA containing the intact open reading frame for human P2X$_3$

Using information on the sequence surrounding the initiation and termination codons of the human P2X$_3$, message, oligonucleotide primers were designed and synthesized to enable RT-PCR of the intact open reading frame of the mRNA. The sequence of these primers, hP2X$_3$5', and hP2X$_3$3', are given above. PCR amplification was performed on a portion (2 µl) of the pituitary gland cDNA described above. A proofreading thermostable polymerase (Cloned Pfu DNA Polymerase, Stratagene) was used in the amplification to ensure high-fidelity amplification. The reaction mixture consisted of. 2 µl cDNA, 5 µl 10X cloned Pfu polymerase reaction buffer (200 mM Tris-HCl (pH 8.8), 100 mM KCl, 100 mM (NH$_4$)$_2$SO$_4$, 20 mM MgSO$_4$, 1µl Triton X-100, 1 mg/ml nuclease-free bovine serum albumin), 1 µl dNTP mix, 1 µl (10 picomoles) 5'hP2X$_3$ primer, 1 µl (10 picomoles) 3'hP2X$_3$ primer, and 39.5 µl dH$_2$O. The reaction was heated to 95° C. for 1 min., then held at 80° C. for 2 min., during which 0.5 µl (1.25 units) cloned Pfu polymerase was added. The reaction was cycled 35 times under these conditions; 94° C. for 20 sec., 52° C. for 20 sec., and 72° C. for 3.5 min. After cycling, the reaction was incubated for 10 minutes at 70° C. The reaction products were separated on a 0.8% agarose gel and a product of approximately 1.2 kilobases was excised and purified via the Qiaquick gel purification system. The DNA was eluted with 50 µl dH$_2$O, lyophilized and resuspended in 10 µl dH$_2$O. One microliter of this DNA was use in a reamplification reaction which also included 5 µl 10X Pfu reaction buffer, 1 µl dNTP mix, 1 µl (10 picomoles) 5'hP2X$_3$ primer, 1 µl (10 picomoles) 3'hP2X$_3$ primer, and 40.5 µl dH$_2$O. The reaction was heated to 95° C. for 1 min., then held at 80° C. for 2 min., during which 0.5 µl (1.25 units) cloned Pfu polymerase was added. The reaction was cycled 15 times under these conditions; 94° C. for 20 sec., 52° C. for 20 sec., and 72° C. for 3.5 min. After cycling, the reaction was incubated for 10 minutes at 70° C. The reaction products were separated on a 0.8% agarose gel and the 1.2 kilobase product was excised and purified via the Qiaquick gel purification system. The DNA was eluted with 50 µl dH$_2$O, lyophilized and resuspended in 15 µl dH$_2$O. Three microliters of the purified PCR product was used in a ligation reaction using the pCRscript cloning system (Stratagene)which also included: 0.5 µl (5 ng) of the pCR-Script Amp SK(+) vector, 1 µl of pCRScript 10X Reaction Buffer, 0.5 µl of 10 mM ATP, 1 µl (5 units) Srf I restriction enzyme, 1 µl (4 units) T4 DNA ligase, and 3 µl dH$_2$O. The reaction was incubated at room temperature for one hour, then at 65° C. for 10 minutes. One microliter of this reaction mix was used to transform XL-2 blue ultracompetent cells (Stratagene) as per standard manufacturer's protocols. Resulting clones were screened by restriction analysis and sequenced using fluorescent dye-terminator reagents (Prism, Applied Biosystems) and an Applied Biosystems 310 DNA sequencer. The sequence of the intact open reading frame (SEQ ID NO:6) is shown in FIG. 13, in which the initiation codon (ATG) and termination codon (TAG) are in bold. 5' and 3' flanking sequences, including the EcoRI (GAATTC) and Not I (GCGGCCGC) restriction sites, is sequence introduced during plasmid construction and are underlined.

EXAMPLE 18

Stable Transfection of 1321N1 Cells With P2X$_3$ cDNA

The stably transected 1321X3-11 cell line was constructed as described in Example 12, substituting P2X$_3$ cDNA prepared as described in Example 17 for the P2X$_4$ cDNA.

EXAMPLE 19

Screening Assay For P2X$_3$ Purinoreceptor Ligands

The screening assay for P2X$_3$ receptor ligands is conducted as described in Example 13 for P2X$_4$ purinoreceptor ligands with the following differences: A 1321X3-11 cell plate is substituted for the 1321X4-15 cell plate, and the third plate contains an appropriate amount of P2X$_3$ agonist.

EXAMPLE 20

Cloning, Expression and Utilization of Other Purinoreceptors

Transformed host cells, and screening assays utilizing such cells, are prepared according to the procedures of the foregoing examples for the following human receptor clones:

| Clone | Accession No. | Tissue Source |
| --- | --- | --- |
| hP2X$_1$ | X83688 | urinary bladder |
| hP2X$_3$ | Y07683 | heart |
| hP2X$_4$ | Y07684 | brain |
| hP2X$_{M(6)}$ | AB002058 | skeletal muscle |
| hP2X$_7$ | Y09561 | brain |
| hP2Y$_1$ | U42030 | erythroleukemia cells |
| hP2Y$_2$ | U07225 | airway epithelium |
| hP2Y$_4$ | X91852 | placenta |
| hP2Y$_6$ | X97058 | airway epithelium |

In each case, PCR primers are prepared according to the sequence information available at the respective GenBank accession number. The primers are then used to clone the DNA sequence of interest into a suitable cloning vector, following the procedures described in Examples 1 and 7 above. After stable transfection of the receptor DNA into appropriate host cells according to the procedures of Examples 2 and 8, screening assays for receptor ligands are conducted as described in Example 13 with any necessary modifications and/or substitutions.

What is claimed is:

1. An isolated polynucleotide encoding a human $P2X_3$ receptor polypeptide comprising the amino acid sequence of SEQ ID NO:16.

2. A polynucleotide according to claim 1, wherein the polynucleotide is a polydeoxyribonucleotide (DNA).

3. A polynucleotide according to claim 1, wherein the polynucleotide is a polyribonucleotide (RNA).

4. A polynucleotide according to claim 2, wherein the DNA comprises the sequence of SEQ ID NO:15.

5. A host cell comprising a polynucleotide according to claim 1 or claim 4.

6. A host cell according to claim 5, wherein said cell is selected from the group consisting of a bacterial cell, a mammalian cell, a yeast cell and an amphibian cell.

7. A host cell according to claim 6, wherein the cell is an amphibian cell.

8. A host cell according to claim 6, wherein the cell is a mammalian cell.

9. An expression vector comprising a polynucleotide according to claim 1 operably linked to control sequences that direct the transcription of the polynucleotide, whereby the polynucleotide is expressed in a host cell.

10. A host cell comprising an expression vector according to claim 9.

11. A host cell according to claim 10, wherein the cell is selected from the group consisting of a bacterial cell, a mammalian cell, a yeast cell and an amphibian cell.

12. A host cell according to claim 11, wherein the cell is an amphibian cell.

13. A host cell according to claim 11, wherein the cell is a mammalian cell.

14. A method for producing a human $P2X_3$ receptor polypeptide, the method comprising the steps of:

(a) culturing a host cell according to claim 10 under conditions that allow the production of the polypeptide; and (b) recovering the polypeptide.

* * * * *

UNITED STATES PATENT AND TRADEMARK OFFICE
CERTIFICATE OF CORRECTION

PATENT NO. : 6,214,581 B1
DATED : April 10, 2001
INVENTOR(S) : Kevin J. Lynch, et al.

It is certified that error appears in the above-identified patent and that said Letters Patent is hereby corrected as shown below:

<u>Title page,</u>
Item [54] Title replace "P2X3 AND P2X6," with -- P2X3 AND P2X6 --

Signed and Sealed this

Eleventh Day of December, 2001

Attest:

NICHOLAS P. GODICI
*Attesting Officer*     *Acting Director of the United States Patent and Trademark Office*